(12) United States Patent
Ashby et al.

(10) Patent No.: US 12,193,677 B2
(45) Date of Patent: Jan. 14, 2025

(54) EXPANDABLE DEVICES AND ASSOCIATED SYSTEMS AND METHODS

(71) Applicant: Covidien LP, Mansfield, MA (US)

(72) Inventors: Mark Philip Ashby, Laguna Niguel, CA (US); Ashok Nageswaran, Irvine, CA (US); Eric Mintz, Newport Coast, CA (US); Gaurav Girdhar, Ladera Ranch, CA (US); Ujwal Ramesh Jalgonkar, Irvine, CA (US); John Wainwright, Foothill Ranch, CA (US)

(73) Assignee: COVIDIEN LP, Mansfield, MA (US)

( * ) Notice: Subject to any disclaimer, the term of this patent is extended or adjusted under 35 U.S.C. 154(b) by 113 days.

(21) Appl. No.: 17/653,269

(22) Filed: Mar. 2, 2022

(65) Prior Publication Data

US 2023/0277187 A1 Sep. 7, 2023

(51) Int. Cl.
*A61B 17/12* (2006.01)

(52) U.S. Cl.
CPC .. *A61B 17/12118* (2013.01); *A61B 17/12168* (2013.01); *A61B 2017/1205* (2013.01)

(58) Field of Classification Search
CPC ........ A61B 17/12118; A61B 17/12168; A61B 2017/1205; A61B 2017/12054; A61B 2017/12063; A61B 2017/12095; A61F 2/011; A61F 2/2427; A61F 2/82; A61F 2/95; A61F 2/954; A61F 2/958; A61F 2/962; A61F 2/966; A61F 2/97; A61F 2002/065; A61F 2002/067; A61F 2002/823; A61F 2002/9505; A61F 2002/9511; A61F 2002/9517; A61F 2002/9522; A61F 2002/9528; A61F 2002/9534; A61F 2002/9665
See application file for complete search history.

(56) References Cited

U.S. PATENT DOCUMENTS 5,674,241 A 10/1997 Bley et al.
5,873,907 A * 2/1999 Frantzen .................. A61F 2/95
606/191

(Continued)

FOREIGN PATENT DOCUMENTS

WO 2013009976 A2 1/2013

OTHER PUBLICATIONS

International Search Report and Written Opinion mailed Apr. 20, 2023; International Application No. PCT/US2023/011809; 15 pages.

*Primary Examiner* — Kelly J Bekker
*Assistant Examiner* — Nasheha Baset
(74) *Attorney, Agent, or Firm* — Fortem IP LLP

(57) ABSTRACT

Expandable devices for occluding bifurcation aneurysms are disclosed herein. Several of the embodiments are directed towards an expandable device comprising a mesh configured to be deployed at a treatment site including blood vessel bifurcation of a human patient so that the mesh extends across a neck of an aneurysm and prevents or limits blood flow through the mesh and into the aneurysm. The mesh can comprise one or more circumferentially discontinuous portions so that, when the device is deployed at the treatment site, the device does not substantially impede flow from a parent blood vessel to two or more branching blood vessels. Systems and methods for delivering an expandable device of the present technology are also disclosed herein.

21 Claims, 34 Drawing Sheets

(56) References Cited

U.S. PATENT DOCUMENTS

| | | | |
|---|---|---|---|
| 6,149,681 A | 11/2000 | Houser et al. | |
| 6,168,618 B1* | 1/2001 | Frantzen | A61F 2/95 |
| | | | 623/1.11 |
| 6,682,557 B1 | 1/2004 | Quiachon et al. | |
| 8,328,861 B2* | 12/2012 | Martin | A61F 2/954 |
| | | | 623/1.11 |
| 10,342,686 B2 | 7/2019 | Choubey | |
| 2002/0026232 A1* | 2/2002 | Marotta | A61F 2/82 |
| | | | 623/1.16 |
| 2002/0120325 A1 | 8/2002 | Richter et al. | |
| 2004/0127975 A1* | 7/2004 | Levine | A61B 17/12172 |
| | | | 623/1.11 |
| 2004/0138736 A1 | 7/2004 | Obara | |
| 2004/0158311 A1 | 8/2004 | Berhow et al. | |
| 2006/0116748 A1 | 6/2006 | Kaplan et al. | |
| 2011/0046720 A1 | 2/2011 | Shalev et al. | |
| 2014/0148891 A1* | 5/2014 | Johnson | A61F 2/954 |
| | | | 623/1.11 |
| 2017/0273692 A1 | 9/2017 | Choubey | |
| 2017/0273810 A1 | 9/2017 | Choubey et al. | |
| 2018/0177622 A1* | 6/2018 | Chu | A61F 2/06 |
| 2018/0200092 A1 | 7/2018 | Nageswaran et al. | |
| 2019/0133795 A1 | 5/2019 | Choubey | |
| 2019/0192322 A1 | 6/2019 | Choubey et al. | |
| 2019/0223879 A1 | 7/2019 | Jayaraman | |
| 2019/0269534 A1 | 9/2019 | Choubey | |
| 2019/0314175 A1 | 10/2019 | Dawson et al. | |
| 2019/0314176 A1 | 10/2019 | Nageswaran et al. | |
| 2019/0314177 A1 | 10/2019 | Alonso et al. | |
| 2019/0314179 A1 | 10/2019 | Nageswaran et al. | |
| 2019/0380852 A1* | 12/2019 | Eker | A61F 2/07 |
| 2022/0061854 A1 | 3/2022 | Jalgaonkar et al. | |

\* cited by examiner

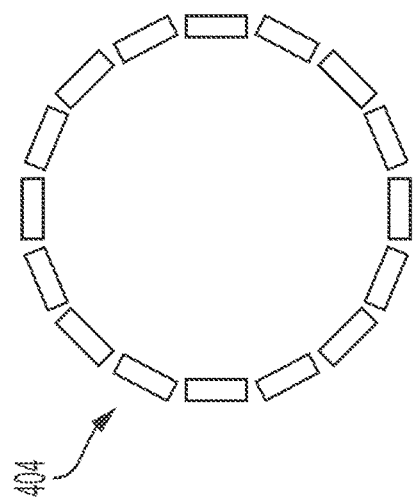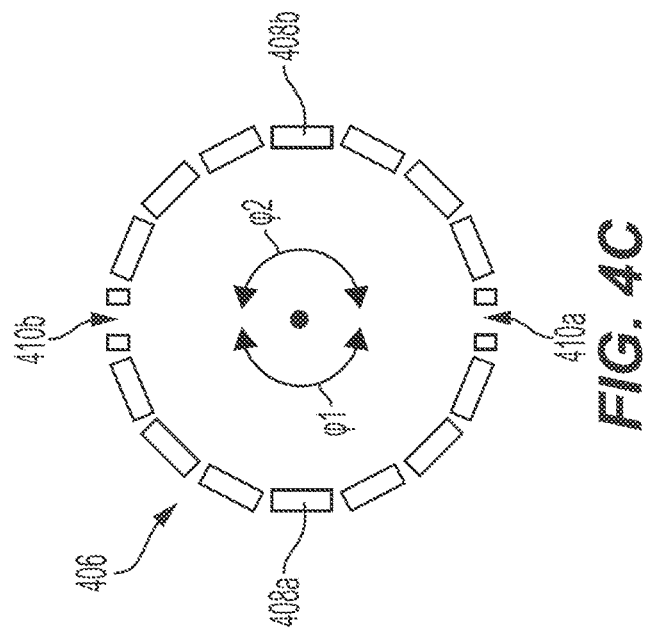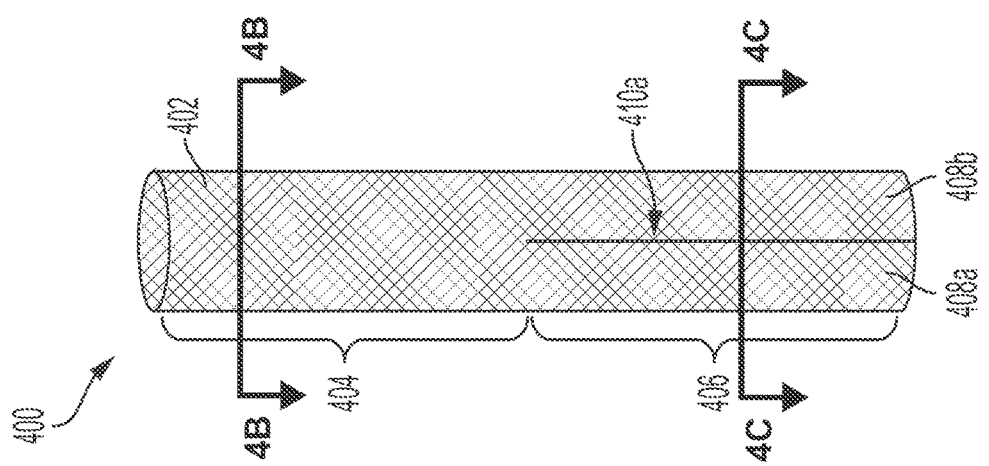

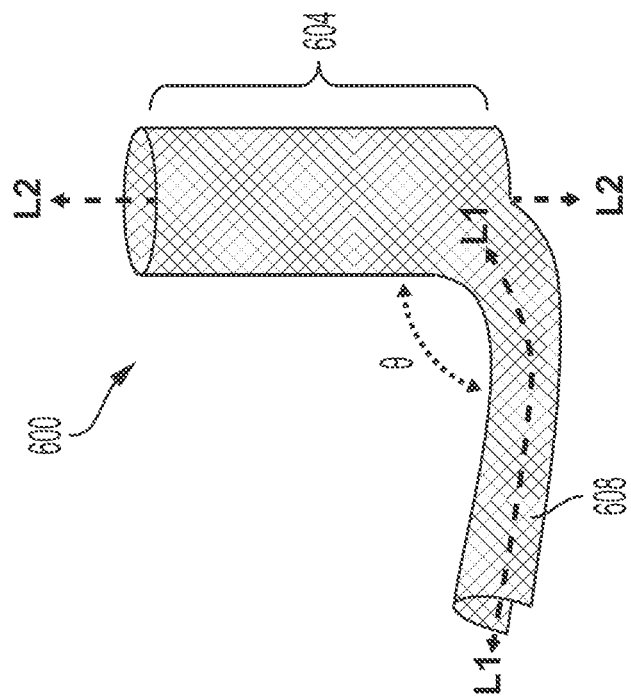
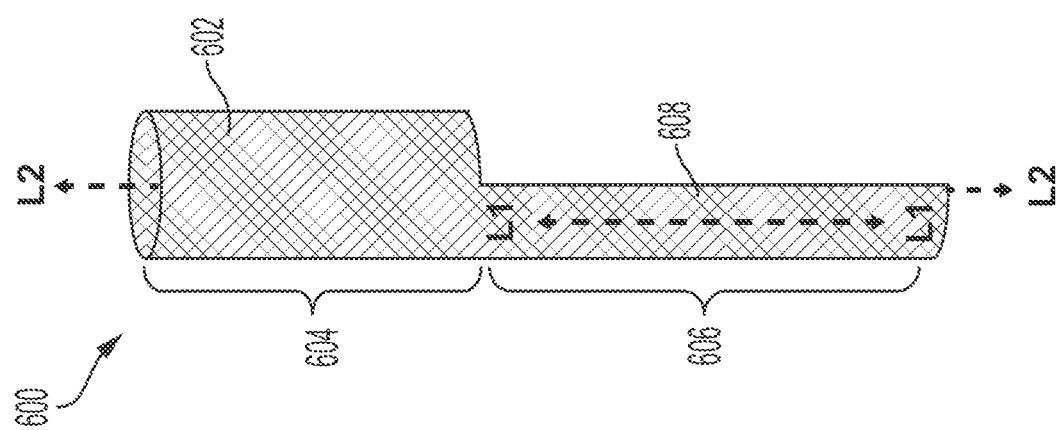
FIG. 6B
FIG. 6A

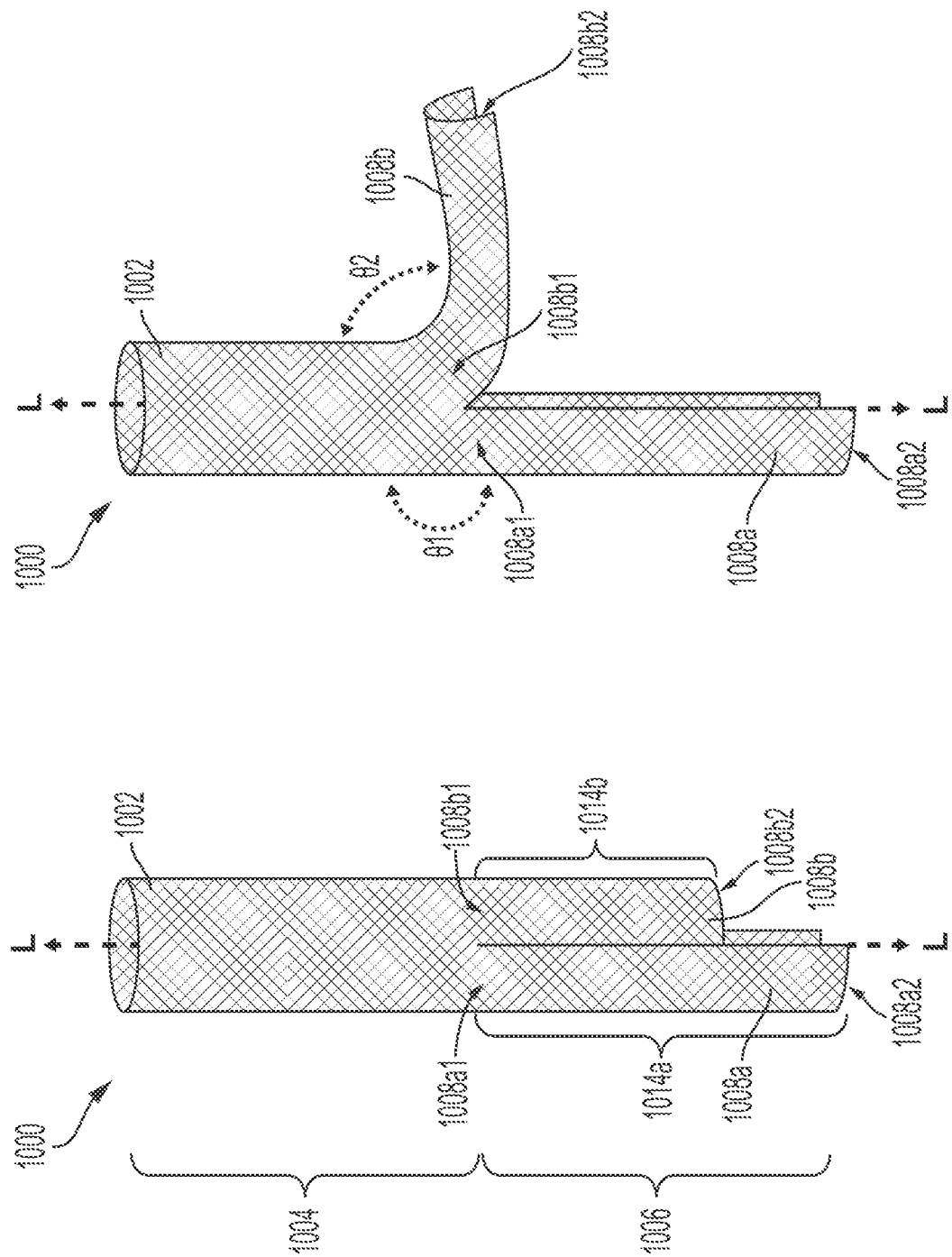

EXPANDABLE DEVICES AND ASSOCIATED SYSTEMS AND METHODS

TECHNICAL FIELD

The present technology relates to expandable devices and associated systems and methods. In some embodiments, the present technology relates to devices for preventing blood flow into an aneurysm at a bifurcation of a blood vessel, and associated systems and methods of use.

BACKGROUND

Aneurysms are an abnormal bulging or ballooning of a blood vessel that can result from the vessel wall being weakened by disease, injury, or a congenital abnormality. Aneurysms have thin, weak walls and a tendency to rupture, which can lead to stroke, death, disability, etc. Aneurysms may be treated by positioning an occlusive device (e.g., coils, braids, liquid embolics, etc.) within the aneurysm to reduce blood flow and promote thrombosis and embolization within the aneurysm. However, intrasaccular occlusive devices may relocate out of the aneurysm and into the vessel with aneurysms with wide necks, which may lead to arterial occlusion, stroke, and/or death.

Another method of treating aneurysms includes inserting a flow-diverting stent or braid into a parent vessel that includes the aneurysm to be treated. Such stents or braids can be inserted into a vessel in a radially constrained state, positioned next to the neck of the aneurysm, and expanded into apposition with the vessel wall. If the stent or braid has a sufficiently low porosity, it can function to block the flow of blood through the device and into the aneurysm to induce embolization of the aneurysm. A flow-diverting device may be placed within two vessels (e.g., a parent vessel and a first branching vessel, a first branching vessel and a second branching vessel) to treat a bifurcation aneurysm between the vessels. However, flow-diverting devices typically comprise a tubular structure. Consequently, when such flow-diverting devices are placed across the neck of the aneurysm, a portion of the device is positioned across a juncture to another blood vessel and disrupts blood flow to the vessel. Accordingly, there exists a need for improved flow-diverting devices for treating bifurcation aneurysms.

SUMMARY

The present technology is directed to devices for treating bifurcation aneurysms and associated systems and methods. According to some embodiments, an expandable device of the present technology comprises a mesh with articulating portions angled with respect to one another when the device is in an expanded state. A device of the present technology can be positioned within a patient's vasculature such that an articulating portion is positioned within at least two blood vessel lumens at a bifurcation of a blood vessel. The expandable devices of the present technology may be particularly beneficial for treating bifurcation aneurysms at a location in which a parent blood vessel branches into two or more branching vessels. The treatment of bifurcation aneurysms with flow-diverting devices presents unique challenges associated with positioning an occlusive mesh over a neck of the aneurysm without substantially disrupting flow through the parent and branching vessels at a bifurcation. To address such challenges, the expandable devices of the present technology comprise at least one circumferentially discontinuous portion configured to be positioned across an aneurysm located between two vessels at a bifurcation. The circumferential discontinuity of such portion of the device can enable the device to cover the neck of the aneurysm without covering a junction between two vessels. Accordingly, expandable devices of the present technology can have a sufficiently high surface coverage (e.g., at least 20%) to facilitate occlusion of the aneurysm while permitting substantially unobstructed blood flow through the vessels at the bifurcation.

The subject technology is illustrated, for example, according to various aspects described below, including with reference to FIGS. 1A-20G. Various examples of aspects of the subject technology are described as numbered clauses (1, 2, 3, etc.) for convenience. These are provided as examples and do not limit the subject technology.

Clause 1. An expandable device configured to be positioned across a neck of an aneurysm at a bifurcation of a blood vessel of a patient, the device comprising:
  a generally tubular mesh having a first end portion and a second end portion, the second end portion comprising a first articulating region and a second articulating region,
  wherein the first articulating region is separated from the second articulating region by first and second slits, the first and second slits extending along a longitudinal axis of the mesh, and
  wherein, when the mesh is in an expanded state, the first articulating region is positioned at a first angle relative to the first end portion and the second articulating region is positioned at a second angle relative to the first end portion.

Clause 2. The device of Clause 1, wherein a length of the first slit is equal to a length of the second slit.

Clause 3. The device of any one of the preceding Clauses, wherein the first slit is circumferentially spaced apart from the second slit by about 180 degrees.

Clause 4. The device of any one of the preceding Clauses, wherein a width of the first articulating region is less than a width of the second articulating region.

Clause 5. The device of any one of the preceding Clauses, wherein the first angle is about 0 degrees and the second angle is between about 30 degrees and 150 degrees.

Clause 6. The device of any one of the preceding Clauses, wherein the first angle is substantially equivalent to the second angle.

Clause 7. The device of any one of the preceding Clauses, wherein the first and second slits are formed by mechanical or laser cutting.

Clause 8. The device of any one of the preceding Clauses, wherein longitudinal edges of the first and second articulating regions adjacent first and second slits have been soldered, melted, welded, or glued.

Clause 9. The device of any one of the preceding Clauses, the mesh further comprising a third slit extending circumferentially between the first slit and the second slit.

Clause 10. The device of any one of the preceding Clauses, further comprising a plurality of radiopaque markers positioned around a circumference of the first end portion of the mesh.

Clause 11. The device of any one of the preceding Clauses, further comprising a first plurality of radiopaque markers attached to the first articulating region and a second plurality of radiopaque makers attached to the second articulating region.

Clause 12. The device of any one of the preceding Clauses, wherein the first plurality of radiopaque markers comprises fewer radiopaque markers than the second plurality of radiopaque markers.

Clause 13. The device of any one of the preceding Clauses, wherein a length of the first articulating region is greater than a length of the second articulating region.

Clause 14. A device configured to be positioned across a neck of an aneurysm at a bifurcation of a blood vessel of a patient, the device comprising:
   an expandable mesh having a generally tubular body portion and a circumferentially discontinuous arm portion extending from the body portion, wherein, when the expandable mesh is in a low-profile configuration, a longitudinal axis of the arm portion is generally parallel with a longitudinal axis of the body portion, and wherein, when the expandable mesh is in an expanded configuration, a longitudinal axis of the arm portion is positioned at an angle with respect to the longitudinal axis of the body portion.

Clause 15. The device of any one of the preceding Clauses, wherein the angle is between about 30 degrees and about 150 degrees Clause 16. The device of any one of the preceding Clauses, wherein the body portion is configured to be positioned within a first blood vessel and the arm portion is configured to be placed within a second blood vessel.

Clause 17. The device of any one of the preceding Clauses, wherein the arm portion is a first arm portion, the mesh further comprising a second arm portion extending from the body portion, wherein, when the expandable mesh is in an expanded configuration, a longitudinal axis of the first arm portion is positioned at a first angle to the longitudinal axis of the body portion and a longitudinal axis of the second arm portion is positioned at a second angle to the longitudinal axis of the body portion.

Clause 18. The device of any one of the preceding Clauses, wherein the mesh is configured to divert blood flow away from the aneurysm.

Clause 19. The device of any one of the preceding Clauses, wherein the mesh comprises a braid.

Clause 20. The device of any one of the preceding Clauses, wherein the mesh is self-expanding.

Clause 21. The device of any one of the preceding Clauses, wherein the mesh is formed of a shape memory alloy.

Clause 22. The device of any one of the preceding Clauses, wherein the body portion is configured to be positioned within a first branching blood vessel, the first arm portion is configured to be placed within a second branching blood vessel, and the second arm portion is configured to be placed within a parent blood vessel.

Clause 23. The device of any one of the preceding Clauses, wherein the mesh is configured to anchor to a wall of the blood vessel of the patient.

Clause 24. A device for reducing blood flow within an aneurysm of a blood vessel, the device comprising:
   an expandable mesh comprising a circumferentially discontinuous first portion, a circumferentially discontinuous second portion, and a generally tubular third portion, the expandable device having a radially constrained configuration and an expanded configuration,
   wherein, when the expandable mesh is in the radially constrained configuration the device comprises a substantially tubular shape,
   wherein, when the expandable mesh is in the expanded configuration, the first portion is configured to be positioned within a parent blood vessel, the second portion is configured to be positioned within a first branching blood vessel, and the third portion is configured to be positioned within a second branching blood vessel, and
   wherein, when positioned across a neck of the aneurysm, the device is configured to substantially block blood flow into the aneurysm and permit blood flow from the parent blood vessel to the first and second branching blood vessels.

Clause 25. The device of any one of the preceding Clauses, wherein the second and third portions are configured to substantially cover the neck of the aneurysm.

Clause 26. The device of any one of the preceding Clauses, wherein the first and third portions are configured to substantially cover the neck of the aneurysm.

Clause 27. The device of any one of the preceding Clauses, wherein the first and second portions are configured to substantially cover the neck of the aneurysm.

Clause 28. A device for reducing blood flow within an aneurysm of a blood vessel, the device comprising:
   an expandable mesh comprising a first portion, a second portion, and a third portion, wherein at least one of the portions is circumferentially discontinuous, the expandable device having a radially constrained configuration and an expanded configuration,
   wherein, when the expandable mesh is in the radially constrained configuration the device comprises a substantially tubular shape,
   wherein, when the expandable mesh is in the expanded configuration, the first portion is configured to be positioned within a parent blood vessel, the second portion is configured to be positioned within a first branching blood vessel, and the third portion is configured to be positioned within a second branching blood vessel, and
   wherein, when positioned across the neck of the aneurysm, the device is configured to substantially block blood flow into the aneurysm and permit blood flow from the parent blood vessel to the first and second branching blood vessels.

Clause 29. The device of any one of the preceding Clauses, wherein the third portion is substantially tubular and the first and second portions are circumferentially discontinuous.

Clause 30. The device of any one of the preceding Clauses, wherein the first and third portions are substantially tubular and the second portion is circumferentially discontinuous.

Clause 31. The device of any one of the preceding Clauses, wherein the at least one of the portions subtends an angle of about 30 degrees to about 330 degrees.

Clause 32. The device of any one of the preceding Clauses, wherein the at least one of the portions subtends an angle of about 180 degrees.

Clause 33. A method of making an expandable device comprising:
   obtaining a tubular mesh having a porosity configured to divert blood flow, the tubular mesh comprising a first end portion, a second end portion, and an intermediate portion therebetween;
   forming a circumferentially discontinuous arm portion from the second end portion of the tubular mesh, the arm portion being movable relative to the first end portion of the mesh;

manipulating the mesh into an expanded configuration; and shape-setting the mesh in the expanded configuration.

Clause 34. The method of any one of the preceding Clauses, wherein forming the arm portion comprises creating at least two slits in the tubular mesh.

Clause 35. The method of any one of the preceding Clauses, wherein manipulating the mesh into an expanded configuration comprises obtaining a fixture and coupling the mesh to the fixture.

Clause 36. The method of any one of the preceding Clauses, wherein shape setting the mesh into an expanded configuration comprises heat treating the mesh.

Clause 37. The method of any one of the preceding Clauses, wherein creating the at least two slits comprises laser cutting the tubular mesh.

Clause 38. The method any one of the preceding Clauses, wherein the first end portion is a proximal end portion, the second end portion is a distal end portion, and each of the at least two slits extends proximally from a distal terminus of the distal end portion along a longitudinal axis of the device.

Clause 39. The method of any one of the preceding Clauses, wherein each of the at least two slits extends along a longitudinal axis of the device within the intermediate portion.

Clause 40. The method of any one of the preceding Clauses, wherein the arm portion is a first arm portion, the method further comprising forming a second arm portion.

Clause 41. An expandable device delivery system comprising:

an elongated manipulation member configured for advancement within a corporeal lumen, the elongated manipulation member comprising a distal portion, a first proximal portion, and a second proximal portion, the first and second proximal portions being radially spaced apart;

a first pushing element fixed to the first proximal portion of the elongated manipulation member and a second pushing element fixed to the second proximal portion of the elongated manipulation member, wherein each of the first and second pushing elements comprises a distal-facing engagement surface;

an orientation member coupled to the first proximal portion of the elongated manipulation member, the orientation member configured to rotate the first proximal portion of the elongated manipulation member; and an expandable device comprising a distal end portion and two arm portions extending proximally from the distal end portion, wherein each of the two arm portions comprises a proximal edge, wherein the distal-facing engagement surface the first pushing element abuts the proximal edge of the first arm portion and the distal-facing engagement surface of the second pushing element abuts the proximal edge of the second arm portion.

Clause 42. The system of any one of the preceding Clauses, wherein the first and second pushing elements are configured to transmit distally directed force to the expandable device.

Clause 43. The system of any one of the preceding Clauses, further comprising a plate rotatably positioned about the elongated manipulation member.

Clause 44. The system of any one of the preceding Clauses, wherein the plate is configured to transmit proximally directed force or radially outwardly directed force to the expandable device.

Clause 45. The system of any one of the preceding Clauses, further comprising a sheath or catheter, wherein the elongated manipulation member, first and second pushing elements, and the expandable device are located within a lumen of the sheath or catheter.

Clause 46. The system of any one of the preceding Clauses, wherein each of the first and second pushing elements comprises a proximal restraining member.

Clause 47. The system of any one of the preceding Clauses, further comprising a distal restraining member coupled to the elongated manipulation member.

Clause 48. The system of any one of the preceding Clauses, wherein the orientation member is rotatably positioned about the second proximal portion of the elongated manipulation member.

Clause 49. A method of treating an aneurysm positioned between a first blood vessel and a second blood vessel at a blood vessel bifurcation comprising the first blood vessel, the second blood vessel, and a third blood vessel, the method comprising:

providing an expandable device for diverting blood flow away from an aneurysm, the expandable device comprising:

an expandable mesh comprising a plurality of arm portions, the plurality of arm portions including a first arm portion, a second arm portion, and a third arm portion, wherein at least one of the plurality of arm portions is circumferentially discontinuous, the expandable mesh having a generally tubular radially constrained state for advancement through a microcatheter, and an expanded state in which the second arm portion is positioned at a first angle to a longitudinal axis of the first arm portion and the third arm portion is positioned at a second angle to a longitudinal axis of the first arm portion;

advancing the first arm portion of the expandable device into to the first blood vessel and expanding the first arm portion into contact with a wall of the first blood vessel; and advancing the second arm portion into the second blood vessel and expanding the second arm portion into contact with at least a portion of a wall of the second blood vessel; and expanding the third arm portion into contact with at least a portion of a wall of the third blood vessel.

Clause 50. The method of any one of the preceding Clauses, wherein the first arm portion is circumferentially continuous.

Clause 51. The method of any one of the preceding Clauses, wherein the second arm portion is circumferentially discontinuous.

Clause 52. The method of any one of the preceding Clauses, wherein at least a portion of the third arm portion is circumferentially discontinuous.

Clause 53. The method of any one of the preceding Clauses, wherein, when the device is expanded at the blood vessel bifurcation, at least a portion of the second arm portion is positioned across a neck of the aneurysm.

Clause 54. The method of any one of the preceding Clauses, wherein, when the device is expanded at the blood vessel bifurcation, at least a portion of the first arm portion is positioned across a neck of the aneurysm.

Clause 55. The method of any one of the preceding Clauses, wherein, when the device is expanded at the blood vessel bifurcation, at least a portion of the third arm portion is positioned across a neck of the aneurysm.

Clause 56. A system for delivering an expandable device to a treatment site at a blood vessel bifurcation of a patient, the system comprising:
- an elongated shaft having a proximal end portion, a distal end portion configured to be advanced to the treatment site, and a sidewall defining a lumen;
- an expandable device comprising a mesh having a circumferentially continuous first portion, a circumferentially discontinuous second portion coupled to the first portion, and a circumferentially discontinuous third portion coupled to the first portion, the expandable device being configured for (i) advancement through the lumen of the elongated shaft in a constrained configuration in which the first portion is positioned distal of the second portion and the third portion and the second portion extends parallel to the third portion, and (ii) deployment at the treatment site into an expanded configuration such that the first portion is positioned in a first branching blood vessel, the second portion is positioned in a parent blood vessel, and the third portion is positioned in a second branching blood vessel such that the second portion does not extend parallel to the third portion and the mesh extends across a neck of an aneurysm without substantially impeding blood flow from the parent blood vessel into the first and second branching blood vessels; and
- a core assembly carrying the expandable device and configured for advancement through the lumen of the elongated shaft, the core assembly comprising:
  - a first elongated manipulation member configured to engage a proximal region of the second portion of the mesh such that distal movement of the first elongated manipulation member imparts distally directed force to the second portion of the mesh; and
  - a second elongated manipulation member configured to engage a proximal region of the third portion of the mesh such that distal movement of the second elongated manipulation member imparts distally directed force to the third portion of the mesh,
  - wherein the first elongated manipulation member and the second elongated manipulation member are radially spaced apart and configured to slide longitudinally relative to one another.

Clause 57. The system of any one of the preceding Clauses, wherein the first elongated manipulation member carries a proximal restraint positioned proximally of the proximal region of the second portion of the mesh such that distal movement of the first elongated manipulation member causes the proximal restraint to impart distally directed force to the proximal region of the second portion of the mesh.

Clause 58. The system of any one of the preceding Clauses, wherein the first elongated manipulation member carries an engagement member positioned distal of the proximal restraint, and wherein the engagement member is configured to engage the second portion of the mesh so that proximal movement of the first elongated manipulation member causes the engagement member to impart proximally directed force to the second portion of the mesh.

Clause 59. The system of any one of the preceding Clauses, wherein the engagement member comprises a sprocket with two or more radial projections each configured to extend into a pore of the mesh.

Clause 60. The system of any one of the preceding Clauses, wherein the engagement member comprises a cylindrically shaped polymer.

Clause 61. The system of any one of the preceding Clauses, wherein the engagement member is configured to engage the second portion of the mesh while positioned within the lumen of the elongated shaft.

Clause 62. The system of any one of the preceding Clauses, wherein the engagement member applies a radially outward force to the second portion of the mesh and the sidewall of the elongated shaft while positioned within the lumen of the elongated shaft.

Clause 63. The system of any one of the preceding Clauses, wherein the second elongated manipulation member comprises a proximal end portion and a distal end portion, and wherein the distal end portion is releasably secured to the proximal region of the third portion.

Clause 64. The system of any one of the preceding Clauses, wherein the second elongated manipulation member is radially bent between the proximal end portion and the distal end portion.

Clause 65. The system of any one of the preceding Clauses, wherein the second elongated manipulation member is secured to the proximal region of the third portion via an electrolytically corrodible attachment.

Clause 66. The system of any one of the preceding Clauses, wherein the second elongated manipulation member is secured to the proximal region of the third portion via a mechanically separable attachment.

Clause 67. The system of any one of the preceding Clauses, wherein the mesh comprises a plurality of braided filaments.

Clause 68. The system of any one of the preceding Clauses, wherein the mesh is resilient.

Clause 69. The system of any one of the preceding Clauses, wherein the mesh is configured to prevent or limit fluid flow through a sidewall of the mesh.

Clause 70. The system of any one of the preceding Clauses, wherein the mesh has a surface coverage of at least 20%.

Clause 71. The system of any one of the preceding Clauses, wherein the mesh has a surface coverage of at least 30%.

Clause 72. The system of any one of the preceding Clauses, wherein the third portion of the mesh has a length less than a length of the second portion of the mesh.

Clause 73. The system of any one of the preceding Clauses, wherein the second elongated manipulation member carries a proximal restraint positioned proximally of the proximal region of the third portion of the mesh such that distal movement of the second elongated manipulation member causes the proximal restraint to impart distally directed force to the proximal region of the third portion of the mesh.

Clause 74. The system of any one of the preceding Clauses, wherein the elongated shaft is a first elongated shaft, the system further comprising a second elongated shaft having a proximal end portion, a distal end portion configured to be advanced to the treatment site, and a sidewall defining a lumen, and wherein the lumen of the second elongated shaft is configured to slidably receive the first elongated shaft therethrough.

Clause 75. A system for delivering an expandable device to a treatment site at a blood vessel bifurcation of a patient, the system comprising:
- an elongated shaft having a proximal end portion, a distal end portion configured to be advanced to the treatment site, and a sidewall defining a lumen;
- an expandable device comprising a circumferentially continuous first portion, a circumferentially discontinuous second portion coupled to the first portion, and a circumferentially discontinuous third portion coupled to the first portion, the expandable device being configured for (i) advancement through the lumen of the elongated shaft in a constrained configuration in which the first portion is positioned distal of the second portion and the third portion and the second portion extends parallel to the third portion, and (ii) deployment at the treatment site into an expanded configuration such that the first portion is positioned in a first branching blood vessel, the second portion is positioned in a parent blood vessel, and the third portion is positioned in a second branching blood vessel such that the second portion does not extend parallel to the third portion and the device extends across a neck of an aneurysm without substantially impeding blood flow from the parent blood vessel into the first and second branching blood vessels; and an elongated manipulation member carrying the expandable device and configured for advancement through the lumen of the elongated shaft, the elongated manipulation member comprising a proximal end portion, a distal end portion releasably secured to the third portion of the device, and an intermediate portion between the proximal end portion and the distal end portion, the intermediate portion being releasably secured the second portion of the device, wherein the elongated manipulation member is configured to move the second portion of the device relative to the elongated shaft while the intermediate portion of the elongated manipulation member is secured to the second portion, and wherein the elongated manipulation member is configured to move the third portion of the device relative to the elongated shaft while the distal portion of the elongated manipulation member is secured to the third portion, and wherein release of the distal end portion of the elongated manipulation member from the third portion of the device is independent of release of the intermediate portion of the elongated manipulation member from the second portion of the device.

Clause 76. The system of any one of the preceding Clauses, wherein the distal end portion of the elongated manipulation member is secured to the third portion of the device via an electrolytically corrodible attachment.

Clause 77. The system of any one of the preceding Clauses, wherein the elongated manipulation member comprises a radial bend between the intermediate portion and the distal end portion.

Clause 78. The system of any one of the preceding Clauses, wherein the distal end portion of the elongated manipulation member is secured to at least one of an inner surface of the third portion of the device or a proximal end of the third portion of the mesh.

Clause 79. The system of any one of the preceding Clauses, wherein the distal end portion of the elongated manipulation member is secured to a proximal end of the third portion of the device.

Clause 80. A method of delivering an expandable device to a treatment site over a neck of an aneurysm located at bifurcation of a parent blood vessel into a first branching blood vessel and a second branching blood vessel, the method comprising:

advancing a distal end portion of an elongated shaft to the first branching blood vessel;

positioning a coupling assembly carrying an expandable device within a lumen of the elongated shaft in a constrained state at the distal end portion of the elongated shaft, wherein— the expandable device comprises a first portion, a second portion positioned proximally of the first portion in the constrained state, and a third portion positioned proximally of the first portion in the constrained state, wherein each of the second portion and the third portion comprises a first end region coupled to the first portion and a free second end region, and the coupling assembly comprises a first elongated manipulation member engaging the second end region of the second portion of the device and a second elongated manipulation member engaging the second end region of the third portion of the device, expelling the first portion of the expandable device from the distal end portion of the elongated shaft so that the first portion expands into contact with a wall of the first branching blood vessel;

distally advancing the third portion of the device towards the second branching blood vessel by distally advancing at least one of the first elongated manipulation member, the second elongated manipulation member, or the elongated shaft;

expelling the second portion of the device from the distal end portion of the elongated shaft so that the second portion disengages from the first elongated manipulation member and expands into contact with a wall of the parent blood vessel;

positioning the third portion of the device within the second branching blood vessel at an intended position and orientation by moving the second elongated manipulation member; and disengaging the second elongated manipulation member from the third portion of the device such that the third portion of the device expands into contact with a wall of the second branching blood vessel.

Clause 81. The method of any one of the preceding Clauses, wherein expelling the first portion of the expandable device from the distal end portion of the elongated shaft comprises distally advancing the first elongated manipulation member and/or the second elongated manipulation member relative to the elongated shaft.

Clause 82. The method of any one of the preceding Clauses, wherein expelling the first portion of the expandable device from the distal end portion of the elongated shaft comprises proximally retracting the elongated shaft relative to the first elongated manipulation member and/or the second elongated manipulation member relative to the elongated shaft.

Clause 83. The method of any one of the preceding Clauses, wherein expelling the second portion of the device from the distal end portion of the elongated shaft comprises distally advancing the first elongated manipulation member relative to the elongated shaft.

Clause 84. The method of any one of the preceding Clauses, wherein expelling the second portion of the device from the distal end portion of the elongated shaft comprises proximally retracting the elongated shaft relative to the first elongated manipulation member.

Clause 85. The method of any one of the preceding Clauses, further comprising prior to disengaging the second portion of the device from the first elongated manipulation member, retracting the second portion of the device and the first elongated manipulation member proximally into or through the lumen of the elongated shaft.

Clause 86. The method of any one of the preceding Clauses, wherein distally advancing the third portion of the device towards the second branching blood vessel comprises distally advancing the first elongated manipulation member, the second elongated manipulation member, and the second elongated shaft.

Clause 87. The method of any one of the preceding Clauses, wherein the elongated shaft is a first elongated shaft, the method further comprising, before advancing the distal end portion of the first elongated shaft to the first branching blood vessel, advancing a distal end portion of a second elongated shaft to the parent vessel, and wherein the distal end portion of the first elongated shaft is advanced through a lumen of the second elongated shaft.

Clause 88. The method of any one of the preceding Clauses, wherein disengaging the second elongated manipulation member from the third portion of the device comprises delivering an electrical current to the second elongated manipulation member.

Clause 89. The method of any one of the preceding Clauses, wherein distally advancing the expandable device relative to the elongated shaft such that the first portion of the device is expelled from the distal end portion of the elongated shaft comprises proximally retracting the elongated shaft without substantially proximally retracting the expandable device.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

FIG. 4A is an isometric view of an expandable device in a constrained configuration in accordance with embodiments of the present technology.

FIG. 4B is an axial cross-sectional view of the expandable device shown in FIG. 4A taken along line 4B-4B.

FIG. 4C is an axial cross-sectional view of the expandable device shown in FIG. 4A taken along line 4C-4C.

FIGS. 6A and 6B are isometric views of an expandable device in accordance with embodiments of the present technology, shown in a constrained configuration and an expanded configuration, respectively.

FIGS. 10A and 10B show an expandable device in a constrained configuration and an expanded configuration, respectively, in accordance with embodiments of the present technology.

DETAILED DESCRIPTION

I. Definitions

Figure 1A:
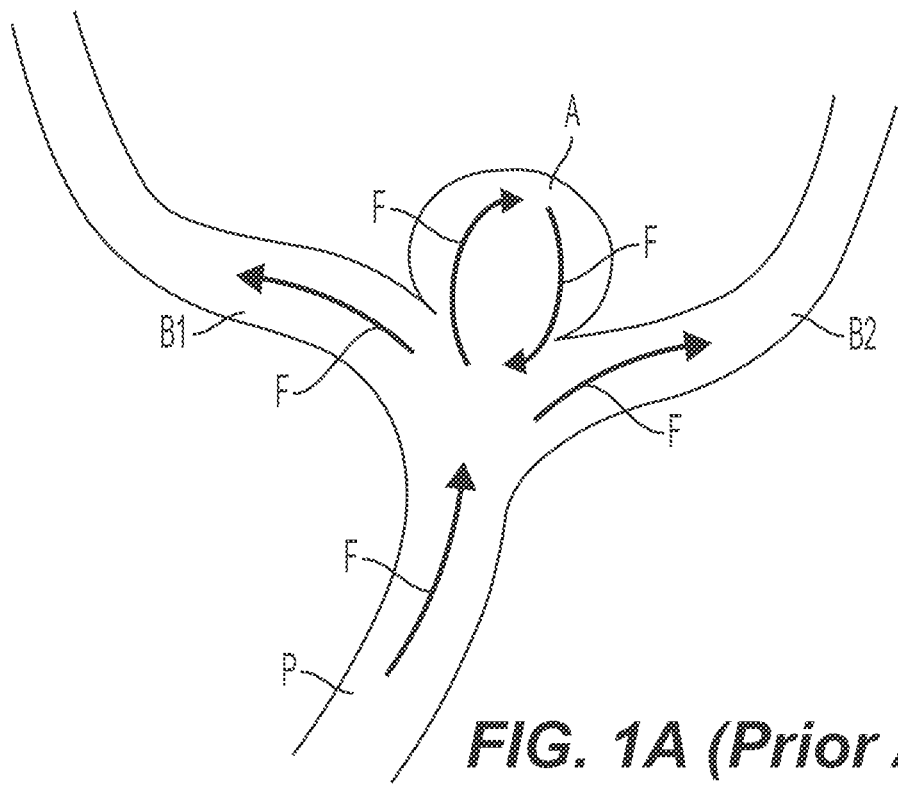
FIG. 1A depicts an example bifurcation aneurysm located between two branching blood vessels at a bifurcation of a parent blood vessel.

The present technology relates to expandable devices and associated systems and methods. Some embodiments of the present technology, for example, are directed to flow-diverting expandable meshes configured to be positioned within one or more blood vessels at a blood vessel bifurcation and across a neck of a bifurcation aneurysm. Specific details of several embodiments of the technology are described below with reference to FIGS. 1A-20G.

Regarding the terms "distal" and "proximal" within this description, unless otherwise specified, the terms can reference a relative position of the portions of an interventional device such as a flow-diverting device and/or an associated delivery device with reference to an operator and/or a location in the vasculature. For example, in referring to a delivery system including the expandable flow-diverting devices described herein, "proximal" can refer to a position closer to the operator of the device or an incision into the vasculature, and "distal" can refer to a position that is more distant from the operator of the device or further from the incision along the vasculature (e.g., the end of the catheter).

As used herein, "constrained configuration" refers to an unexpanded configuration of the expandable device in which the expandable device is configured to be delivered or withdrawn through a catheter to or from a treatment site. As used herein, "expanded configuration" refers to a configuration of the expandable device in which the expandable device is partially or fully expanded. An expanded configuration may be achieved via actuation only (for example, via inflation of a balloon), via self-expansion only, or both. Unless provided otherwise herein, "fully expanded," as used to describe a configuration of the expandable device, refers to a configuration of the expandable device in which each of the specific portions of the expandable device is positioned and oriented relative to the other portions of the expandable device as desired for treatment. For example, in a fully expanded configuration, an expandable device of the present technology may comprise a circumferentially discontinuous articulating portion positioned at an angle to a tubular body portion reflecting an angle between two blood vessels at a bifurcation. As used herein, "intermediate expanded configuration" refers to a configuration of the expandable device in between the constrained configuration and the fully expanded configuration.

As used herein, the term "longitudinal" refers to a direction along an axis that extends through the lumen of the expandable device while in a constrained configuration and the term "circumferential" can refer to a direction within a plane that is orthogonal to the longitudinal axis and extends around the circumference of the device when in a tubular configuration. As used herein, "circumferentially continuous" can refer to a portion of the device that has a closed circumference such that an axial cross-sectional shape of the device is at least one complete circle. As used herein, "circumferentially discontinuous" can refer to a portion of the device that has an open circumference such that an axial cross-sectional shape of the device is an arc that subtends an angle less than 360 degrees.

As used herein, "vessel bifurcation" refers to a location at which a parent blood vessel branches into two or more branching blood vessels. A bifurcation aneurysm refers to an aneurysm positioned between two branching blood vessels or between a parent blood vessel and a branching blood vessel.

As used herein, the terms "generally," "substantially," "about," and similar terms are used as terms of approximation and not as terms of degree, and are intended to account for the inherent variations in measured or calculated values that would be recognized by those of ordinary skill in the art.

II. Expandable Devices

Expandable devices of the present technology may be configured to treat bifurcation aneurysms located at a vessel bifurcation in a patient's vasculature. As shown in FIG. 1A, a vessel bifurcation can comprise a region of a patient's vasculature at which a parent blood vessel P splits into two or more branching blood vessels B1, B2. A bifurcation aneurysm A, can be located between the branching blood vessels B1, B2 (see FIG. 1A, for example) or between the parent blood vessel P and one of the branching blood vessels B1, B2. Compared to the bifurcation depicted in FIG. 1A, the branching blood vessels B1, B2 may be at substantially different angles, have substantially different sizes, and/or be a different quantity (e.g., three or more). The aneurysm A may be offset with respect to the junction (e.g., having a neck substantially open to one branching vessel), tilted with respect to a plane created by the vessels (e.g., into or out of the page), etc. Devices of the present technology can be configured for treating bifurcation aneurysms in any vasculature of a patient including, for example, a cerebral artery, a peripheral artery, a coronary artery, a pulmonary artery, an abdominal artery, a thoracic artery, an aortic artery, etc. As shown in FIG. 1A, fluid flows (represented by arrows F) from the parent vessel P into the branching vessels B1, B2. Moreover, when an aneurysm A is present, fluid flows into the aneurysm A, which can cause the aneurysm A to rupture, leading to stroke, death, disability, etc. Consequently, it may be advantageous to treat the aneurysm A by reducing blood flow into the aneurysm A and, thereby, reducing the risk of adverse outcomes associated with fluid flow into the aneurysm A.

Figure 1B:
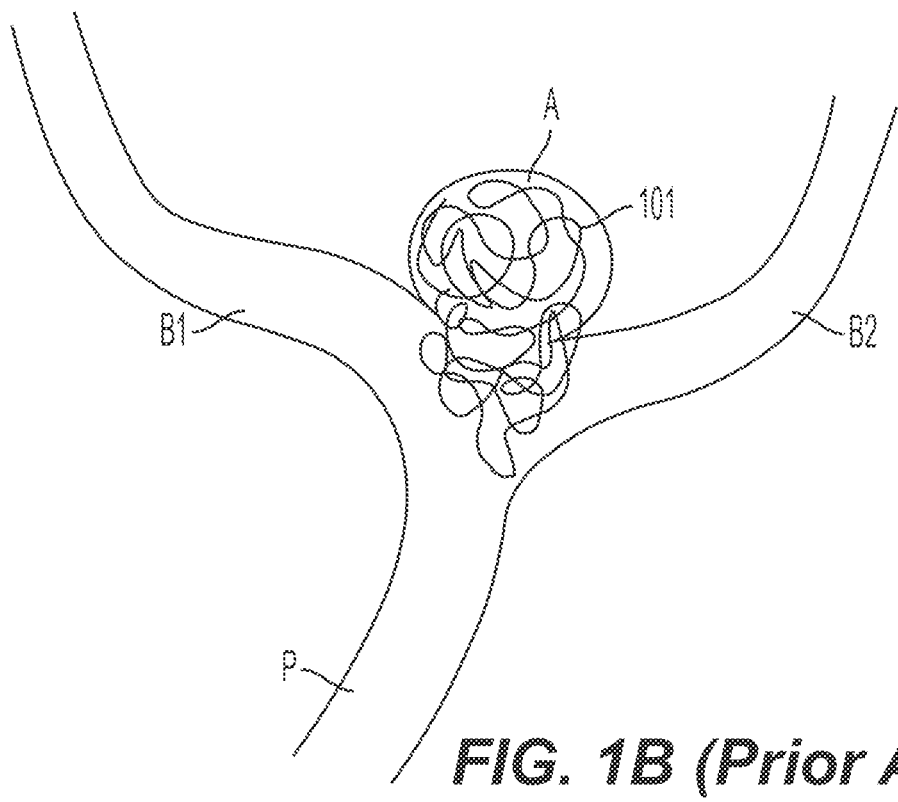
FIG. 1B depicts coil herniation from the example bifurcation aneurysm of FIG. 1A.

Intrasaccular occlusive devices such as, but not limited to, embolization coils 101 (see FIG. 1B, for example) may be used to treat the aneurysm A. Such coils 101 can be positioned within the aneurysm A to limit blood flow into the aneurysm A and promote thrombosis formation in the aneurysm A, which can cause occlusion and healing of the aneurysm A. However, if the aneurysm A has a wide neck, the aneurysm A may be difficult to treat with an intrasaccular device (e.g., embolization coils 101) alone because the intrasaccular device may be prone to relocating through the neck of the aneurysm A and into the parent vessel P, for example as illustrated in FIG. 1B. Relocation or herniation of the coils 101 may cause arterial occlusion, stroke, and/or death. Flow-diverting devices may be used alone or in conjunction with intrasaccular devices to prevent blood flow into the aneurysm. However, tubular flow-diversion devices may insufficiently cover the neck of the aneurysm and/or undesirably block blood flow into one of the vessels at the bifurcation. To address these challenges, devices of the present technology comprise flow-diverting devices configured be positioned across a neck of a bifurcation aneurysm to prevent or limit blood flow into the aneurysm without substantially blocking blood flow from a parent vessel into two or more branching vessels.

Figure 2B:
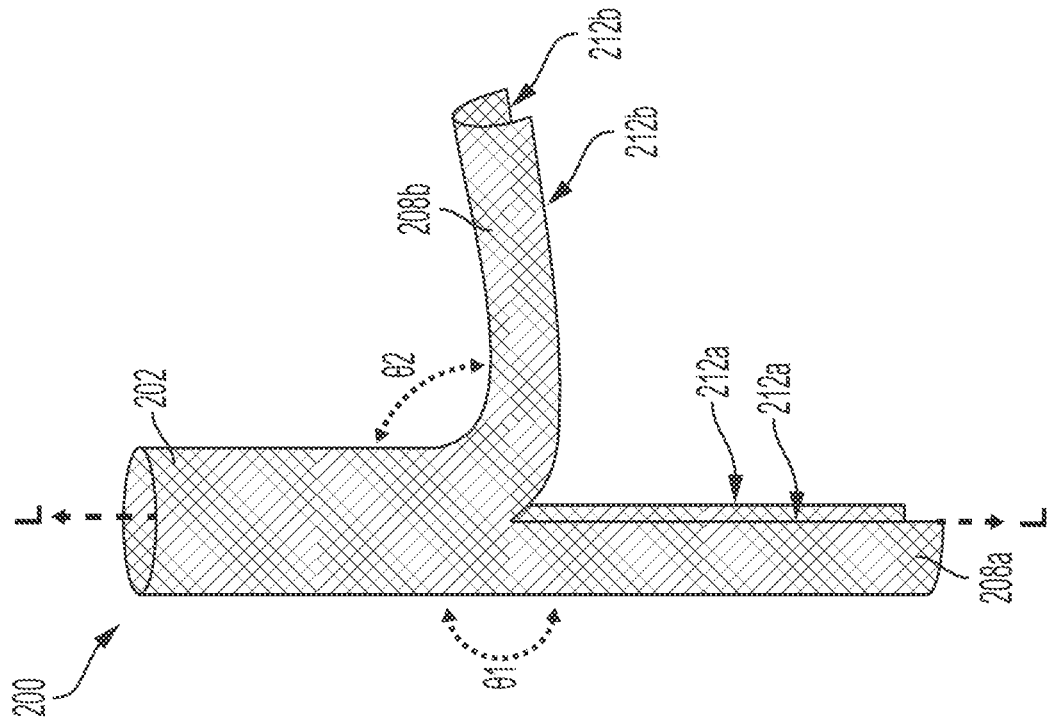
FIG. 2B is an isometric view of the expandable device shown in FIG. 2A in an expanded configuration in accordance with embodiments of the present technology.
Figure 2A:
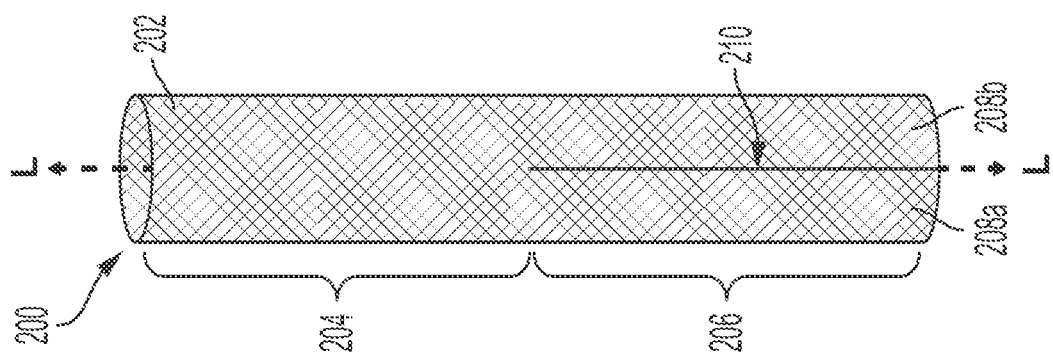
FIG. 2A is an isometric view of an expandable device in a constrained configuration in accordance with embodiments of the present technology.

FIGS. 2A and 2B are isometric views of an expandable, flow-diverting device 200 (also "device 200") in accordance with the present technology. The device 200 is configured to be intravascularly delivered in a constrained configuration (e.g., through a catheter) to a treatment site comprising a blood vessel bifurcation. FIG. 2A shows the device 200 in the constrained configuration. The device 200 can be configured to be deployed in an expanded configuration at the treatment site. FIG. 2B shows the device 200 in the expanded configuration. In the constrained configuration, the device 200 can be substantially tubular in shape to facilitate its delivery through a catheter. In the expanded configuration, the device 200 can have at least two portions angled with respect to one another to at least partially reflect the geometry of the treatment site. One of the portions can be circumferentially discontinuous so that, when the device 200 is deployed at the treatment site and positioned across a juncture between at least two blood vessels, blood flow through the vessels at the treatment site is not substantially impeded by the device 200.

The device 200 can comprise an expandable, flow-diverting mesh ("mesh 202") configured to interfere with blood flow to a degree sufficient to lead to thrombosis of the aneurysm. For example, the mesh 202 may have a sufficiently low porosity and/or a sufficiently high surface coverage to prevent or reduce blood flow across a thickness of the mesh 202. Specific details relating to such parameters of the mesh 202 are disclosed below. In some embodiments, the mesh 202 comprises a plurality of strands that are braided or woven. In various embodiments, the mesh 202 comprises a laser-cut stent. Although FIGS. 2A and 2B depict the device 200 comprising a single mesh 202, in some embodiments, the device 200 comprises multiple occlusive devices (e.g., stents, braids, etc.). A second occlusive device can be positioned radially within the mesh 202, radially over the mesh 202, across the mesh 202, and/or end-to-end with the mesh 202. For example, any expandable device of the present technology may comprise a first tubular mesh positioned radially within a second tubular mesh such that the device comprises a combined porosity that is less than a porosity of either the first or second meshes alone. In some embodiments, a device of the present technology device can comprise a mesh configured to divert blood flow and a stent configured to provide structural support for the mesh. Additional occlusive devices can be formed integrally with or independently of the mesh 202.

According to some embodiments, for example as shown in FIG. 2A, the mesh 202 comprises an entire length and/or circumference of the device. However, the mesh 202 may comprise only a portion of the length and/or circumference of the device 200, for example, when combined with a second occlusive device. In some embodiments, a length of the mesh 202 is based at least in part on a length of an aneurysm neck to be treated and/or a geometry of the blood vessels at the bifurcation. In some embodiments, one or more parameters of the mesh 202 (e.g., porosity, surface coverage, diameter, thickness, material properties, etc.) can be constant throughout the entire device 200. However, one or more parameters of the mesh 202 may also or alternatively vary throughout the device 200. For example, an expandable device of the present technology may comprise one portion configured to be positioned at least partially over a neck of the aneurysm and comprising a low porosity mesh so that the portion is configured to prevent blood flow into the aneurysm. Such a device may also comprise one or more portions configured to anchor to a vessel wall. Such anchoring portions may have a lower surface coverage and porosity and/or a greater radial outward force than the flow-diverting portion to facilitate anchorage to the vessel wall.

FIG. 2A shows the device 200 in a constrained state configured for delivery through a lumen of a catheter to a treatment site. In the constrained state, the device 200 can have a generally tubular shape. The device 200 can comprise a first portion 204, a second portion 206, and a longitudinal axis L extending between the first and second portions 204, 206. In some embodiments, the first portion 204 is a distal end portion and the second portion 206 is a proximal end portion. For example, the first portion 204 can be configured to be positioned distally of the second portion 206 while advancing the device 200 through a catheter and/or when implanted in a patient's vasculature. In some embodiments, the first portion 204 comprises a body portion of the device 200 while the second portion 206 includes one or more articulating portions of the device 200. The device 200 may comprise an outer surface, an inner surface, a thickness between the inner and outer surfaces, and a lumen defined by the inner surface and extending from the first portion 204 to the second portion 206. One or more ends of the device 200 may be open (e.g., the lumen extends through the end(s) of the device 200).

According to some embodiments, a diameter and/or a length of the first portion 204 of the device 200 in the constrained configuration can be based at least in part on anatomy to be treated. For example, in some cases it may be beneficial to select a diameter of the first portion 204 of the device 200 to be slightly greater than a diameter of the vessel the first portion 204 is configured to be positioned within. Oversizing the diameter of the first portion 204 may promote anchoring of the first portion 204 to the vessel wall. In some embodiments, the diameter of the device 200 varies along a length of the device 200. For example, the first portion 204 and/or the second portion 206 can radially taper in a distal direction or a proximal direction. Alternatively, or in addition, the first portion 204 and/or the second portion 206 may radially flare in a distal direction or a proximal direction. In some embodiments, the diameter of the device 200 is generally constant along a length of the device 200. According to some embodiments, a length of the device 200 can be configured based on a length of a parent vessel, a length of a branching vessel, an angle between two vessels, a length of an aneurysm neck, etc. In the constrained configuration, the device 200 can have a substantially tubular shape (see FIG. 2A, for example). In some embodiments, the device 200 does not comprise a tubular shape in the constrained state. The device 200 can comprise any suitable hollow shape including, but not limited to, round, ovular, elliptical, rectangular, prismatic, irregular, etc.

According to some embodiments, the second portion 206 of the mesh 202 can comprise one or more articulating portions 208 movable relative to the first portion 204 of the mesh 202. For example, as shown in FIG. 2A, the second portion 206 of the mesh 202 can comprise circumferentially discontinuous first and second articulating portions 208a, 208b. The articulating portions 208 may be separated by one or more slits 210. For example, the articulating portions 208 can be separated by two longitudinally extending slits 210. According to some embodiments, the number of articulating portions 208 is directly proportional to the number of slits 210. For example, two slits 210 can form two articulating portions 208, three slits 210 can form three articulating portions 208, four slits 210 can form four articulating portions 208, etc. In some embodiments, the number of slits 210 is greater or less than the number of articulating portions 208.

In some embodiments, for example as depicted in FIG. 2A, the slits 210 extend along a longitudinal axis L of the device 200. The slits 210 may also extend along a circumference of the device and/or along a direction oblique to such longitudinal and/or circumferential directions. Each of the slits 210 can have a first end, a second end, and a length therebetween. The first and/or second ends of one of the slits 210 can be generally longitudinally aligned with the first and/or second ends of the other slit(s), respectively. In some embodiments, the first ends of the slits 210 are longitudinally offset. In some embodiments, the second ends of the slits 210 are longitudinally offset. The slits 210 may comprise the same length. In some embodiments, one of the slits 210 has a length different from or the same as a length of another of the slits 210. As shown in FIGS. 2A and 2B, in some embodiments, the slits 210 extend through a terminus of the device 200. The slits may extend through one, both, or none of the termini of the device 200.

Each articulating portion 208 can have edges 212. For example, as shown in FIG. 2B, the first articulating portion 208a can have first edges 212a and the second articulating portion 208b can have second edges 212b. One of the first edges 212a can be separated from a corresponding one of the second edges 212b by at least one slit 210. For example, one of the slits 210 can have a width that defines an opening between one of the first edges 212a and a corresponding one of the second edges 212b adjacent to the slit 210. In some embodiments, for example as shown in FIG. 2A, the slit width is negligible such that adjacent first and second edges 212a, 212b are disconnected from one another but in contact with one another when the device 200 is in the constrained configuration. The slit width can be greater than zero such that adjacent first and second edges 212a, 212b are disconnected and spaced apart by at least the width of the slit 210 when the device 200 is in the constrained configuration.

According to some embodiments, a device of the present technology can be configured to assume an expanded state in which articulating portions of the device are angled relative to a body portion of the device. For example, FIG. 2B depicts the device 200 in an expanded configuration. In the expanded configuration, the first articulating portion 208a and the second articulating portion 208b can diverge away from one another and/or can be angled relative to the first portion 204.

The first articulating portion 208a (e.g., a longitudinal axis of the first articulating portion 208a) may be positioned at a first angle θ1 to a longitudinal axis L of the device 200 (e.g., as defined by the first portion 204). As shown in FIG. 2B, the first angle θ1 may be approximately zero such that the first articulating portion 208a is generally parallel to the longitudinal axis L. In some embodiments, the first angle θ1 is substantially non-zero such that the first articulating portion 208a is not generally parallel with the first portion 204. The first angle θ1 may be between about 10 degrees and about 170 degrees, between about 20 degrees and about 160 degrees, between about 30 degrees and about 150 degrees, between about 40 degrees and about 140 degrees, between about 50 degrees and about 130 degrees, between about 60 degrees and about 120 degrees, between about 70 degrees and about 110 degrees, between about 80 degrees and about 100 degrees, about 90 degrees, more than 90 degrees, or less than 90 degrees.

The second articulating portion 208b may be positioned at a second angle θ2 to the longitudinal axis L of the device 200. In some embodiments, the second angle θ2 is between about 10 degrees and about 170 degrees, between about 20 degrees and about 160 degrees, between about 30 degrees and about 150 degrees, between about 40 degrees and about 140 degrees, between about 50 degrees and about 130 degrees, between about 60 degrees and about 120 degrees, between about 70 degrees and about 110 degrees, between about 80 degrees and about 100 degrees, about 90 degrees, more than 90 degrees, or less than 90 degrees. According to some embodiments, the first angle θ1 and/or the second angle θ2 is between about 60 degrees and about 120 degrees. The first angle θ1 can be substantially the same as the second angle θ2 or can be different from the second angle θ2. As discussed in greater detail below, the first angle θ1 and/or the second angle θ2 can be based, at least in part, on a blood vessel bifurcation to be treated (e.g., based at least in part on angles between branch vessels, based at least in part on angles between a branch vessel and a parent vessel, etc.).

Figure 3:
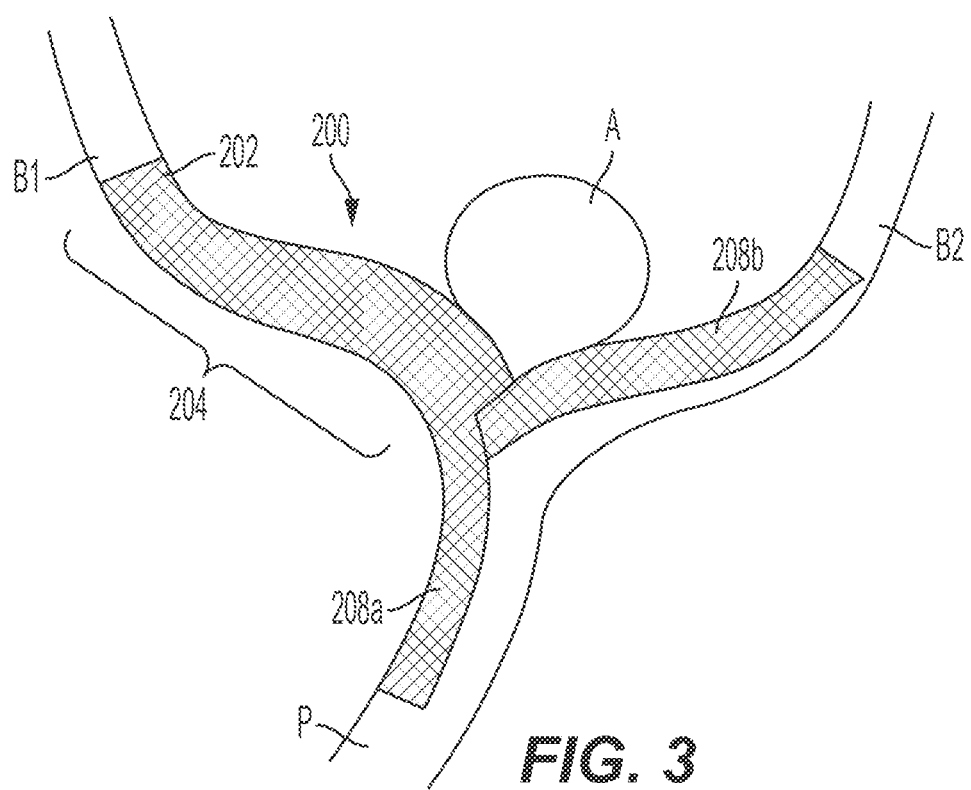
FIG. 3 shows an expandable device in an expanded configuration and positioned at a blood vessel bifurcation in accordance with embodiments of the present technology.

Each of the first portion 204, first articulating portion 208a, and second articulating portion 208b may be configured to be positioned within a lumen of a blood vessel at a bifurcation aneurysm treatment site, as shown in FIG. 3 for example. The first portion 204 can be configured to be positioned within a lumen of the first branching blood vessel B1. The device 200 can be deployed into a fully expanded configuration (FIG. 3) in which the second articulating portion 208b is positioned and expanded within the second branching blood vessel B2 and the first articulating portion 208a is positioned and expanded within the parent blood vessel P. As shown in FIG. 3, the first portion 204 and/or the second articulating portion 208b can be configured to be positioned across the neck of the aneurysm A. The flow-diverting properties these portions of the mesh 202 can be configured to block blood flow into the aneurysm. In some embodiments, any single portion of the device 200 or multiple portions of the device 200 can be configured to be positioned across the neck of the aneurysm.

One or more portions of the device 200 (e.g., first portion 204, first articulating portion 208a, second articulating portion 208b, etc.) can be configured to anchor to a wall of a blood vessel. The extent of anchorage of a portion of the device 200 with a vessel wall can be based at least in part on a surface coverage of the portion of the device 200 contacting the vessel wall, a radial force exerted on the vessel wall by the portion of the device 200 (e.g., a chronic outward force), a diameter of the portion of the device 200 relative to a diameter of the vessel, a material property of the portion of the device 200, etc. For example, the tubular first portion 204 may have a complete circumference such that the first portion 204 is configured to contact all or most of a circumference of the wall of the first branching blood vessel B1. In contrast, the circumferentially discontinuous second articulating portion 208b may have an incomplete circumference such that the second articulating portion 208b contacts only a portion of the circumference of the wall of the second branching blood vessel B2. Therefore, the second articulating portion 208b may anchor to the second branching blood vessel B2 to a lesser extent than the first portion 204 anchors to the first branching blood vessel B1. While expandable devices of the present technology can be configured to engage and anchor to vessel wall(s), the expandable device 200 (and other expandable devices disclosed herein) can be configured to impart a lower chronic outward force to the vessel wall(s) than other types of expandable devices configured for use in different applications. For example, laser cut stents used in coronary or peripheral vascular applications for maintaining patency of a previously occluded vessel can be configured to impart high chronic outward force to the vessel wall to maintain the structural integrity of a large vessel. In contrast, expandable devices of the present technology that are configured to prevent blood flow into a cerebral aneurysm may not be designed to maintain the patency of a vessel lumen, and thus can be configured to impart lower chronic outward force to the vessel wall.

One or more portions of a device of the present technology can be circumferentially discontinuous so that the one or more portions do not substantially disrupt blood flow from a parent vessel to branching blood vessels. Such circumferentially discontinuous portions can be configured to anchor to a blood vessel wall and/or extend across a neck of an aneurysm to prevent or limit blood flow across the device and into the aneurysm. Each of the circumferentially discontinuous portions can have a width defined by the angle that the portion subtends, which may be based on radial spacing of the slits separating adjacent articulating portions, and/or a radius of curvature of the portion. FIG. 4A depicts a device 400 in a constrained configuration, the device 400 comprising a mesh 402 including a first portion 404 and a second portion 406 continuous with the first portion 404 along a longitudinal axis L of the device 400. According to various embodiments, in the constrained configuration the device 400 has a substantially tubular shape. FIG. 4B shows an axial cross-sectional view of the first portion 404 of the mesh 402 taken along line 4B-4B and FIG. 4C shows an axial cross-sectional view of the second portion 406 of the mesh 402 taken along line 4C-4C. As shown in FIG. 4B, an axial cross-sectional shape of the circumferentially continuous first portion 404 is a complete circle.

According to various embodiments, the second portion 406 can include first and second articulating portions 408a, 408b separated by first and second slits 410a, 401b each extending along the longitudinal axis L of the device 400. As shown in FIG. 4C, the circumferentially discontinuous first and second articulating portions 408a, 408b can each have an axial cross-sectional shape of an arc that subtends an angle. For example, as shown in FIG. 4C, the first articulating portion 408a subtends a first angle φ1 and the second articulating portion 408b subtends a second angle φ2. The first and second slits 410a, 410b are spaced apart by about 180 degrees, therefore, both φ1 and φ2 are equal to about 180 degrees and the first and second articulating portions 408a, 408b comprise approximately equivalent widths (and subtended angles).

Figure 5B:
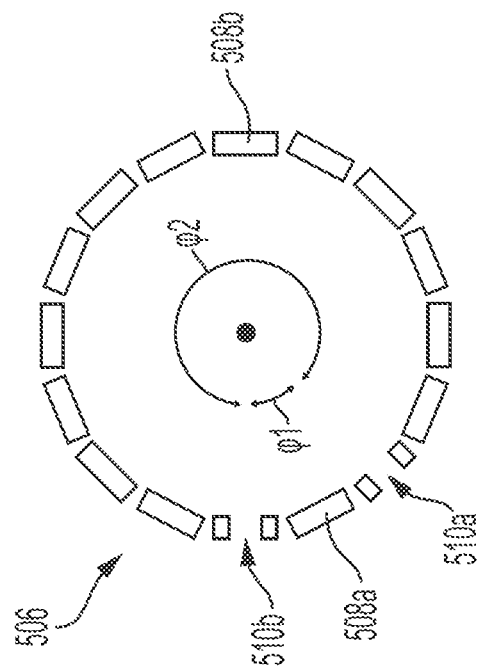
FIG. 5B is an axial cross-sectional view of the expandable device shown in FIG. 5A taken along line 5B-5B.
Figure 5A:
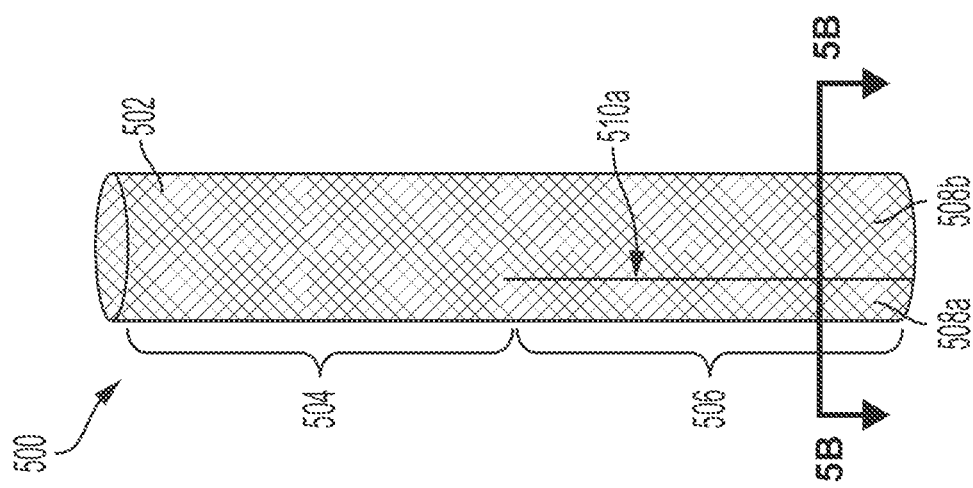
FIG. 5A is an isometric view of an expandable device in a constrained configuration in accordance with embodiments of the present technology.

In some embodiments, the articulating portions of a mesh subtend different angles and comprise different widths. For example, FIGS. 5A and 5B show isometric and axial cross-sectional views, respectively, of a device 500 comprising a mesh 502 including a first portion 504 and a second portion 506 with a first articulating portion 508a subtending a first angle φ1 and a second articulating portion 508b subtending a second angle φ2 that is greater than the first angle φ1. In some embodiments, the magnitudes of the first and second angles φ1 and φ2 can be based on a radial spacing of a first slit 510a to a second slit 510b. In embodiments in which a device comprises more than two articulating portions, some or all of the articulating portions may comprise the same width. In some embodiments, some or all of the articulating portions may comprise different widths. A width of an articulating portion may be selected based on an intended position of the articulating portion at a treatment site. For example, in some embodiments it may be advantageous for an articulating portion configured to be positioned at least partially across an aneurysm neck to have a larger width to ensure or facilitate complete coverage of the aneurysm neck. Additionally or alternatively, as discussed in greater detail below, a width and/or a radial dimension of an articulating portion can be based at least in part on a diameter of one or more vessels to be treated.

An expandable device in accordance with the present technology can have any suitable number of articulating portions. For example, the device 600 depicted in FIGS. 6A and 6B comprises a mesh 602 including a tubular first portion 604 and a second portion 606 longitudinally offset from the first portion 604 and comprising one articulating portion 608 extending away from the first portion 604. The circumferentially discontinuous articulating portion 608 can subtend any suitable angle, as previously described. In some embodiments, the articulating portion 608 subtends an angle of about 180 degrees to form a half tubular shape, as shown in FIGS. 6A and 6B. According to some embodiments, the articulating portion 608 subtends an angle between about 10 degrees and about 350 degrees, between about 20 degrees and about 340 degrees, between about 20 degrees and about 330 degrees, between about 30 degrees and about 320 degrees, between about 40 degrees and about 310 degrees, between about 50 degrees and about 300 degrees, between about 60 degrees and about 290 degrees, between about 70 degrees and about 280 degrees, between about 80 degrees and about 270 degrees, between about 90 degrees and about 260 degrees, between about 100 degrees and about 250 degrees, between about 110 degrees and about 240 degrees, between about 120 degrees and about 230 degrees, between about 130 degrees and about 220 degrees, between about 140 degrees and about 210 degrees, between about 150 degrees and about 200 degrees, or between about 160 degrees and about 190 degrees.

When the device 600 is in the constrained state, for example as shown in FIG. 6A, a longitudinal axis L1 of the articulating portion 608 may be generally parallel to a longitudinal axis L2 of the first portion 604, which can facilitate movement of the device 600 through a lumen of an elongated shaft, such as a catheter. In the expanded state, the articulating portion 608 may be configured such that the longitudinal axis L1 of the articulating portion 608 is positioned at an angle θ (e.g., similar to the first angles θ1 and/or the second angles θ2 disclosed herein) relative to the longitudinal axis L2 of the first portion 604. According to some embodiments, the device 600 may be configured to be positioned at a treatment site across an aneurysm between branching vessels, between a parent vessel and a first branching vessel, and/or between a parent vessel and a second branching vessel. The angle θ between the longitudinal axis L2 of the first portion 604 and the longitudinal axis L1 of the articulating portion 608 may be based in part on the treatment site within which the device 600 is configured to be positioned. For example, the first portion 604 may be configured to be positioned within a first branching vessel and the articulating portion 608 may be configured to be positioned within a second branching vessel and the angle θ may be based on an angle between the first and second branching vessels. In some embodiments, the angle θ is between about 30 degrees and about 150 degrees. According to some embodiments, the angle θ is between about 60 degrees and about 120 degrees, between about 90 degrees and about 120 degrees, between about 60 degrees and about 90 degrees, more than 90 degrees, less than 90 degrees, etc.

Figure 7B:
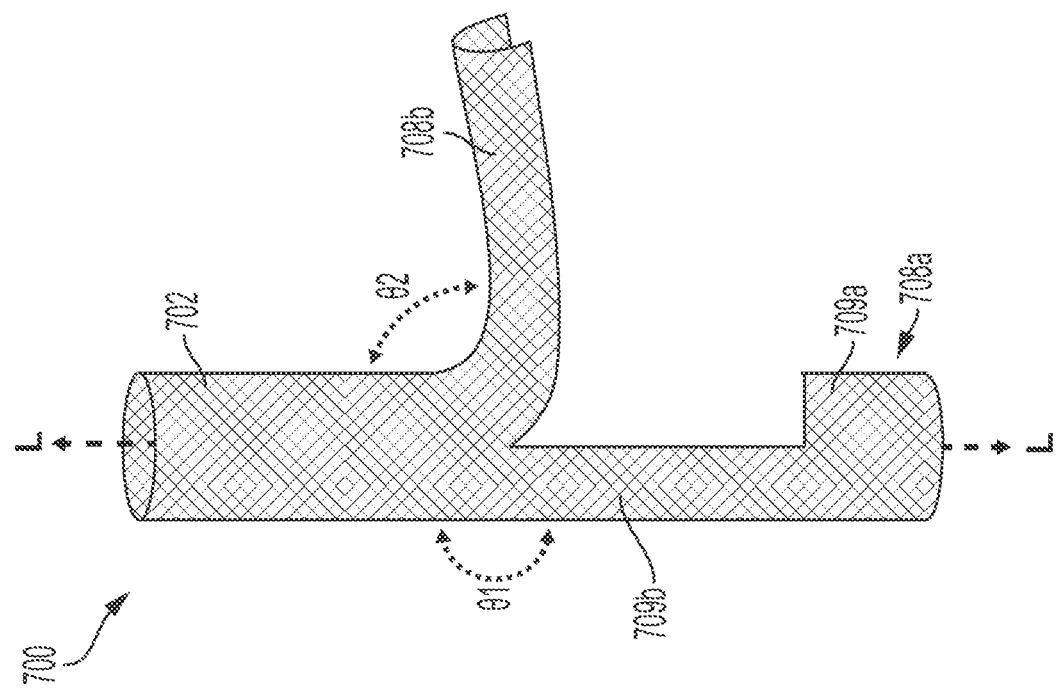
FIGS. 7A and 7B are isometric views of an expandable device in accordance with embodiments of the present technology, shown in a constrained configuration and an expanded configuration, respectively.
Figure 7A:
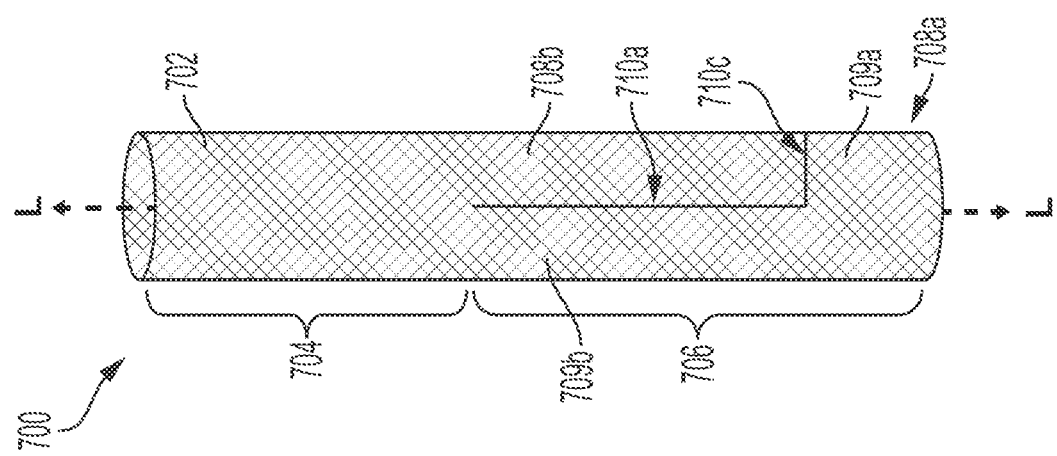

According to some embodiments, for example as shown in FIG. 7A, a device 700 of the present technology can comprise a mesh 702 having a tubular first portion 704 and a second portion 706 extending away from the first portion 704 and comprising a first articulating portion 708a and a second articulating portion 708b. The first articulating portion 708a can comprise a circumferentially continuous region 709a, as well as a circumferentially discontinuous region 709b. In some embodiments, the first portion 704 is a distal portion configured to be positioned within a first branching blood vessel at a treatment site and the circumferentially continuous region 709a of the first articulating portion 708a is a proximal portion configured to be positioned within a parent blood vessel. Additionally or alternatively, the circumferentially discontinuous region 709b of the first articulating portion 708b is configured to be positioned at a juncture between the parent blood vessel and the first branching blood vessel. Because this region 709b is circumferentially discontinuous, it can substantially conform to a portion of the vessel wall at this juncture without extending over an opening to a second branching blood vessel.

The second articulating portion 708b may comprise three edges that are disconnected from the first articulating portion 708a by three slits 710. A first slit 710a (shown in FIG. 7A) and a second slit (not shown in FIG. 7A) can extend longitudinally and a third slit 710c can extend circumferentially between the first slit 710a and the second slit. The first slit 710a and the second slit may extend only partially along the second portion 706 and do not extend through a terminus of the device 700. The second articulating portion 708b can subtend an angle of about 180 degrees, as shown in FIGS. 7A and 7B. In some embodiments, the second articulating portion 708b can subtend an angle between about 10 degrees and about 350 degrees, or other suitable angles such as those described herein. In the expanded configuration (see FIG. 7B, for example), the first articulating portion 708a can be generally parallel to the first portion 704 or can be angled relative to the first portion 704 by a non-zero first angle θ1. The second articulating portion 708b may be positioned at a second angle θ2 relative to the first portion 704 in the expanded configuration. As previously described, the first angle θ1 and/or the second angle θ2 may be between about 30 degrees and about 150 degrees. According to some embodiments, the second angle θ2 is between about 60 degrees and about 120 degrees, between about 90 degrees and about 120 degrees, between about 60 degrees and about 90 degrees, more than 90 degrees, less than 90 degrees, etc.

Figure 8:
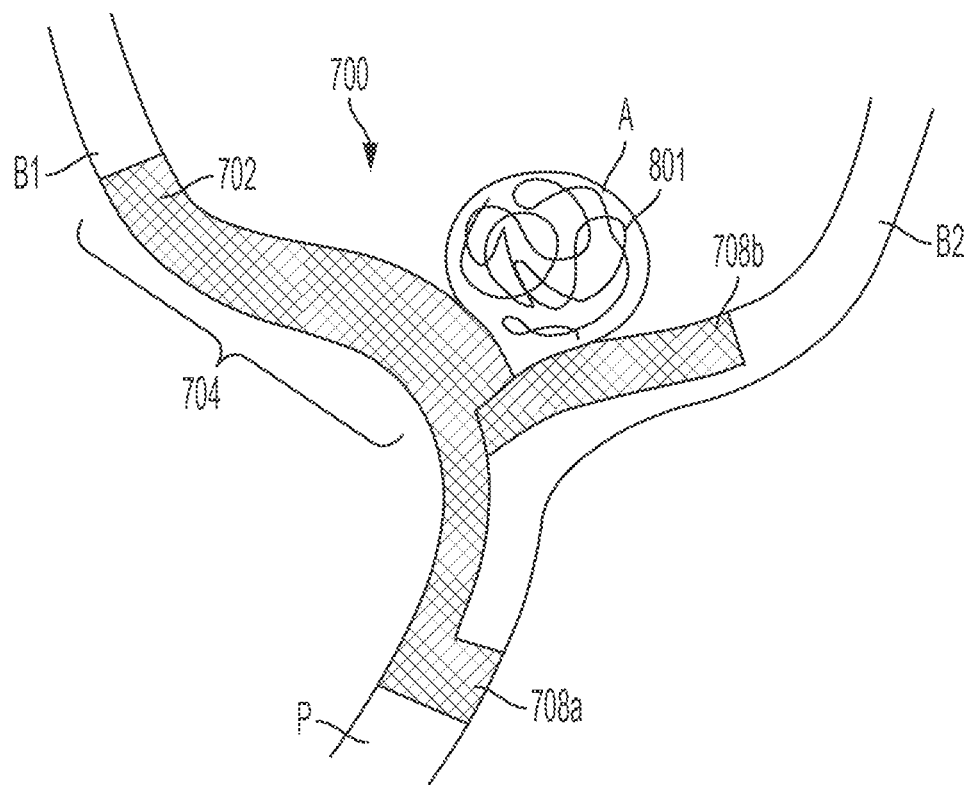
FIG. 8 shows an expandable device in an expanded configuration and positioned at a blood vessel bifurcation in accordance with embodiments of the present technology and an example intrasaccular occlusive device positioned within an aneurysm.

According to some embodiments, for example as shown in FIG. 8, an expandable, flow-diverting device of the present technology, such as device 700, may be used with additional occlusive devices to treat the aneurysm A. Embolic elements 801 may be placed within the aneurysm A prior to deployment of the device 700 at the treatment site. In the expanded configuration, at least one portion of the device 700 (e.g., first portion 704 and/or second articulating portion 708b, etc.) is configured to be positioned across the neck of the aneurysm A. The portion(s) of the device 700 covering the neck of the aneurysm may prevent the embolic elements 801 from prolapsing out of the aneurysm A and into the branching and/or parent blood vessels. The embolic element may be any suitable occlusive device such as embolic coils, liquid embolics, braids, meshes, combinations thereof, etc.

Figure 9A:
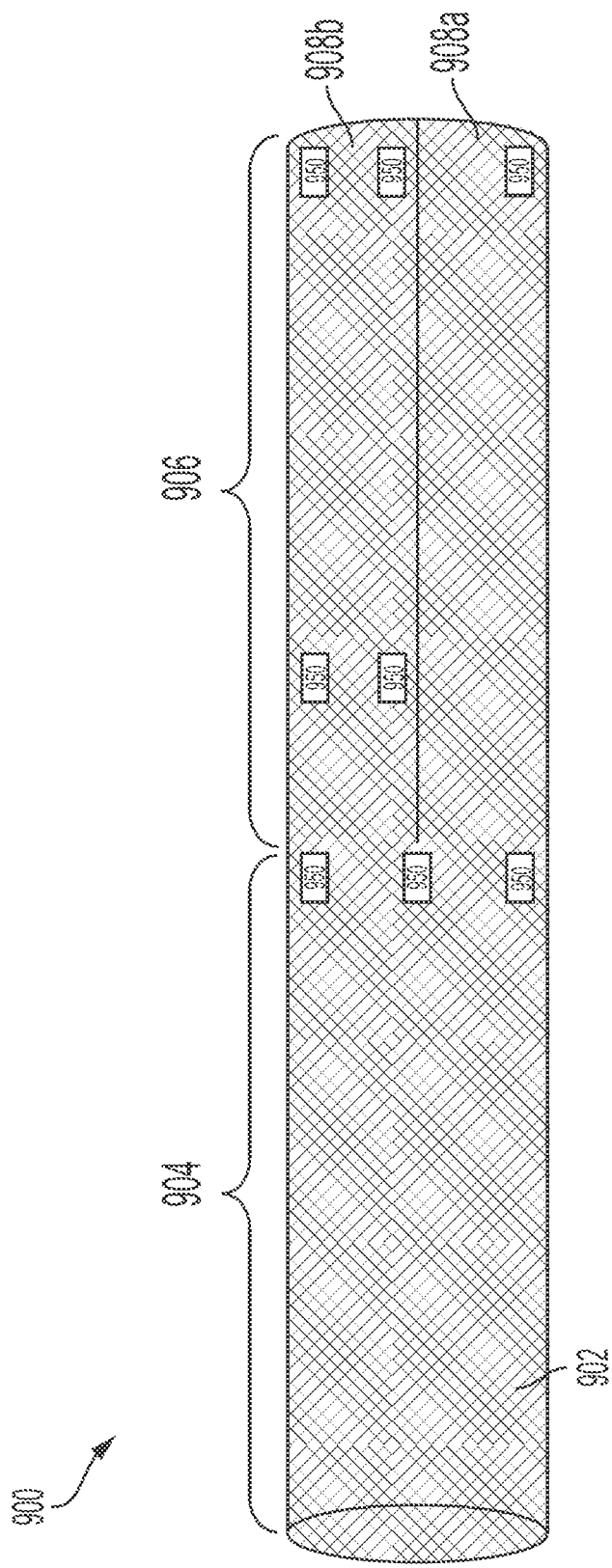
FIG. 9A is an isometric view of an expandable device shown in a constrained configuration in accordance with embodiments of the present technology.
Figure 9B:
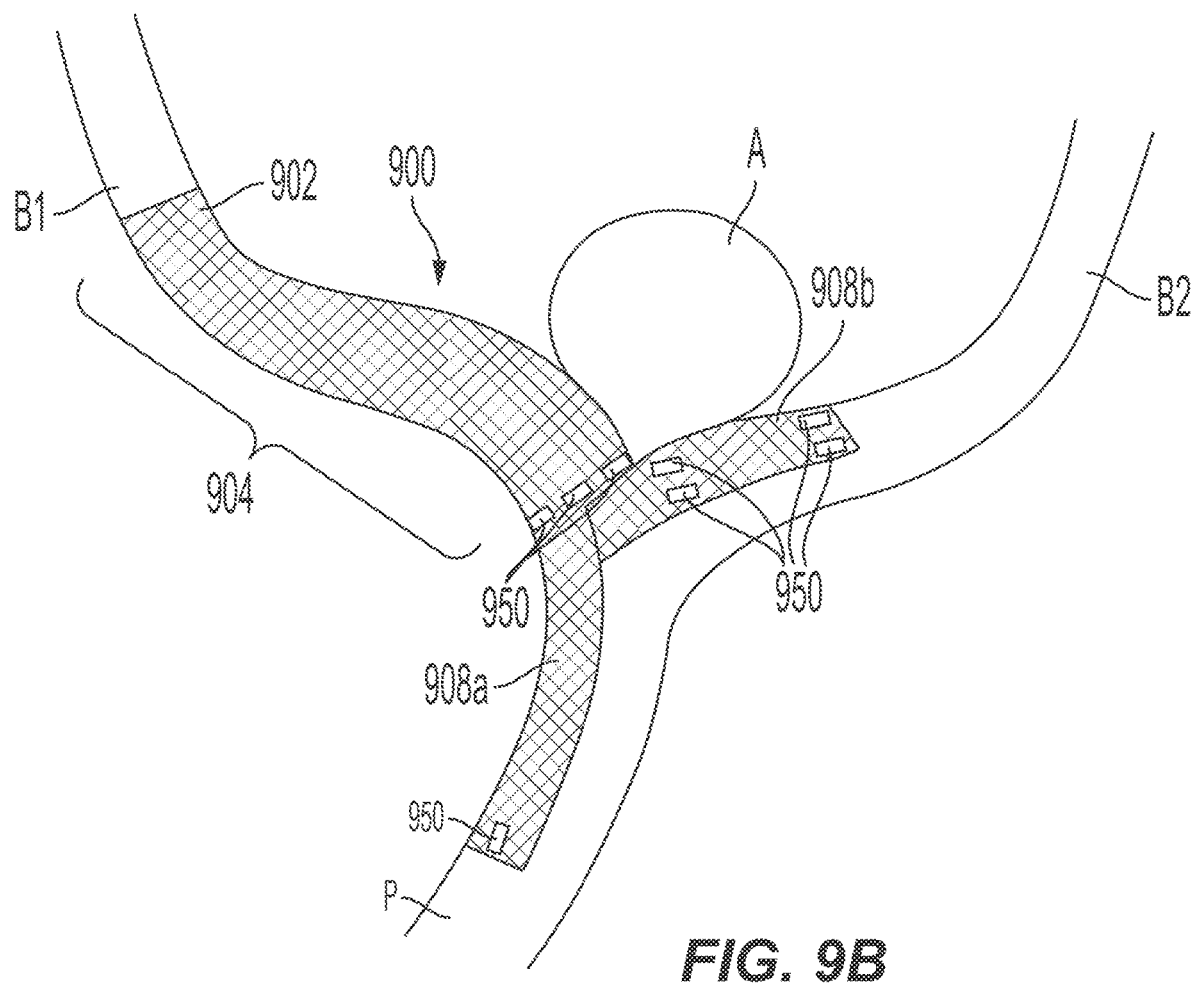
FIG. 9B shows an expandable device in an expanded configuration and positioned at a blood vessel bifurcation in accordance with embodiments of the present technology.

An expandable device of the present technology, such as device 900 shown in FIGS. 9A and 9B, can comprise a radiopaque material (e.g., platinum, platinum-iridium, tantalum, gold, tungsten) to improve visualization of the device 900 within a patient's vasculature. For example, the device 900 can comprise one or more radiopaque markers 950 that can be attached to the mesh 902. The radiopaque markers 950 can comprise coils, bands, plated material, etc. The radiopaque markers 950 may be permanently coupled the device 900 by welding, mechanical attachment, adhesive, or another suitable joining method. In some embodiments, the radiopaque markers are detachably coupled to the device 900. The radiopaque markers may be disposed on an outer surface of the device 900, an inner surface of the device 900, and/or between the inner and outer surfaces of the device 900. In some embodiments, one or more portions of the mesh 902 of the device 900 (e.g., one or more mesh struts, one or more mesh wires) are formed of the radiopaque material.

As illustrated in FIGS. 9A and 9B, the radiopaque markers 950 can be attached to the device 900 in a specific pattern to visualize and/or distinguish certain portions of the device. For example, radiopaque markers 950 may be attached to the device 900 in a longitudinal region that is adjacent a second portion 906 of the device 900. Multiple radiopaque markers 950 may be attached around a circumference of the device 900 in a given longitudinal region. The radiopaque markers 950 may be evenly or unevenly spaced around the circumference of the device 900. In addition, or alternatively, the radiopaque markers 950 can be attached to articulating portion(s) 908. When the device 900 comprises multiple articulating portions 908, one articulating portion 908 may comprise a greater number of radiopaque markers 950 than the other articulating portion 908 and/or a different arrangement of radiopaque markers 950 to facilitate identification of the articulating portions 908 when the device 900 is within the patient's vasculature. For example, the first articulating portion 908a shown in FIG. 9A comprises one radiopaque marker, whereas the second articulating portion 908b comprises four radiopaque markers. Radiopaque markers 950 may be spaced circumferentially around each of the articulating portions 908. Although FIG. 9A shows eight radiopaque markers, any suitable number and distribution of radiopaque markers 950 can be used. In various embodiments, the distribution of radiopaque markers 950 along the device 900 can be circumferentially asymmetric, such that the first and second articulating portions 908a and 908b can be distinguished from one another under fluoroscopy.

Figure 11:
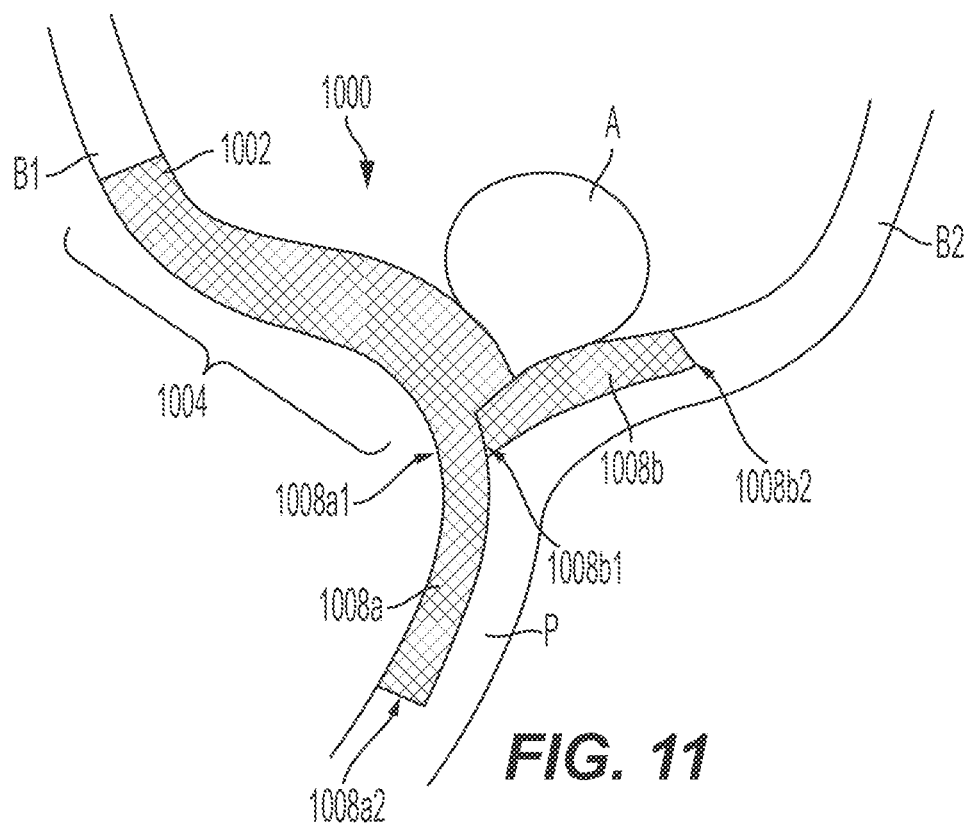
FIG. 11 shows an expandable device in an expanded configuration positioned at a blood vessel bifurcation in accordance with embodiments of the present technology.

FIGS. 10A and 10B illustrate an example of an expandable device 1000 comprising a mesh 1002 in a constrained configuration and an expanded configuration, respectively. FIG. 11 depicts the expandable device 1000 located at a vessel bifurcation and covering a neck of an aneurysm. With collective reference to FIGS. 10A-11, the device 1000 can comprise a first portion 1004 configured to be positioned within a first blood vessel lumen of a patient (e.g., the lumen of branching vessel B1 as shown in FIG. 11, etc.) and a second portion 1006. In some embodiments, the first and second portions 1004, 1006 are continuous along a longitudinal axis L of the device 1000. The second portion 1006 can comprise a first articulating portion 1008a and a second articulating portion 1008b (collectively "articulating portions 1008"). As shown in FIG. 11, the first articulating portion 1008a can be configured to be positioned within a second blood vessel lumen (e.g., the lumen of parent vessel P, etc.) and the second articulating portion 1008b can be configured to be positioned within a third blood vessel lumen (e.g., the lumen of branch vessel B2, etc.). The first articulating portion 1008a can have a first length 1014a defined between a first end 1008a1 of the first articulating portion 1008a that is located at the first portion 1004 of the device 1000 and a free second end 1008a2. The second articulating portion 1008b can have a second length 1014b defined between a first end 1008b1 of the second articulating portion 1008b that is located at the first portion 1004 of the device 1000 and a free second end 1008b2. In some embodiments, the second length 1014b is less than the first length 1014a. The second length 1014b can be reduced to facilitate delivery of the second articulating portion 1008b to the third blood vessel lumen.

Figure 12B:
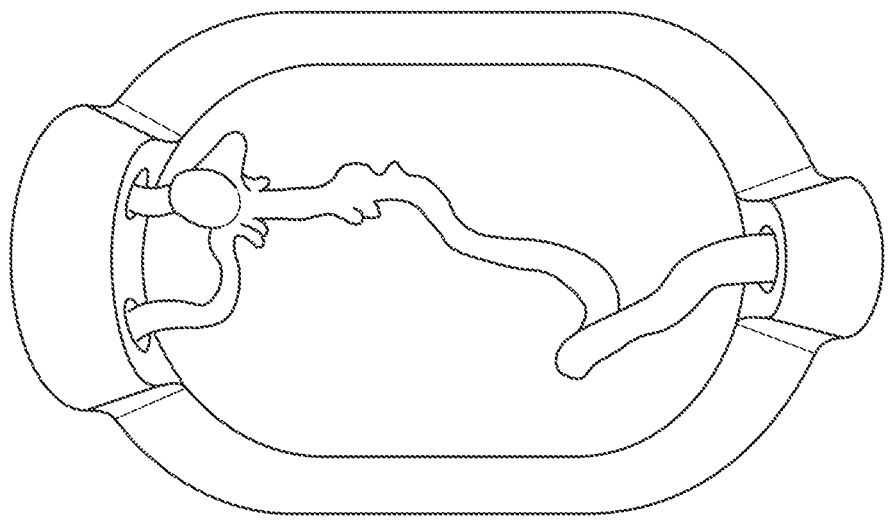
FIGS. 12A-12D show models of example cerebral bifurcation aneurysms.
Figure 12A:
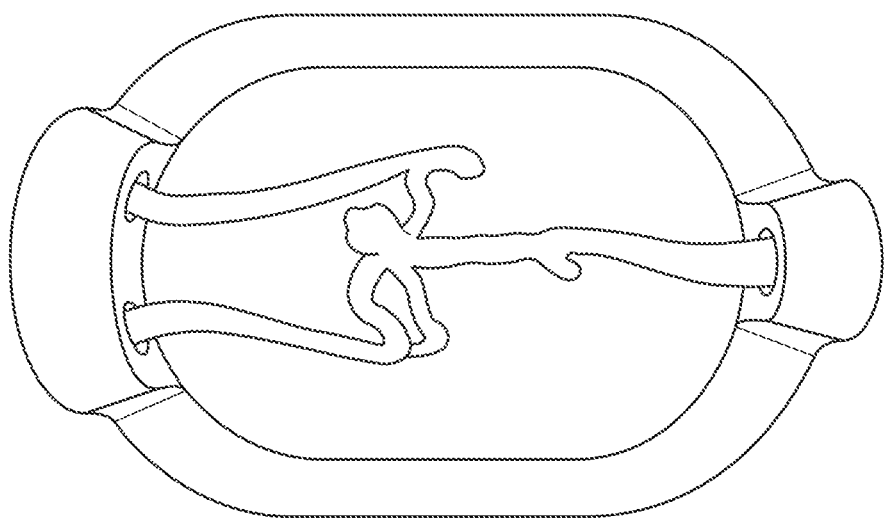
Figure 12C:
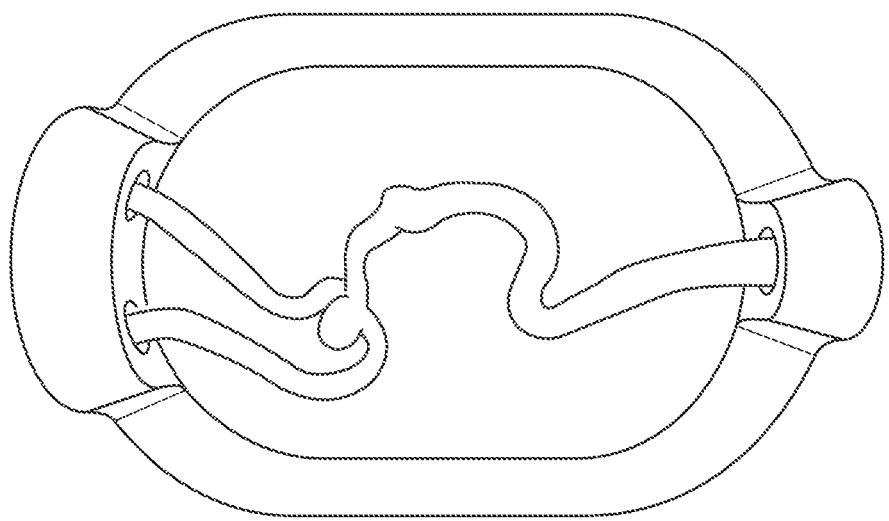
Figure 12D:
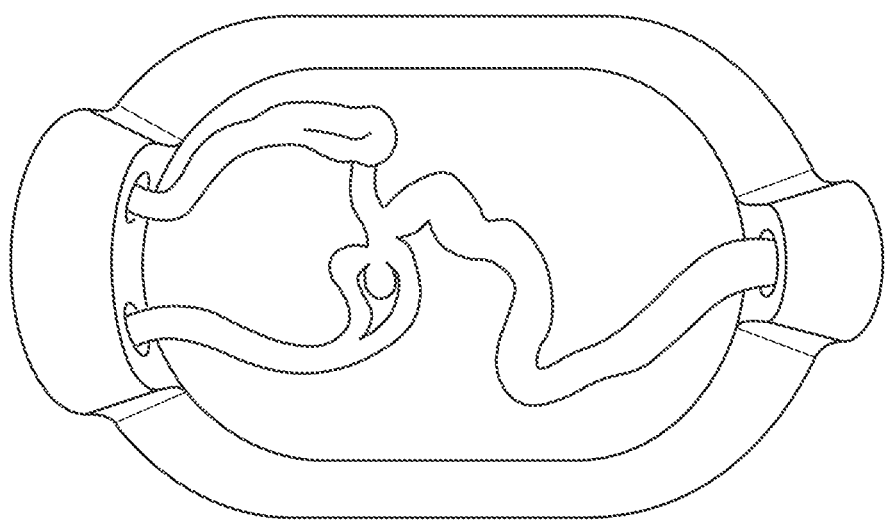

In some embodiments, for example as shown in FIG. 11, the first portion 1004 and the second articulating portion 1008b can be configured to be positioned downstream of the first articulating portion 1008a. While the device 1000 is being advanced to the treatment site (e.g., within a catheter, in a constrained configuration, etc.) the second end 1008b2 of the second articulating portion 1008b can be located proximal of the first portion 1004 and/or proximate the second end 1008a2 of the first articulating portion 1008a. To deploy the device 1000, the second articulating portion 1008b may be inverted, rotated, hinged, displaced, and/or otherwise manipulated such that its free second end 1008b2 moves away from and/or proximal of the second end 1008a2 of the first articulating portion 1008a. However, such movement and/or deformation of the second articulating portion 1008b can be frustrated by a geometry and/or size of the blood vessels at the bifurcation. If the second articulating portion 1008b prematurely contacts a wall of a blood vessel (such as the parent blood vessel P, etc.), it may inadvertently anchor to the vessel wall, making it challenging to deploy the second articulating portion 1008b to its full extent and/or to its intended position. Accordingly, the second length 1014b of the second articulating portion 1008b can be small to facilitate positioning and deployment of the second articulating portion 1008b at the treatment site. In various embodiments, the second length 1014b can be sufficiently large to ensure or promote complete coverage of the neck of the aneurysm by the device 1000. The second length 1014b (or any other length disclosed herein) can be based at least in part on a geometry of the treatment site (e.g., diameters of vessels, lengths of vessels, angles between vessels, etc.). In some cases, it can be challenging to sufficiently cover a neck of a bifurcation aneurysm with a flow-diverting device because of the unique shapes, sizes, and locations of the various bifurcation aneurysms that can occur. FIGS. 12A-12D depict models of examples of bifurcation aneurysms that can occur in the cerebral vasculature. FIG. 12A depicts a basilar bifurcation aneurysm A, FIG. 12B depicts another basilar bifurcation aneurysm A, FIG. 12C depicts an MCA bifurcation aneurysm A, and FIG. 12D depicts an ICA bifurcation aneurysm A. Any of these bifurcation aneurysms and others comprises a three-dimensional structure with a dome height, dome diameter, and neck width, and these parameters can be highly variable between patients, vessels, aneurysm locations, etc. The branching vessels and parent vessel adjacent to a bifurcation aneurysm can have a variety of diameters, lengths, and degrees of curvature. For example, the basilar artery can have a lumen diameter of approximately 2.9 mm, while the proximal cerebral arteries have luminal diameters of about 1.8 mm.

Figure 13:
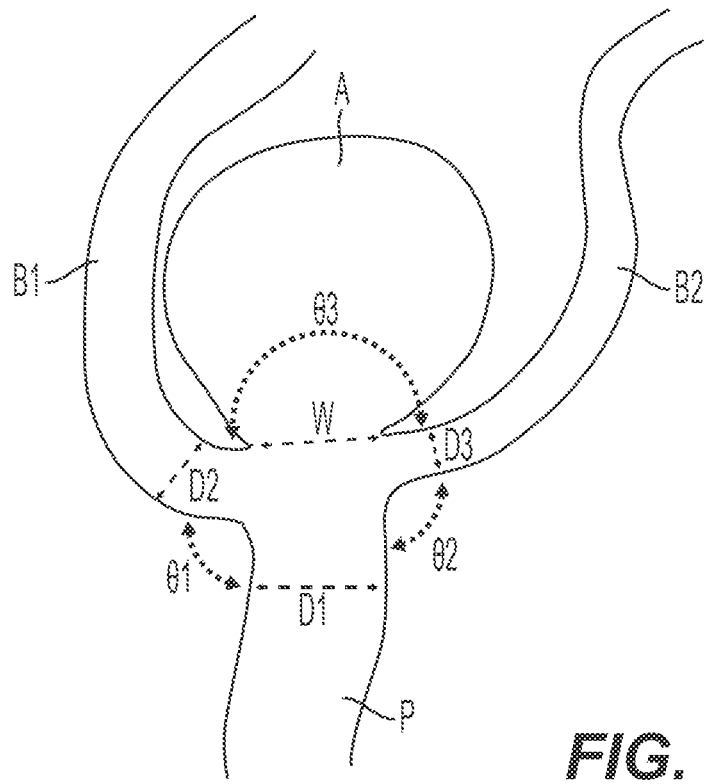
FIG. 13 shows a treatment site comprising a parent blood vessel, a first branching blood vessel, a second branching blood vessel, and an aneurysm positioned between the first and second branching blood vessels.
Figure 14:
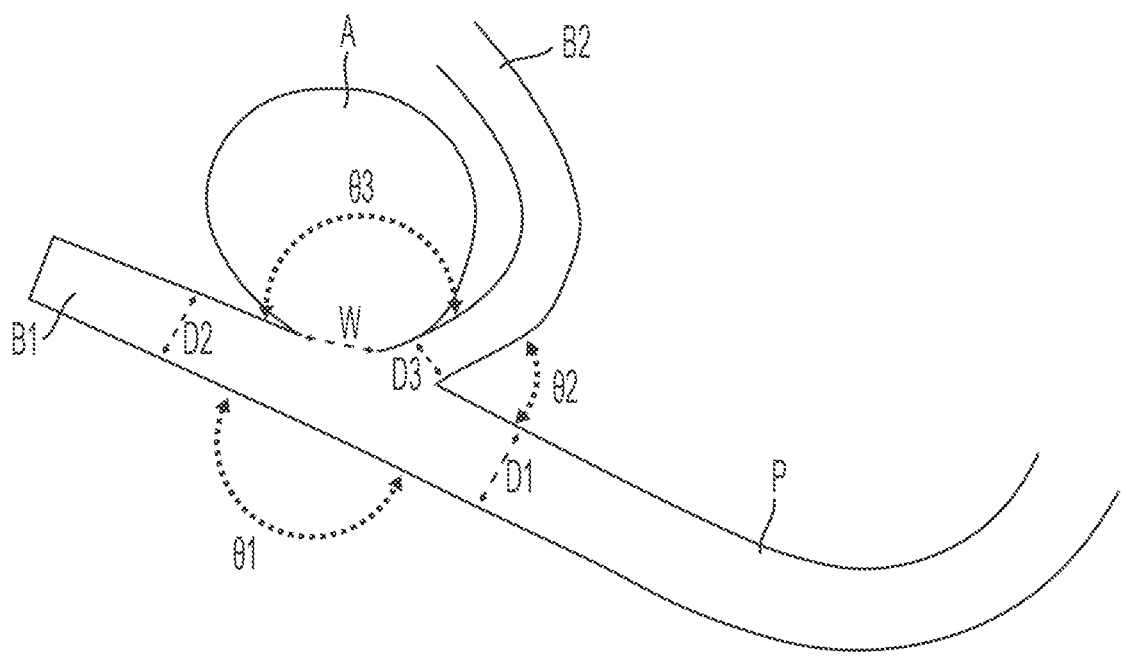
FIG. 14 shows a treatment site comprising a parent blood vessel, a first branching blood vessel, a second branching blood vessel, and an aneurysm positioned between the first and second branching blood vessels.

FIGS. 13 and 14 are cross-sectional views of example bifurcation aneurysms for illustrating the variance that can occur between aneurysms. In both FIGS. 13 and 14 the treatment site comprises a parent blood vessel P, a first branching blood vessel B1, a second branching blood vessel B2, and an aneurysm A. Although FIGS. 13 and 14 depict the aneurysm A positioned between the first and second branching blood vessels B1, B2, in some cases the aneurysm A can be positioned between the first branching blood vessel B1 and the parent blood vessel P or between the second branching blood vessel B2 and the parent blood vessel P. The first branching blood vessel B1 can be angled with respect to the parent blood vessel P according to a first angle $\theta 1$, the second branching blood vessel B2 can be angled with respect to the parent blood vessel P according to the second angle $\theta 2$, and the first and second branching blood vessels B1, B2 can be angled with respect to one another according to a third angle $\theta 3$. The parent blood vessel P can have a diameter D1, the first branching blood vessel B1 can have a diameter D2, the second branching blood vessel B2 can have a diameter D3. The neck of the aneurysm A can have a width W.

As shown in FIG. 13, in some cases the first and second branching blood vessels B1, B2 are substantially angled with respect to the parent blood vessel P. In such cases, the third angle $\theta 3$ can be about 180 degrees. Accordingly, an expandable device for treating such a bifurcation aneurysm A can have an expanded state in which a second articulating portion configured to be positioned in the second branching blood vessel B2 and a first portion configured to be positioned in the first branching blood vessel B1 are substantially aligned along a longitudinal dimension of the device. The first angle $\theta 1$ and/or the second angle $\theta 2$ can be substantially 90 degrees, as shown in FIG. 13. Accordingly, an angle between a first portion of an expandable device configured to be positioned in the first branching blood vessel B1 and a first articulating portion of the device configured to be positioned in the parent blood vessel P can be about 90 degrees. As shown in FIG. 13, in some embodiments the diameter D1 of the parent vessel P is greater than the diameter D2 of the first branching blood vessel B1 and/or the diameter D3 of the second branching blood vessel B2. Accordingly, a radius of curvature of a first articulating portion of an expandable device configured to be positioned within the parent blood vessel P may be larger than a radius of curvature of portions of the device configured to be positioned within the first and second branching blood vessels B1, B2. In some cases, the diameter D2 of the first branching blood vessel B1 is substantially similar to the diameter D3 of the second branching blood vessel B2 such that a radius of curvature of a first portion of an expandable device configured to be positioned in the parent vessel P is substantially similar to a radius of curvature of a second articulating portion of the device configured to be positioned within the second branching blood vessel B2. As shown in FIG. 13, in some embodiments the width W of the aneurysm neck is large, which can be difficult to completely cover with an expandable device. In such cases, it may be advantageous for a second articulating portion of an expandable device, for example, to have a length that is greater than the width W of the aneurysm neck, to facilitate complete coverage of the aneurysm neck by that portion of the device.

As shown in FIG. 14, in some cases the first branching blood vessel B1 is not substantially angled with respect to the parent blood vessel P (e.g., the first angle $\theta 1$ is about 0 degrees or about 180 degrees). In such embodiments, a first portion of an expandable device configured to be positioned in the first branching blood vessel B1 and a first articulating portion of the device configured to be positioned in the parent vessel P can be substantially aligned along a longitudinal dimension of the device. However, as shown in FIG. 14, the second branching blood vessel B2 may be angled with respect to the parent blood vessel P and/or the first branching blood vessel B1. For example, the second angle $\theta 2$ and/or the third angle $\theta 3$ can be acute, obtuse, or about 90 degrees. As shown in FIG. 14, in some cases the width W of the aneurysm neck may be smaller, but may be located very close to the opening to the second branching blood vessel B2. Additionally or alternatively, the diameter D2 of the first branching blood vessel B1 can be substantially different than the diameter D3 of the second branching blood vessel B2 such that a radius of curvature of a first portion of an expandable device configured to be positioned in the first branching blood vessel B1 is substantially different than a radius of curvature of a second articulating portion of the device configured to be positioned within the second branching blood vessel B2.

To effectively treat any one of a variety of bifurcation aneurysms that may exist, an expandable device of the present technology can be at least partially shaped and/or sized based on the treatment site to which the device is configured to be delivered (e.g., the bifurcation aneurysm to be treated and/or the adjacent blood vessels). For example, a length of one or more portions (e.g., the first portion, the first articulating portion, the second articulating portion, etc.) of a device, a radial dimension (e.g., a diameter of the first portion, a radius of an articulating portion, etc.) of one or more portions of a device, an angle between two or more portions of a device, etc. can be based on the treatment site. In some embodiments, a radial dimension of a specific portion of the device can be based on a diameter of a lumen of a blood vessel in which the specific portion of the device is configured to be positioned. The radial dimension of the specific portion of the device can be based on an average vessel lumen diameter of a population and/or a vessel lumen diameter of a specific patient.

Any of the devices disclosed herein can be at least partially customized to a bifurcation aneurysm to be treated. For example, in some embodiments, a device of the present technology has an expanded configuration reflecting a three-dimensional shape of the treatment site. Each specific portion of the device can have a radial dimension based on the specific diameters of the lumens of the blood vessels adjacent to the aneurysm. Additionally or alternatively, a length of one or more portions of the device can be based on a width of the neck of the aneurysm to ensure that such portions of the device will sufficiently cover the aneurysm neck once deployed. In some cases, a length of one or more portions of the device is configured to prevent or limit the one or more portions from disadvantageously covering and occluding a branching vessel.

Figure 15B:
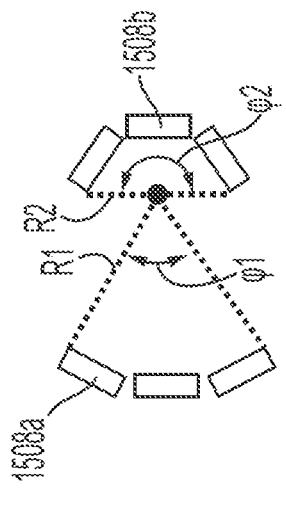
FIGS. 15A and 15B are isometric and cross-sectional views, respectively, of an expandable device in a constrained configuration in accordance with embodiments of the present technology.
Figure 15A:
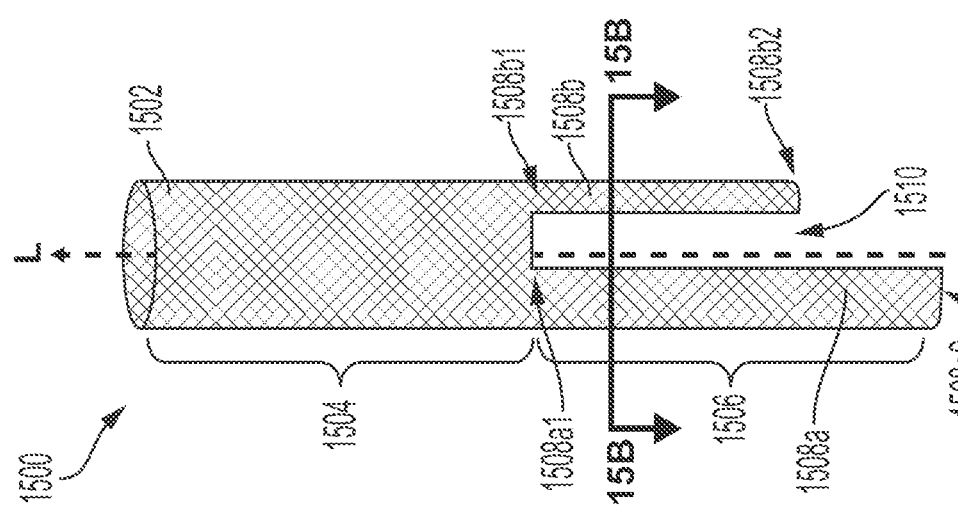

A device of the present technology can have one or more parameters that are based, at least in part, on the anatomy of a treatment site to which the device is configured to be deployed. Some of such parameters are discussed with reference to the expandable device 1500 shown in FIGS. 15A-15C. The expandable device 1500 can comprise a mesh 1502 including a first portion 1504 and a second portion 1506 extending away from the first portion 1504 along a longitudinal axis L of the device 1500. The second portion 1506 can include one or more articulating portions 1508, for example the first articulating portion 1508a and the second articulating portion 1508b shown in FIGS. 15A-15C. Each of the first articulating portion 1508a and the second articulating portion 1508b can extend from a first end 1508a1, 1508b1 at the first portion 1504 to a free second end 1508a2, 1508b2. As shown in FIG. 15A, the second end 1508a2 of the first articulating portion 1508a can be spaced apart from the first portion 1504 by a greater distance than the second end 1508b2 of the second articulating portion 1508b. In other words, the first articulating portion 1508a can be longer than the second articulating portion 1508b. In some embodiments, a length of the first articulating portion 1508a, a length of the second articulating portion 1508b, and/or a length of the first portion 1504 is based, at least in part, on the treatment site to which the portion of the device is configured to be deployed. For example, the second articulating portion 1508b can have a length greater than a width of the neck of the aneurysm to be treated so that the second end 1508b2 of the second articulating portion 1508b can be positioned within the second branching blood vessel B2 and sufficiently span across the neck of the aneurysm A to obstruct flow into the aneurysm A.

In some embodiments, the first portion 1504 is circumferentially continuous. A diameter of the first portion 1504 can be based on a diameter of a first branching blood vessel (or another vessel that the first portion 1504 is configured to be deployed within). For example, the first portion 1504 can have a diameter that is slightly larger than a diameter of a first branching blood vessel in which the first portion 1504 is configured to be deployed. Such oversizing of the first portion 1504 can facilitate anchorage of the first portion 1504 to the vessel wall. In some embodiments, the first portion 1504 has a higher porosity and/or a lower surface coverage than a corresponding parameter of the first articulating portion 1508a and/or the second articulating portion 1508b.

Figure 15C:
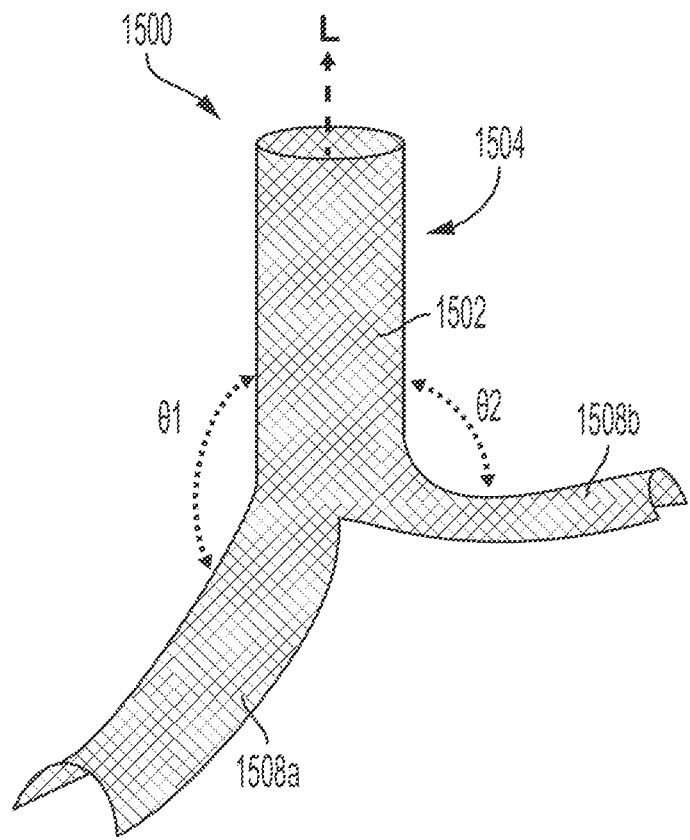
FIG. 15C is an isometric view of the expandable device in an expanded configuration.

Each of the articulating portions 1508a, 1508b can be circumferentially discontinuous, or one or more of the articulating portions 1508a, 1508b can be circumferentially continuous. In some embodiments, the first articulating portion 1508a can be separated from the second articulating portion 1508b by longitudinal slits 1510. In some embodiments, for example as shown in FIGS. 15A-15C, the slits 1510 have a non-zero circumferential width. Accordingly, the first articulating portion 1508a can comprise first longitudinal edges 1512a and the second articulating portion 1508b can comprise second longitudinal edges 1512b, and corresponding ones of the first and second longitudinal edges 1512a, 1512b can be spaced apart from one another about a circumference of the device 1500. In some embodiments, the widths of the slits 1510 are based at least in part on an angle between two or more blood vessels at a specific treatment site. For example, the width of the slit 1510 can be larger to facilitate positioning of the second articulating portion 1508b at a more acute angle relative to the first portion 1504 when the device is in an expanded state.

As shown in FIG. 15B, the first articulating portion 1508a can subtend a first angle $\varphi 1$ and the second articulating portion 1508b can subtend a second angle $\varphi 2$. The first angle $\varphi 1$ can be the same as the second angle $\varphi 2$ or, as shown in FIG. 15B, the first angle $\varphi 1$ can differ from the second angle $\varphi 2$. The first angle $\varphi 1$ can be larger than the second angle $\varphi 2$ (see FIG. 15B) or can be smaller than the second angle $\varphi 2$. According to various embodiments, the angle subtended by one of the articulating portions (and thereby a width of the articulating portion) can be based at least in part on an intended function of the articulating portion. For example, in embodiments in which the second articulating portion 1508b is configured to be positioned over a neck of an aneurysm, the second angle $\varphi 2$ can be larger than the first angle $\varphi 1$ to facilitate complete coverage of the aneurysm neck by the second articulating portion 1508b.

The first articulating portion 1508a can have a first radius of curvature R1 and the second articulating portion 1508b can have a second radius of curvature R2. The first radius of curvature R1 can be the same as the second radius of curvature R2 or different than the second radius of curvature R2. According to various embodiments, a radius of curvature of an articulating portion is based at least in part on a diameter of a blood vessel that the articulating portion is configured to be positioned within. For example, if the first articulating portion 1508a is configured to be positioned within a parent blood vessel and the second articulating portion 1508b is configured to be positioned within a branching blood vessel having a smaller diameter than the parent blood vessel, the first radius of curvature R1 may be larger than the second radius of curvature R2.

The expandable device 1500 can have a constrained state, for example as shown in FIGS. 15A and 15B, and an expanded state, for example as shown in FIG. 15C. In the constrained state, the first and second articulating portions 1508a, 1508b can extend in a substantially longitudinal direction. Thus, a first angle $\theta 1$ between the first portion 1504 and the first articulating portion 1508a and a second angle $\theta 2$ between the first portion 1504 and the second articulating portion 1508b can each be about 0 degrees (or 180 degrees). As shown in FIG. 15C, when the device 1500 is in the expanded state, the first angle $\theta 1$ and/or the second angle $\theta 2$ can be substantially non-zero (or not 180 degrees). The first angle $\theta 1$ and the second angle $\theta 2$ can be the same or different. In various embodiments, the first angle $\theta 1$ and/or the second angle $\theta 2$ is based on an angle between two blood vessels at a treatment site. For example, as shown in FIG. 14, in some cases a first branching blood vessel is substantially parallel to a parent blood vessel. In such embodiments, the first angle $\theta 1$ between a first portion 1504 configured to be positioned within the first branching blood vessel and a first articulating portion 1508a configured to be positioned within the parent blood vessel can be about 0 degrees. However, in some cases (for example as shown in FIG. 13), first and second branching blood vessels can extend away from a parent blood vessel at non-zero angles. In such embodiments (and others), the first angle θ1 and/or the second angle θ2 can be based on the angles between the parent blood vessel, the first branching blood vessel, and/or the second branching blood vessel.

According to some embodiments, a radius of curvature of one or more portions of the device 1500 can be larger in the expanded state than in the constrained state. For example, the first portion 1504 can be configured to expand from a first diameter in the radially constrained state to a second, larger diameter in the expanded state. The first diameter can be based on a diameter of an elongated shaft (e.g., catheter, etc.) through which the device 1500 is configured to be delivered and/or the second diameter can be no smaller than a diameter of a blood vessel in which the first portion 1504 is configured to be deployed. In some embodiments, the first radius of curvature R1 of the first articulating portion 1508a and/or the second radius of curvature R2 of the second articulating portion 1508b is based on a diameter of the vessel within which the respective portion is configured to be positioned. For example, the first radius of curvature R1 can be no smaller than a diameter of the vessel within which the first articulating portion 1508a is configured to be positioned and/or the second radius of curvature R2 can be no smaller than a diameter of the vessel within which the second articulating portion 1508b is configured to be positioned. Such configuration can facilitate the first articulating portion 1508a and/or the second articulating portion 1508b substantially conforming to their respective vessel walls. According to various embodiments, the first radius of curvature R1 and/or the second radius of curvature R2 can be substantially constant along a length of the articulating portion or can vary along a length of the articulating portion.

III. Manufacturing Expandable Devices of the Present Technology

The expandable devices disclosed herein can be manufactured using any one or more suitable techniques or materials. An expandable device of the present technology may comprise an expandable mesh formed from one or more metals, polymers, composites, and/or biologic materials. In some embodiments, the expandable mesh may comprise one or more metal(s) and/or alloy(s), including superelastic metals/alloys (e.g., nickel-titanium alloys such as Nitinol, etc.) or other metals/alloys such as stainless steel, cobalt-chromium alloys, cobalt-nickel alloys (e.g., 35N LT™ available from Fort Wayne Metals of Fort Wayne, Indiana USA), etc. The mesh can be configured to self-expand when released from a lumen of a catheter, as described in greater detail elsewhere herein. In some embodiments, the expandable mesh can be formed from platinum, platinum-tungsten alloy, gold, magnesium, iridium, chromium, zinc, titanium, tantalum, and/or alloys of any of the foregoing metals or including any combination of the foregoing metals. In several embodiments, the expandable mesh may be highly polished and/or surface treated to further improve hemocompatibility. The expandable mesh may be constructed solely from metallic materials without the inclusion of any polymer materials or may include a combination of polymer and metallic materials. Some or all of the expandable mesh may be formed at least in part from radiopaque material, metal or alloy.

In some embodiments, some or all of the mesh may be formed of strands or wires that have been braided or woven together. The strands may have a bi-component (or multi-component) configuration comprising an inner core material surrounded by an outer shell material. The core material may include any of the materials disclosed in the preceding paragraph, and the outer material may include any of the materials disclosed in the preceding paragraph. In some embodiments, the core material may be different than the outer material. For example, in some embodiments, the core material is a radiopaque material (e.g., platinum, platinum-tungsten alloy, tantalum, gold, tungsten, etc., or generally one that is more radiopaque than the outer material), and the outer material is a resilient or highly elastic and/or superelastic material (e.g., Nitinol, 35N LT, etc., or generally one that is of higher Young's modulus than the outer material). The core material may have a cross-sectional area (based on a cross-sectional dimension $d_c$) that comprises about 5% to about 50%, about 10% to about 45%, about 15% to about 40%, about 10%, about 15%, about 20%, about 25%, about 30%, about 35%, about 40%, about 45% of the total-cross-sectional area of the individual strands (this measure is referred to as the "percent fill" of the strand accounted for by the core material).

Some suitable materials and combinations for the strands of the expandable mesh include: (a) all strands of coaxial bi-component configuration, with a cobalt-nickel outer material and a platinum or platinum-tungsten (or other radiopaque) core material; (b) all strands of coaxial bi-component configuration, with a nickel-titanium outer material and a platinum or platinum-tungsten (or other radiopaque) core material; (c) a combination of some coaxial bi-component strands of cobalt-nickel outer material and a platinum or platinum-tungsten (or other radiopaque) core material, and some single-component strands of cobalt-nickel; (d) a combination of some coaxial bi-component strands of nickel-titanium outer material and a platinum or platinum-tungsten (or other radiopaque) core material, and some single-component strands of nickel-titanium; (e) a combination of some single-component strands of cobalt-nickel or nickel-titanium with some single-component strands of platinum or platinum-tungsten (or other radiopaque material).

Some or all of the strands of the expandable mesh may have an outer cross-sectional dimension that is 0.002 inches (50.8 μm) or less. For example, in some embodiments, half (or fewer) of the strands may have an outer cross-sectional dimension that is 0.002 inches (50.8 μm) or less (or 0.0015 inches (38.1 μm) or less), and each of the remaining strands may have an outer cross-sectional dimension that is 0.0009 inches (22.86 μm) or less. In some embodiments, the outer cross-sectional dimension of each of the strands is 0.001 inches (25.4 μm) or less, and in some embodiments, the outer cross-sectional dimension of each of the strands is 0.0009 inches (22.86 μm) or less, 0.0008 inches (20.32 μm) or less, or 0.0007 inches (17.78 μm) or less. In some embodiments, some or all of the strands may have a circular cross-sectional shape and the relevant cross-sectional dimension is the diameter of the strands. In some embodiments, some or all of the strands may have other cross-sectional shapes, such as polygonal (e.g., rectangular, square, triangular, etc.), oval-shaped, ellipsoid, and other suitable shapes. In those non-circular embodiments, the relevant cross-sectional dimension is that which comprises the greatest cross-sectional dimension measured orthogonal to the long axis of the strand. In some embodiments, the expandable mesh may include a mixture of strands having different cross-sectional shapes and/or sizes. In several embodiments, the greater the diameter of the expandable mesh in the expanded state, the greater the average cross-sectional dimension of the strands.

The expandable mesh of the present technology can be at least partially formed of small strands (e.g., strands having a cross-sectional dimension less than 0.001 inches or 25.4 μm), which provide several advantages. For example, the use of small strands decreases the overall profile of the expandable mesh, thereby allowing the expandable mesh to be compressed to smaller diameters and delivered to more remote, smaller blood vessels and/or through smaller catheters. The smaller profile in turn reduces in-catheter friction and thus improves the pushability of the expandable device and/or ease of delivery of the expandable device. Including at least some small strands also allows the use of more total strands for larger devices (e.g., having an expanded state diameter or 4 mm or more), which helps maintain a relatively consistent pore size across a range of devices that very widely in implanted or expanded state diameter. Upon implantation, an expandable device with small strands is more easily endothelialized (overgrown and covered with vessel wall tissue), leading to faster healing and elimination of adverse effects (e.g. thrombosis) arising from exposure of blood flow to the material of the strands. The expandable mesh may include 1, 2, 8, 10, 12, 14, 22, 28, 30, 32, 36, 40, 44, 48, 52, 58, 64, 70, 86, 90, 110, 116, 120, 128, 136, 150, or greater strands that may be assembled or configured to form a generally tubular (or partial tubular) braid or weave.

Strands of an expandable mesh can cross one another to form pores. All or a portion of the sidewall of the expandable mesh may have a flow-diverting porosity when in the expanded state. A "flow diverting porosity" can refer to a porosity that is configured to inhibit the flow of blood through the sidewall into an aneurysm A to a degree sufficient to lead to thrombosis and healing of the aneurysm. In general, a porosity of the expandable mesh can be computed as the percentage of the surface area of the sidewall of the expandable device that is accounted for by the pores. Porosity can be computed from measured or nominal braid parameters pertaining to a given device. In some embodiments, the porosity of all or a portion of the expandable mesh can be from 5% to 95% when in the expanded configuration. In some embodiments, the porosity of all or a portion of the expandable mesh may be from 30% to 90%, and in some embodiments, the porosity may be from 50% to 85%, or from 60% to 75%, when in the expanded state.

Instead of or in addition to a flow-diverting porosity as described herein, some or all of the pores of the expandable mesh may have a flow diverting pore size when the expandable mesh is in the expanded state. Generally, pore sizes described herein can be measured or computed via the maximum inscribed circle technique, and/or can be an average pore size, and/or a pore size that is computed from measured or nominal braid parameters pertaining to a given device. A "flow diverting pore size" can refer to a pore size (or average pore size) that is sufficiently small to inhibit the flow of blood through the sidewall into an aneurysm to a degree sufficient to lead to thrombosis and healing of the aneurysm when the expandable mesh is positioned in a blood vessel and adjacent to or across the neck of the aneurysm. For example, a flow diverting pore size can be achieved at a pore size of less than 500 microns when the expandable mesh is in the expanded state. In some embodiments, a flow-diverting pore size can be between 5 and 450 microns. In some embodiments, a flow-diverting pore size can be less than 320 microns, in the range of 20-300 microns, in the range of 25-250 microns, or in the range of 50-200 microns.

Additionally or alternatively, a surface coverage of the expandable mesh can be defined as a surface area of the expandable mesh comprising strand material divided by a total surface area of the entire expandable mesh (e.g., including strand material and openings). A surface coverage of the expandable mesh (or one or more portions thereof) can be at least 20%, at least 30%, at least 40%, at least 50%, at least 60%, at least 70%, at least 80%, or at least 90%. In some embodiments, a surface coverage of the expandable mesh (or one or more portions thereof) is between about 20% to about 35%, for example about 25%, about 30%, etc. According to various embodiments, a portion of an expandable mesh configured to be positioned at or adjacent to a neck of an aneurysm can have a greater surface coverage than other portions of the expandable mesh.

In some embodiments, the expandable mesh may have an expanded state diameter of 2.5-3.5 mm and include 48 strands, each having a strand outer diameter of 0.0009-0.0013 inches. In such embodiments (or in any other embodiment of the expandable devices and/or meshes disclosed herein), the expandable mesh may optionally have: (a) a radial braid angle in the expanded state of 53-61 degrees, where the radial braid angle is that subtended at the upper or lower vertex of a cell as the expandable mesh in question is viewed with its lumen extending horizontally, (b) an on-mandrel braided picks-per-inch (PPI) of 250-275, and/or (c) a braid pattern of 1-over-2-under-2. In such embodiments, all of the strands may optionally be drawn-filled-tube (DFT) wires with a cobalt-nickel alloy (35NLT) outer annular shell surrounding a concentrically disposed inner cylindrical core of platinum. The DFT wires may be 28%-41% (where the percentage represents the proportion of the total strand cross-sectional area taken up by the core).

In some embodiments, the expandable mesh may have an expanded state diameter of 4.0-6.0 mm and include 64 strands, each having a strand outer diameter of 0.0009-0.0015 inches. In such embodiments (or in any other embodiment of the expandable devices or meshes disclosed herein), the expandable mesh may optionally have: (a) a radial braid angle in the expanded state of 48-55 degrees, where the radial braid angle is that subtended at the upper or lower vertex of a cell as the expandable mesh in question is viewed with its lumen extending horizontally, (b) an on-mandrel braided picks-per-inch (PPI) of 150-200, and/or (c) a braid pattern of 1-over-2-under-2. In such embodiments, all of the strands may optionally be DFT wires with a cobalt-nickel alloy (35NLT) outer annular shell surrounding a concentrically disposed inner cylindrical core of platinum. The DFT wires may be 28%-41% (where the percentage represents the proportion of the total strand cross-sectional area taken up by the core).

In some embodiments, the expandable mesh may include a coating or surface treatment disposed on at least a portion thereof, for example, on an outer surface of some or all of the strands, and/or along some or all of the length of the expandable mesh. Such a coating or surface treatment may be anti-thrombogenic, so as to reduce or minimize the clotting of blood in response to the implantation of the expandable mesh. As employed herein, "anti-thrombogenic" can mean less thrombogenic than the material forming the outer surface of the strands when uncoated or untreated. In some embodiments, the anti-thrombogenic coating or surface treatment comprises a phosphorylcholine, for example 2-methacryloyloxyethyl phosphorylcholine (MPC, available as LIPIDURE™ from NOF Corporation of Tokyo, Japan). A suitable form of MPC is LIPIDURE™-CM2056, or 2-methacryloyloxyethyl phosphorylcholine-poly(n-butyl methacrylate). Other suitable anti-thrombogenic coatings or surface treatments include platelet aggregation inhibitors, and anti-thrombogenic polymers or monomers. These can include PARYLENE C™, or PARYLENE HT™, both available from Specialty Coating Systems of Indianapolis, Ind.; BAYIVIEDIX™ available from Bayer AG of Leverkusen, Germany; BIOCOAT™ hyaluronic acid available from Bio-Coat, Inc. of Horsham, Pa.; or polyethylene oxide. Other suitable anti-thrombogenic materials include heparin, heparin-like materials or derivatives, hirudin, H—Heparin, HSI—Heparin, albumin, phospholipids, streptokinase, tissue plasminogen activator (TPA), urokinase, hyaluronic acid, chitosan, methyl cellulose, poly(ethylene oxide), poly (vinyl pyrrolidone), endothelial cell growth factor, epithelial growth factor, osteoblast growth factor, fibroblast growth factor, platelet derived growth factor or angiogenic growth factor.

An expandable mesh of the present technology can optionally be similar to any of the versions or sizes of the PIPELINE™ Embolization Device marketed by Medtronic Neurovascular of Irvine, California USA. The expandable mesh can alternatively comprise any suitable medical device and/or other features. In some embodiments, the expandable mesh can be any one of the stents described in U.S. application Ser. No. 15/892,268, filed Feb. 8, 2018, titled VASCULAR EXPANDABLE DEVICES, the entirety of which is hereby incorporated by reference herein and made a part of this specification.

In some embodiments, the mesh may be formed from sheet or tube of any suitable material such as, but not limited to, the materials described elsewhere herein. Any suitable cutting process such as cutting, laser cutting, milling, chemical etching, wire electrical discharge machining (EDM), water jetting, punching (stamping), chemical etching, etc. may be used to cut the mesh from the material. The sheet or tube of material can have a thickness selected to achieve the desired material properties of the resulting mesh. In various embodiments, the thickness of the sheet or tube of material can be uniform or can vary (e.g., along a gradient, being thinned at particular regions using etching, grinding, etc., or thickened at particular regions using deposition, etc.). In some embodiments, the mesh is formed directly as a sheet or tube by an additive process such as thin film deposition, 3D printing, etc.

In some embodiments, the mesh can be bent or otherwise manipulated to form a constrained configuration of the mesh (e.g., a tubular configuration, etc.). For example, in embodiments in which the mesh is initially formed of a flat sheet of material (e.g., by laser cutting a sheet, by thin film deposition, etc.), the tubular configuration can be created by removably coupling the mesh to a tubular mold or fixture and subjecting the mesh to a heat treatment process. In some embodiments, the tubular configuration is formed by deforming the flat sheet of material into a generally tube-like shape such that the longitudinal edges of the flat pattern are positioned adjacent to or in contact with one another. The longitudinal edges can be joined (e.g., via laser welding) along all or a portion of their respective lengths. In some embodiments, the edges can overlap so that the overlapping portion comprises two radial layers of the mesh.

Articulating portions of the present technology can be formed by creating slits in the mesh and/or otherwise modifying the mesh. In some embodiments, the slits can be formed by a suitable cutting process such as, but not limited to, the cutting processes previously described. In various embodiments, the mesh can be modified to create articulating portions of specific shapes and sizes. For example, a free end of a second articulating portion can be cut circumferentially to reduce a length of the second articulating portion. The cut edges of the mesh can be secured by welding, crimping, melting, gluing, braiding, clamping, or another suitable securing method. Such securing of the mesh edges can be particularly important for braided meshes. For example, if the ends of a braided mesh are cut without being secured, filaments of the braided mesh may unravel. Laser cut stents may not suffer from similar manufacturing challenges. In some embodiments, various portions of the mesh (e.g., first portion, articulating portions) can be formed separately and then coupled together. The portions of the mesh can be coupled by any suitable joining method such as, but not limited to, welding, crimping, melting, gluing, etc. In some embodiments, an articulating portion can be formed by extruding a material forming the first portion of the mesh.

In some embodiments, the mesh can be bent or otherwise manipulated via a shape setting process to create the expanded configuration of the mesh in which one or more articulating portions are positioned at an angle to a first portion of the device. In some embodiments, the shape set process comprises manipulating the mesh into the intended expanded configuration (e.g., by coupling to a mold or fixture) and subjecting the mesh to a heat treatment. In some embodiments, a mold or fixture for forming a shape of the mesh comprises a positive mold and/or a negative mold. As but one example, the positive mold can have a shape substantially corresponding to a desired shape of the mesh in the expanded configuration. The mesh can be positioned over the positive mold to cause the mesh to assume the desired shape. Optionally, a negative mold can be positioned over the mesh and positive mold to cause the mesh to conform to the positive mold. Additionally or alternatively, one or more wires, ties, cables, clamps, sutures, or other fastener can be used to secure the mesh to the positive mold and/or cause the mesh to conform to the positive mold. According to various embodiments, meshes having one shape, size, design, etc. can be shape set to form unique three-dimensional shapes of the meshes. Such unique shapes can be based, at least in part, on a geometry, size, or other configuration of a bifurcation aneurysm to be treated.

One example of a heat treatment procedure can include heating the mesh to a selected temperature for a selected period of time, followed by rapid cooling. The rapid cooling can be achieved by any suitable cooling procedure such as, but not limited to water quench or air-cooling. In particular examples, the heat treatment procedure may be carried out in an air or vacuum furnace, salt bath, fluidized sand bed or other suitable system. In other examples, other suitable heat-treating procedures may be employed including, but not limited to, resistive heating or heating by running a current though the metal of the appliance structure. One or more additional post processing operations may be provided on the mesh after preliminary shape setting, including, but not limited to, abrasive grit blasting, shot peening, polishing, chemical etching, electropolishing, electroplating, coating, ultrasonic cleansing, sterilizing or other cleaning or decontamination procedures.

In some embodiments, a single shape-setting step may be completed to deform the mesh to its desired expanded configuration. However, in certain embodiments the shape setting may include two or more shape-setting steps (e.g., two or more heat treatment processes, potentially using two or more different fixtures). In such cases, the amount of deformation imparted to the mesh within each shape-setting step may be limited, with each subsequent shape-setting step moving the mesh further toward the desired expanded configuration.

IV. Delivery Systems and Methods

The present disclosure also includes systems for delivering an expandable device of the present technology to a patient's vasculature and methods of treating a vascular condition, such as an aneurysm, with any of the embodiments of the expandable devices disclosed herein. The expandable device may be deployed across the neck of an aneurysm and its flow-diverting properties employed to reduce blood flow between the aneurysm and the parent vessel, cause the blood inside the aneurysm to thrombose, and/or lead to healing of the aneurysm.

Figure 16:
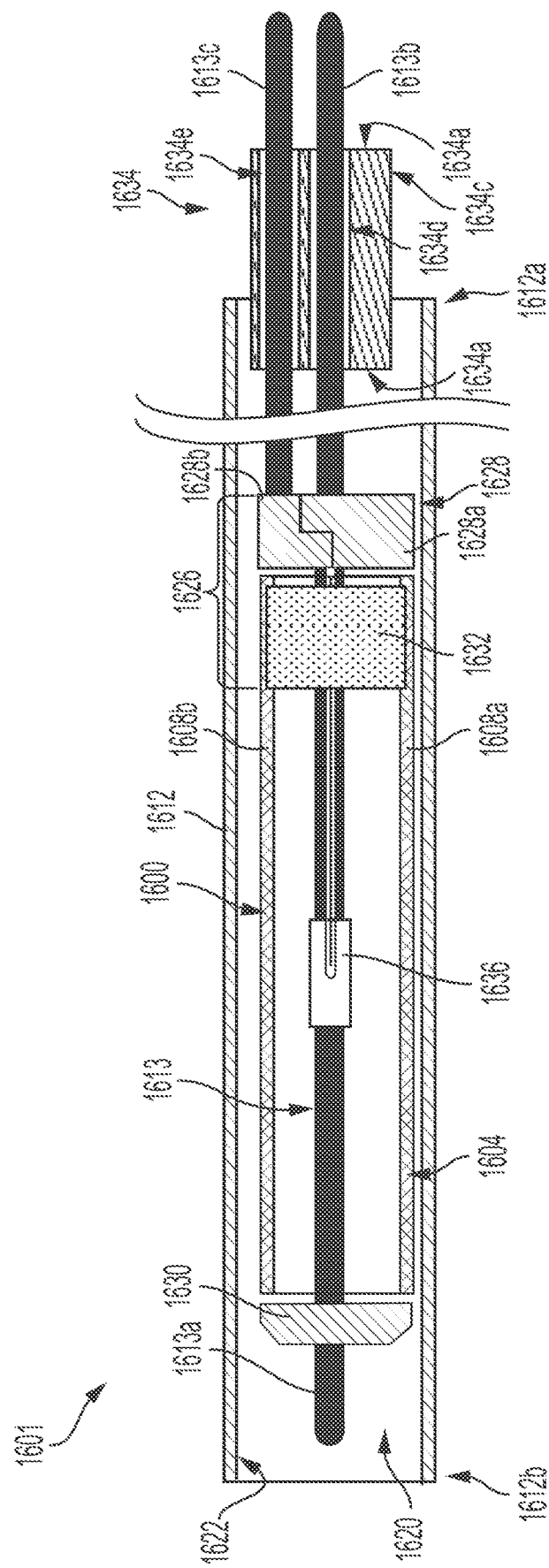
FIG. 16 is a schematic, cross-sectional side view of a delivery system in accordance with embodiments of the present technology.

FIG. 16 shows a side, partial cross-sectional view of an example of a delivery system 1601 in accordance with the present technology. The delivery system may comprise an elongated shaft 1612 (e.g., a microcatheter, a catheter, etc.) having a proximal end portion 1612a, a distal end portion 1612b, a lumen 1620 extending from the proximal end portion 1612a to the distal end portion 1612b, and an inner surface 1622 defining the lumen 1620. At the distal end portion 1612b, the elongated shaft 1612 may be open. The elongated shaft 1612 may be configured to slidably receive an elongated manipulation member 1613 configured to carry an expandable device 1600 such that the elongated manipulation member 1613 controls a position of the expandable device 1600 relative to the elongated shaft 1612. For example, the elongated manipulation member 1613 can be manipulated to move the expandable device 1600 distally through the lumen 1620 and/or to expel the expandable device 1600 from the lumen 1620 to expand or deploy the expandable device 1600 at a treatment site. Additionally or alternatively, the elongated manipulation member 1613 can be manipulated to resheath the expandable device 1600 into the lumen 1620 and/or draw the expandable device 1600 proximally through the lumen 1620. The elongated shaft 1612 can define a generally longitudinal dimension extending between the proximal end portion 1612a and the distal end portion 1612b. When the delivery system 1601 is in use, the longitudinal dimension need not be straight along some or any of its length.

The elongated manipulation member 1613 can be configured to selectively control movement and/or positioning of one or more portions of the expandable device 1600. The elongated manipulation member 1613 may comprise a distal portion 1613a, a first proximal portion 1613b, and/or a second proximal portion 1613c. The first and second proximal portions 1613b, 1613c may be radially spaced apart, as shown in FIG. 16. The first proximal portion 1613b may be configured to move the entire expandable device 1600 and/or a first articulating portion 1608a of the expandable device 1600 relative to the lumen 1620 of the elongated shaft 1612, whereas the second proximal portion 1613c may be configured to move a second articulating portion 1608b of the expandable device 1600 relative to the lumen 1620 of the elongated shaft 1612. The elongated manipulation member 1613 and/or any portion thereof can generally comprise any member(s) with sufficient flexibility and column strength to move the expandable device 1600 through the elongated shaft 1612. The elongated manipulation member 1613 can therefore comprise a wire, tube (e.g., hypotube), braid, coil, or other suitable member(s), or a combination of wire(s), tube(s), braid(s), coil(s), etc.

The delivery system 1601 can include a coupling assembly 1626 configured to releasably engage the expandable device 1600 to control a position of the expandable device 1600 with respect to the elongated manipulation member 1613 and/or the elongated shaft 1612. The elongated manipulation member 1613 can carry the coupling assembly 1626. The coupling assembly 1626 can be configured to engage the expandable device 1600, via abutment of the proximal edge of the expandable device 1600, mechanical interlock with the pores and filaments of the expandable device 1600, frictional engagement with the inner wall of the expandable device 1600, any combination of these modes of action, or another suitable mode of action. The coupling assembly 1626 can therefore cooperate with the inner surface 1622 of the elongated shaft 1612 to grip and/or abut the expandable device 1600 such that the coupling assembly 1626 can move the expandable device 1600 along and within the elongated shaft 1612, e.g., distal and/or proximal movement of the elongated manipulation member 1613 relative to the elongated shaft 1612 results in a corresponding distal and/or proximal movement of the expandable device 1600 within the elongated shaft lumen 1620.

In some embodiments, the coupling assembly 1626 can comprise one or more proximal restraints 1628 and/or a distal restraint 1630. The proximal and distal restraints 1628, 1630 can be fixed to one or more portions of the elongated manipulation member 1613 to prevent or limit proximal or distal movement of the coupling assembly 1626 along the longitudinal dimension of the elongated manipulation member 1613. For example, the proximal and distal restraints 1628, 1630 can be soldered, welded, adhered, etc. to one or more portions of the elongated manipulation member 1613. In some embodiments, the proximal restraint 1628 can be sized to abut a proximal end of the expandable device 1600 and be employed to push the device 1600 distally during delivery thereof.

As depicted in FIG. 16, the proximal restraint 1628 may be configured to abut the proximal end of the expandable device 1600. The proximal restraint 1628 may comprise a first portion 1628a carried by the first proximal portion 1613b of the elongated manipulation member 1613 and a second portion 1628b carried by the second proximal portion 1613c of the elongated manipulation member 1613. The first portion 1628a of the proximal restraint 1628 can be configured to bear distally against the first articulating portion 1608a of the expandable device 1600 to move the first articulating portion 1608a distally and the second portion 1628b of the proximal restraint 1628 can be configured to bear distally against the second articulating portion 1608b of the expandable device 1600 to move the second articulating portion 1608b distally. The second portion 1628b of the proximal restraint 1628 may be movable relative to the first portion 1628a of the proximal restraint 1628 along a longitudinal dimension of the device 1600. In this arrangement each portion 1628a, 1628b of the proximal restraint 1628 can be used to independently move (e.g., push) a corresponding articulating portion of the expandable device 1600. A push force can be applied to the first proximal portion 1613b of the elongated manipulation member 1613 such that the first portion 1628a of the proximal restraint 1628 abuts the first articulating portion 1608a of the expandable device 1600 and moves the entire expandable device 1600 or only the first articulating portion 1608a distally through the elongated shaft 1612. A push force can be applied to the second proximal portion 1613c of the elongated manipulation member 1613 such that the second portion 1628b of the proximal restraint 1628 abuts the second articulating portion 1608b of the expandable device 1600 and moves the second articulating portion 1608b distally through the elongated shaft 1612.

The coupling assembly 1626 can also include an engagement member 1632 carried by the elongated manipulation member 1613 between the proximal and distal restraints 1628, 1630. The engagement member 1632 can be a rigid plate, sprocket, pad, or other suitable member with a central aperture configured to receive the elongated manipulation member 1613 therethrough. The engagement member 1632 may be configured to frictionally engage, mechanically interlock with, or otherwise engage the expandable device 1600 such that the engagement member 1632 restrains the expandable device 1600 from moving longitudinally with respect to the elongated manipulation member 1613. One or more spacers (not shown) can be disposed about the elongated manipulation member 1613 between the engagement member 1632 and the proximal restraints 1628, the distal restraint 1630, and/or additional engagement members 1632 to define a relative longitudinal positioning of the components on either end of the spacer. The spacer can comprise a wire coil, a solid tube, or other structural element that can be mounted over the elongated manipulation member 1613. In some embodiments, the spacer can be a zero-pitch coil with flattened ends. In some embodiments, the spacer can be a solid tube (e.g., a laser-cut tube) that can be rotatably mounted or non-rotatably fixed (e.g., soldered) to the elongated manipulation member 1613. The spacers can have a radially outermost dimension that is smaller than a radially outermost dimension of the engagement member 1632 such that the spacer does not contact the expandable device 1600 during normal operation of the system 1601. Although the embodiment illustrated in FIG. 16 includes one engagement member 1632 and no spacers, the number of engagement members and spacers can vary. In at least one embodiment, the coupling assembly 1626 includes only a single engagement member 1632 without any spacers. In other embodiments, the number of engagement members can vary, for example two, three, four, five, six, or more engagement members separated by spacers.

When the proximal restraint 1628 is configured to push the expandable device 1600 distally, the proximal restraint accordingly transmits some, most, or all of the distal longitudinal (push) force to the expandable device 1600, wholly or partially in place of the engagement member(s) 1632. In such a configuration, the engagement member 1632 can transmit little or no push force to the expandable device 1600 while the expandable device 1600 is delivered distally along the length of the elongated shaft 1612. Advantageously, this can reduce or eliminate the tendency of the engagement member(s) 1632 to distort pores of the expandable device 1600. Use of the proximal restraint 1628 to move the expandable device 1600 in this manner can also reduce or eliminate longitudinal movement of the expandable device 1600 relative to the elongated manipulation members 1613 that sometimes accompanies the pore distortion described above. In most cases, the vast majority of the travel of the expandable device 1600 within the elongated shaft 1612 is in the distal or "push" direction during delivery to the treatment location, in contrast to the relatively short travel involved in resheathing the expandable device 1600, in the proximal or "pull" direction. Therefore, configuring the proximal restraint 1628 to transmit most or all of the push force to the expandable device 1600 can significantly reduce or substantially eliminate such distortion and/or relative longitudinal movement of the expandable device 1600.

The coupling assembly 1626 of FIG. 16 can therefore employ the proximal restraint 1628 as a pushing element to transmit at least some, or most or all, distally directed push force to the expandable device 1600 during delivery. In such a coupling assembly 1626, the engagement member(s) 1632 do not transmit any distally directed push force to the expandable device 1600 during delivery (or transmit only a small portion of such force, or do so only intermittently). The engagement member(s) 1632 can transmit proximally-directed pull force to the expandable device 1600 during retraction or resheathing, and the proximal restraint 1628 can transmit no proximally directed pull force to the stent (or it may do so occasionally or intermittently, for example when a portion of the expandable device 1600 becomes trapped between the outer edge of the proximal restraint 1628 and the inner wall of the elongated shaft 1612).

In some embodiments, the engagement member(s) 1632 are employed for both distal and proximal movement of the expandable device 1600 with respect to the elongated shaft 1612. The engagement member(s) 1632 can transmit distally directed force to the expandable device 1600 to move it distally within the elongated shaft 1612 during delivery, and proximally directed force to the expandable device 1600 to move it proximally into the elongated shaft 1612 during resheathing. In such embodiments, the proximal restraint 1628 can be made with a relatively small outer diameter, and/or be positioned sufficiently proximal of the proximal end of the expandable device 1600, to prevent the proximal restraint 1628 from transmitting distally directed push forces to the expandable device 1600 during delivery.

The engagement member 1632 can be fixed to the elongated manipulation member 1613 so as to be immovable relative to the elongated manipulation member 1613, in a longitudinal/sliding manner and/or in a radial/rotational manner. Alternatively, the engagement member 1632 can be coupled to (e.g., mounted on) the elongated manipulation member 1613 so that the engagement member 1632 can rotate about the longitudinal axis of the elongated manipulation member 1613, and/or move or slide longitudinally along the elongated manipulation member 1613. In such embodiments, the engagement member 1632 can have an inner lumen or aperture that receives the elongated manipulation member 1613 therein such that the engagement member 1632 can slide and/or rotate relative to the elongated manipulation member 1613.

In some embodiments, the engagement member 1632 can be mounted onto the elongated manipulation member 1613 to permit not only rotational movement but also a degree of tilting of the engagement member 1632 with respect to a longitudinal axis of the elongated manipulation member 1613. For example, a hole in the engagement member 1632 can be larger than the outer diameter of the corresponding portion of the elongated manipulation member 1613, thereby permitting both rotational movement and tilting with respect to the elongated manipulation member 1613. "Tilting" as used herein means that the long axis of the engagement member 1632 (i.e., an axis extending along the longest dimension of the engagement member 1632, substantially parallel to the proximal-facing and distal-facing end faces of the engagement member 1632) is non-orthogonal to a longitudinal axis of the elongated manipulation member 1613. For example, in one tilted configuration, the long axis of the engagement member 1632 can intersect the elongated manipulation member 1613 at approximately 85 degrees, indicating 5 degrees of tilt. Depending on the dimensions of the engagement member 1632 and the elongated manipulation member 1613, the degree of tilting permitted can vary. In some embodiments, the engagement member 1632 can tilt with respect to the elongated manipulation member 1613 by 30 degrees or less, 20 degrees or less, 10 degrees or less, or 5 degrees or less. In some embodiments, the engagement member 1632 can tilt with respect to the elongated manipulation member by at least 5 degrees, by at least 10 degrees, by at least 20 degrees, or more.

Proper positioning of an expandable device of the present technology requires an articulating portion to be oriented adjacent to the vessel it is intended to be expanded into. The delivery system 1601 can comprise an orientation member 1634 to facilitate rotation of the expandable device 1600 during delivery thereof. The orientation member 1634 can be coupled to the first and/or second proximal portions 1613b, 1613c of the elongated manipulation member 1613. In some embodiments, the orientation member 1634 is fixed to the first proximal portion 1613b of the elongated manipulation member 1613 and is slidable over the second proximal portion 1613c of the elongated manipulation member 1613. As a result, the first and second proximal portions 1613b and 1613c can be slidably moved relative to one another.

The orientation member 1634 can comprise a proximal end face 1634a, a distal end face 1634b, and an outer surface 1634c extending therebetween. As shown in FIG. 16, the proximal end face 1634a of the orientation member 1634 can be positioned within the lumen 1620 of the elongated shaft 1612. In some embodiments, the proximal end face 1634a of the orientation member 1634 is positioned distal of the proximal end portion 1612a of the elongated shaft 1612. A length of the orientation member 1634 and/or a position of the proximal end face 1634a of the orientation member 1634 relative to the elongated shaft 1612 can be selected based on a desired ability to torque the elongated manipulation member 1613 and thereby the expandable device 1600 (e.g., the length can be greater and/or the proximal end face 1634a can be positioned further proximally to enhance the ability of the orientation member 1634 to transmit torque to the elongated manipulation member 1613).

As shown in FIG. 16, in some embodiments the orientation member 1634 defines a first lumen 1634d configured to receive the first proximal portion 1613b of the elongated manipulation member 1613 and/or a second lumen 1634e configured to receive the second proximal portion 1613c of the elongated manipulation member 1613. The first lumen 1634d can have a diameter greater than an outer diameter of the first proximal portion 1613b such that the first proximal portion 1613c is slidable and/or rotatable in the first lumen 1634d and/or the second lumen 1634e can have a diameter greater than an outer diameter of the second proximal portion 1613c such that the second proximal portion 1613c is slidable and/or rotatable in the second lumen 1634e. In some embodiments, the first proximal portion 1613b can be fixedly positioned within the first lumen 1634d (e.g., via interference fit, adhesive, etc.) such that the first proximal portion 1613c is not slidable and/or is not rotatable relative to the first lumen 1634d. Additionally or alternatively, the second proximal portion 1613c can be fixedly positioned within the second lumen 1634e (e.g., via interference fit, adhesive, etc.) such that the second proximal portion 1613c is not slidable and/or is not rotatable relative to the second lumen 1634e.

In operation, the expandable device 1600 can be moved distally or proximally within the elongated shaft 1612 via the elongated manipulation member 1613 and the coupling assembly 1626. To move the expandable device 1600 out of the elongated shaft 1612, either one or both proximal portions of the elongated manipulation member 1613 are moved distally while the elongated shaft 1612 is held stationary or the one or more proximal portions of the elongated manipulation member 1613 are held stationary while the elongated shaft 1612 is withdrawn proximally. When the proximal portion(s) of the elongated manipulation member 1613 are moved distally, the distal face of the proximal restraint 1628 bears against the proximal end of the expandable device 1600 and causes the expandable device to be advanced distally, and ultimately out of the distal portion 1618 of the elongated shaft 1612. In embodiments wherein the engagement member(s) 1632 is employed to transmit pushing force to the expandable device 1600, the mechanical engagement or interlock between the engagement member 1632 and the expandable device 1600, in response to the application of a distally directed force to the elongated manipulation member 1613, causes the expandable device 1600 to move distally through and out of the elongated shaft 1612. Conversely, to resheath or otherwise move the expandable device 1600 into the elongated shaft 1612, the relative movement between the elongated manipulation member 1613 and the elongated shaft 1612 is reversed compared to moving the expandable device 1600 out of the elongated shaft such that the proximal region of the distal restraint 1630 bears against the distal end of the expandable device and thereby causes the engagement member 1632 to be retracted relative to the elongated shaft 1612. The mechanical engagement between the engagement member 1632 and the expandable device 1600 may accordingly hold the expandable device 1600 with respect to the elongated manipulation member 1613 such that proximal movement of the expandable device 1600 relative to the elongated shaft 1612 enables re-sheathing of the expandable device 1600 back into the lumen 1620 of the elongated shaft 1612. This can be useful when the expandable device 1600 has been partially deployed and a portion of the expandable device 1600 remains disposed between the engagement member 1632 and the inner surface 1622 of the elongated shaft 1612 because the expandable device 1600 can be withdrawn back into the distal opening of the elongated shaft 1612 by moving the elongated manipulation member 1613 proximally relative to the elongated shaft 1612 (and/or moving the elongated shaft 1612 distally relative to the elongated manipulation member 1613). Resheathing in this manner remains possible until the engagement member 1632 and/or elongated shaft 1612 have been moved to a point where the engagement member 1632 is beyond the distal opening of the elongated shaft 1612 and the expandable device 1600 is released from between the engagement member 1632 and the elongated shaft 1612.

In some embodiments, delivering an expandable device of the present technology can begin with obtaining percutaneous access to the patient's arterial system, typically via a major blood vessel in a leg or arm. A guidewire can be placed through the percutaneous access point and advanced to the treatment location, which can be in an intracranial artery, or any neurovascular artery, peripheral artery, or coronary artery. The elongated shaft 1612 (e.g., a microcatheter) can be advanced over the guidewire to a treatment site including an aneurysm at a vessel bifurcation. The distal portion 1612b of the elongated shaft 1612 can be advanced into the first branching vessel. The guidewire can then be withdrawn from the elongated shaft 1612 and the elongated manipulation member 1613 and core assembly 1626, together with the expandable device 1600 mounted thereon or supported thereby, can be advanced through the elongated shaft 1612 to the distal portion 1612b of the elongated shaft 1612. Radiopaque markers of the expandable device 1600 can be visualized with fluoroscopy to identify the orientation and/or position of the expandable device 1600 at the treatment site. For example, the elongated manipulation member 1613 can carry a marker 1636 to facilitate visualization of the system 1601 during use. In some embodiments, the marker 1636 is located at a longitudinal position between the distal portion 1613a and the proximal portions 1613b, 1613c of the elongated manipulation member 1613. The orientation member 1634 can be used to rotate the expandable device 1600 within the elongated shaft 1612 and/or within the vessel to achieve the proper rotational orientation. A first (e.g., distal) end portion 1604 of the expandable device 1600 can be expanded within the first branching vessel as previously described by applying a push force to the first proximal portion 1613b of the elongated manipulation member 1613. The expandable device 1600 may self-expand into apposition with the inner wall of the first branching blood vessel. In some embodiments, an additional expansion device (e.g., balloon, energy source) can be used to facilitate or cause expansion of the device 1600. In some embodiments, once the first portion 1604 of the expandable device 1600 is deployed, the second articulating portion 1608b may be deployed into the second branching blood vessel. A force can be applied to the second proximal portion 1613c of the elongated manipulation member 1613 to cause the second portion 1628b of the proximal restraint 1628 to move the second articulating portion 1608b into the second branching blood vessel. For example, the second portion 1628b of the proximal restraint 1628 can be distally advanced relative to the first portion 1628a. By virtue of this distal advancement, the second portion 1628b of the proximal restraint can urge the second articulating portion 1608b radially outwardly. The second articulating portion 1608b can expand into apposition with the inner wall of the second branching blood vessel so that at least a portion of the first portion 1604 and/or the second articulating portion 1608b is positioned across the neck of an aneurysm between the first and second branching blood vessels. The first articulating portion 1608a may be advanced out of the elongated shaft 1612 and expanded into apposition with the inner wall of the parent blood vessel. The delivery system 1601 can be removed from the patient, leaving the implanted expandable device 1600 positioned within the parent and branching vessels and across the neck of the bifurcation aneurysm.

Figure 17:
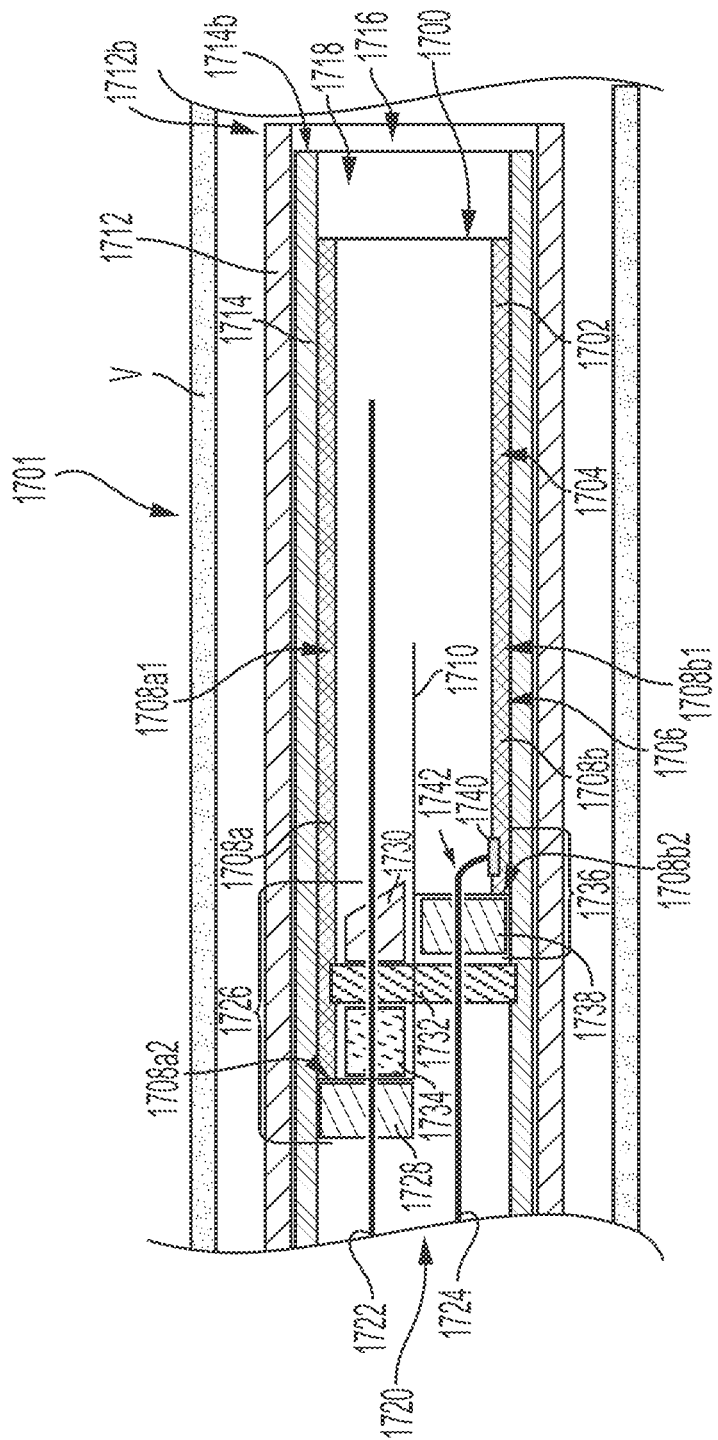
FIG. 17 is a schematic, cross-sectional side view of a delivery system in accordance with embodiments of the present technology.

FIG. 17 is a side cross-sectional view of an example of a system 1701 for delivering an expandable device 1700 to a treatment site within a patient's vasculature to treat a bifurcation aneurysm. FIG. 17 depicts the system 1701 positioned within a blood vessel V. The expandable device 1700 can be similar to other expandable devices disclosed herein. For example, as shown in FIG. 17, the expandable device 1700 can comprise a mesh 1702 having a first portion 1704 and a second portion 1706 extending away from the first portion 1704 and comprising a first articulating portion 1708a and a second articulating portion 1708b. The first and second articulating portions 1708a, 1708b can be separated by one or more slits 1710. In various embodiments, each of the first articulating portion 1708a and the second articulating portion 1708b comprises a first end 1708a1, 1708b1 at the first portion 1704 and a free second end 1708a2, 1708b2. As previously described and as shown in FIG. 17, in some embodiments the second articulating portion 1708b is shorter than the first articulating portion 1708a.

The system 1701 can comprise a first elongated shaft 1712 and/or a second elongated shaft 1714. The first elongated shaft 1712 can have a proximal end portion (not shown in FIG. 17), a distal end portion 1712b configured to be positioned at or near the treatment site, a longitudinal axis extending between the proximal end portion and the distal end portion 1712b, and a lumen 1716 defined by a sidewall of the first elongated shaft 1712. The second elongated shaft 1714 can have a proximal end portion (not shown in FIG. 17), a distal end portion 1714b configured to be positioned at or near the treatment site, a longitudinal axis extending between the proximal end portion and the distal end portion 1714b, and a lumen 1718 defined by a sidewall of the second elongated shaft 1714. As shown in FIG. 17, an outer diameter of the second elongated shaft 1714 can be no greater than (or smaller than) a diameter of the lumen 1716 of the first elongated shaft 1712 such that the second elongated shaft 1714 can be received within and through the lumen 1716 of the first elongated shaft 1712. In some embodiments, the first elongated shaft 1712 and/or the second elongated shaft 1714 comprises a distal access catheter having an inner diameter of about 0.09 inches or less (e.g., 0.071 inches, 0.068 inches, 0.0445 inches, etc.). In various embodiments, the first elongated shaft 1712 and/or the second elongated shaft 1714 has an outer diameter of about 7 French or less (e.g., about 7 French, about 6 French, about 5 French, about 4 French, about 3 French, about 2 French, about 1 French, etc.). Additionally or alternatively, the first elongated shaft 1712 and/or the second elongated shaft 1714 can comprise a microcatheter having an inner diameter of about 0.030 inches or less (e.g., 0.027 inches, 0.021 inches, 0.017 inches, etc.), and/or an outer diameter of 3 French or less near the distal end portion of the shaft.

As shown in FIG. 17, the expandable device 1700 can be positioned within the lumen 1718 of the second elongated shaft 1714. Additionally or alternatively, the expandable device 1700 can be positioned within the lumen 1716 of the first elongated shaft 1712. In any case, when the expandable device 1700 is in a constrained configuration (e.g., as shown in FIG. 17, within the lumen 1718 of the second elongated shaft 1714, etc.) the first portion 1704 of the mesh 1702 of the device 1700 can be positioned distal of the second portion 1706. In some embodiments, when the expandable device 1700 is in the constrained configuration, the second end 1708a2 of the first articulating portion 1708a is located proximal of the second end 1708b2 of the second articulating portion 1708b. The expandable device 1700 can be advanced distally through the first elongated shaft 1712, the second elongated shaft 1714, the blood vessel V, etc. with the first portion 1704 of the expandable device 1700 as a leading portion of the device 1700.

Figure 19:
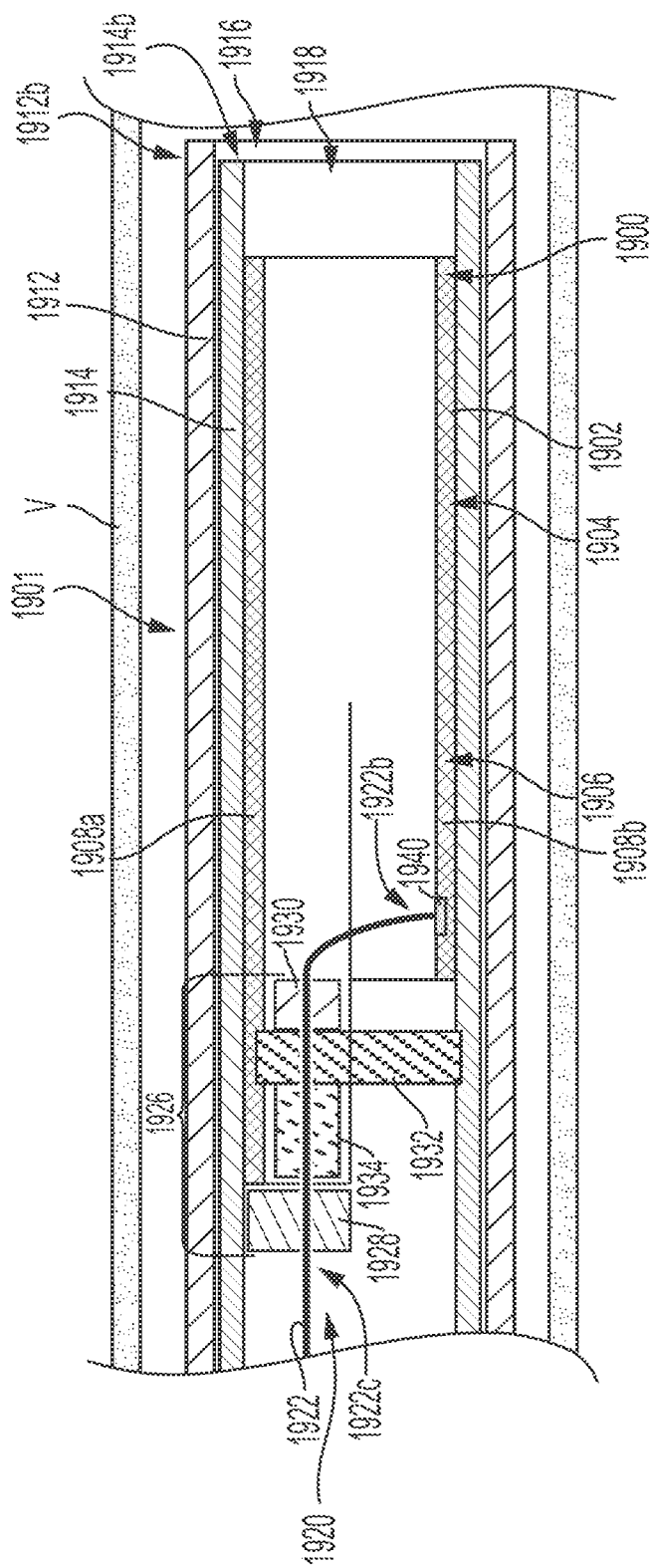
FIG. 19 is a schematic, cross-sectional side view of a delivery system in accordance with embodiments of the present technology.

The expandable device 1700 can be carried by a core assembly 1720 extending through a lumen of the expandable device 1700. The core assembly 1720 can comprise one or more elongated manipulation members. For example, as shown in FIG. 17, the core assembly 1720 can comprise a first elongated manipulation member 1722 and a second elongated manipulation member 1724. In some embodiments, the first elongated manipulation member 1722 is configured to releasably engage the first articulating portion 1708a (whether directly or indirectly) to cause a desired movement of the first articulating portion 1708a relative to the first elongated shaft 1712 and/or the second elongated shaft 1714. The second elongated manipulation member 1724 can be configured to releasably engage the second articulating portion 1708b (whether directly or indirectly) to cause a desired movement of the second articulating portion 1708b relative to the first elongated shaft 1712 and/or the second elongated shaft 1714. Although FIG. 17 shows two elongated manipulation members, a system of the present technology can comprise any suitable number of elongated manipulation members (e.g., one elongated manipulation member as shown in FIG. 19, more than two elongated manipulation members, etc.). In some embodiments, the number of elongated manipulation members a system includes is the same as the number of articulating portions of an expandable member to be used with the system. In some embodiments, a system includes more or fewer elongated manipulation members than the number of articulating portions of an expandable member to be used with the system.

The first elongated manipulation member 1722 and/or the second elongated manipulation member 1724 can generally comprise any elongated member(s) with sufficient flexibility and column strength to move the expandable device 1700 through a lumen of an elongated shaft. For example, the first elongated manipulation member 1722 and/or the second elongated manipulation member 1724 can comprise a wire, tube (e.g., hypotube), braid, coil, or other suitable member (s), or a combination of wire(s), tube(s), braid(s), coil(s), etc. In some embodiments, the first elongated manipulation member 1722 and/or the second elongated manipulation member 1724 can comprise a tube surrounding a wire along at least a portion of the length of the wire. The first elongated manipulation member 1722 and/or the second elongated manipulation member 1724 can comprise a lubricious material, such as PTFE (polytetrafluoroethylene or TEFLON™) or other polymers, positioned on at least a portion of the tube and/or the wire. A diameter of the first elongated manipulation member 1722 and/or the second elongated manipulation member 1724 may vary and/or taper along some or all of its length. The first elongated manipulation member 1722 and/or the second elongated manipulation member 1724 may include one or more fluorosafe and/or radiopaque markers (not shown) comprising a band, a deposited material, an exposed portion of the elongated manipulation member, etc. In some embodiments, the distal end portion of the first elongated manipulation member 1722 and/or the second elongated manipulation member 1724 can comprise and/or carry a coil, which can facilitate navigation of the system 1701 through the vasculature and/or visualization of the system 1701.

In some embodiments, the first elongated manipulation member 1722 carries a first coupling assembly 1726 configured to engage the first articulating portion 1708a. The first coupling assembly 1726 can be configured to engage the expandable device 1700 via mechanical interlock with pores and filaments of the mesh 1702, abutment of the second end 1708a2 of the first articulating portion 1708a, frictional engagement with the inner surface of the first articulating portion 1708a, or any combination of these modes of action. The coupling assembly 1726 can cooperate with the overlying second elongated shaft 1714 to grip and/or abut the first articulating portion 1708a such that the coupling assembly 1726 can move the first articulating portion 1708a along and within the lumen 1718 of the second elongated shaft 1714, e.g., distal and/or proximal movement of the first coupling assembly 1726 (e.g., via distal and/or proximal movement of the first elongated manipulation member 1722) relative to the second elongated shaft 1714 results in a corresponding distal and/or proximal movement of the first articulating portion 1708a within the lumen 1718 of the second elongated shaft 1714. Such distal and/or proximal movement of the first articulating portion 1708a can cause a corresponding distal and/or proximal movement of the first portion 1704 of the expandable device 1700.

As shown in FIG. 17, the first coupling assembly 1726 can comprise a proximal restraint 1728, a distal restraint 1730, an engagement member 1732, and/or a spacer 1734, each disposed on the first elongated manipulation member 1722. The first coupling assembly 1726 can be configured to engage the first articulating portion 1708a to push and/or pull the first articulating portion 1708a distally and/or proximally through the lumen 1718 of the second elongated shaft 1714. For example, the proximal restraint 1728 can be configured to apply a distally directed force to the proximal end of the first articulating portion 1708a to push the first articulating portion 1708a (and thereby the first portion 1704 of the device 1700) distally and/or through the lumen 1718 of the second elongated shaft 1714. Additionally or alternatively, the engagement member 1732 can be configured to apply a proximally directed force to the first articulating portion 1708a to push the first articulating portion 1708a (and thereby the first portion 1704 of the device 1700) distally and/or through the lumen 1718 of the second elongated shaft 1714. In some embodiments, the distal restraint 1730 is configured to prevent or limit distal motion of the engagement member 1732 relative to the first elongated manipulation member 1722 and/or proximal restraint 1730. The spacer 1734 can be configured to define a minimum longitudinal spacing between two adjacent components of the first coupling assembly 1726. For example, as shown in FIG. 17, the spacer 1734 can define a minimum spacing between the proximal restraint 1728 and the engagement member 1732. In some embodiments, the first coupling assembly 1726 can comprise a spacer between the engagement member 1732 and the distal restraint 1730.

The proximal restraint 1728 can be configured to abut and/or contact the proximal end of the first articulating portion 1708a such that distal advancement of the proximal restraint 1728 (e.g., via distal advancement of the first elongated manipulation member 1722) applies a distally directed force to the first articulating portion 1708a, thereby moving the first articulating portion 1708a and/or the first portion 1704 distally through the lumen 1718. In some embodiments, the proximal restraint 1728 is substantially fixed in place while the second elongated shaft 1714 is retracted proximally so that the relative positions of the expandable device 1700 and the second elongated shaft 1714 are modified. Distal movement of the first portion 1704 of the expandable device 1700 relative to the second elongated shaft 1714 (e.g., via distally directed forces applied to the first articulating portion 1708a by the proximal restraint 1728, etc.) can expel the first portion 1704 through the opening at the distal end portion 1714b of the second elongated shaft 1714. In some embodiments, the first portion 1704 can be expelled from the second elongated shaft 1714 before the first articulating portion 1708a is expelled from the second elongated shaft 1714.

In some embodiments, the proximal restraint 1728 comprises a distal-facing surface configured to engage a proximal end region of the first articulating portion 1708a. For example, the proximal restraint 1728 can comprise a partial cylinder with a proximal-facing surface and a distal-facing surface. The proximal restraint 1728 can have an outer diameter at least as large as an outer diameter of the first articulating portion 1708a such that a distal-facing surface of the proximal restraint 1728 is configured to contact a proximal edge and/or surface of the first articulating portion 1708a. In some embodiments, the proximal restraint 1728 has an outer diameter that is smaller than a diameter of the lumen 1718 of the second elongated shaft 1714 such that, when the proximal restraint 1728 is positioned within the lumen 1718, a radial gap exists between an outer edge of the proximal restraint 1728 and the inner surface of the second elongated shaft 1714. According to various embodiments, the proximal restraint 1728 can have a cross-sectional shape corresponding, at least in part, to a cross-sectional shape of the first articulating portion 1708*a*. For example, in embodiments in which an outer surface of the first articulating portion 1708*a* subtends an angle of about 180 degrees, the proximal restraint 1728 can have an outer surface subtending about 180 degrees (e.g., the proximal restraint 1728 can comprise a half cylinder). In various embodiments, the proximal restraint 1728 can have an outer surface subtending an angle less than 180 degrees or more than 180 degrees. The proximal restraint 1728 can comprise a complete cylinder, a partial cylinder, or another suitable shape. In any case, the proximal restraint 1728 can be carried by the first elongated manipulation member 1722 such that distal movement of the first elongated manipulation member 1722 can cause the proximal restraint 1728 to move distally and transmit distally directed push force to the expandable device 1700.

The distal restraint 1730 can be configured to define a maximum longitudinal spacing between the proximal restraint 1728 and the engagement member 1732 and/or prevent or limit distal motion of the engagement member 1732 with respect to the first elongated manipulation member 1722. In various embodiments, the distal restraint 1730 has a fixed position along a length of the first elongated manipulation member 1722 and/or relative to the proximal restraint 1728. For example, the distal restraint 1730 can be welded, soldered, and/or adhered to the first elongated manipulation member 1722. In some embodiments, the distal restraint 1730 is sized to avoid or limit contact with an inner surface of the expandable device 1700 during use of the system 1701, as such contact can cause unintentional deformation of the expandable device 1700 and/or an increase in delivery and/or resheathing forces. In various embodiments, at least a portion of the distal restraint 1730 can taper inwardly in a distal direction and/or the distal restraint 1730 can have an outer diameter less than the inner diameter of the expandable device 1700.

The engagement member 1732 can be configured to apply an outward radial force to the first articulating portion 1708*a* and the second elongated shaft 1714 when compressed within the lumen 1718 of the second elongated shaft 1714. As a result, when the first elongated manipulation member 1722 and the engagement member 1732 are drawn proximally, the engagement member 1732 can apply a proximally directed force to the first articulating portion 1708*a*. Such proximally directed forces can cause proximal motion of the first articulating portion 1708*a* and can facilitate resheathing of a partially deployed expandable device 1700 into and/or through the lumen 1718 of the second elongated shaft 1714. The engagement member 1732 can engage an inner surface of the first articulating portion 1708*a*. For example, the engagement member 1732 can comprise a polymeric pad having an outer radial dimension slightly larger than an inner radial dimension of the expandable device 1700 in the constrained configuration. In some embodiments, the engagement member 1732 comprises a sprocket having radial projections configured to extent through pores of the expandable device 1700 to retain the expandable device 1700 at a desired position. According to various embodiments, the engagement member 1732 can comprise a resilient offset coil configured to engage an inner surface of the expandable device 1700. The first coupling assembly 1726 (or any component thereof) can be similar to any corresponding coupling assembly or component disclosed in U.S. patent application Ser. No. 15/410,444, filed Jan. 19, 2017, U.S. patent application Ser. No. 15/459,118, filed Jul. 1, 2019, U.S. patent application Ser. No. 17/248,637, filed Feb. 1, 2021, U.S. patent application Ser. No. 15/951,779, filed Apr. 12, 2018, U.S. patent application Ser. No. 17/249,755, filed April Mar. 11, 2021, U.S. patent application Ser. No. 15/951,890, filed Apr. 12, 2018, U.S. patent application Ser. No. 16/947,811, filed Aug. 18, 2020, U.S. patent application Ser. No. 15/951,967, filed Apr. 12, 2018, U.S. patent application Ser. No. 15/952,001, filed Apr. 12, 2018, and/or U.S. patent application Ser. No. 17/249,010, filed Feb. 17, 2021, each of which is incorporated by reference herein in its entirety.

As shown in FIG. 17, the core assembly 1720 can comprise a second elongated manipulation member 1724 configured to engage the second articulating portion 1708*b* of the mesh 1702. The second elongated manipulation member 1724 can be similar to the first elongated manipulation member 1722. For example, the second elongated manipulation member 1724 can comprise any elongated member(s) with sufficient flexibility and column strength to move the expandable device 1700 through a lumen of an elongated shaft. The second elongated manipulation member 1724 can have sufficient column strength to move the expandable device 1700 through the lumen 1718 of the second elongated shaft 1714 when advanced in conjunction with the first elongated manipulation member 1722. In various embodiments, the second elongated manipulation member 1724 can be longitudinally coupled to the first manipulation member 1722 such that distal advancement of the first manipulation member 1722 causes distal movement of the second elongated manipulation member 1724. The second elongated manipulation member 1724 can carry a second coupling assembly 1736, which can be similar to the first coupling assembly 1726. For example, the second coupling assembly 1736 can include a proximal restraint 1738 positioned proximally of a proximal end of the second articulating portion 1708*b*, which can be similar to the proximal restraint 1728 carried by the first elongated manipulation member 1722. However, the second coupling assembly 1736 can differ from the coupling assembly 1726. For example, as shown in FIG. 17, the second coupling assembly 1736 may not include a distal restraint, an engagement member, and/or a spacer. In such embodiments (and others), a second coupling assembly 1736 including only a proximal restraint 1738 may be configured to facilitate distal advancement of the second articulating portion 1708*b*.

To facilitate resheathing, rotating, or otherwise positioning the second articulating portion 1708*b*, the second elongated manipulation member 1724 can be secured to the second articulating portion 1708*b* at an attachment 1740. The attachment 1740 can be located at an inner surface of the second articulating portion 1708*b*, at a proximal end of the second articulating portion 1708*b*, and/or at another suitable location. At the attachment 1740, the second elongated manipulation member 1724 can be directly secured to the second articulating portion 1708*b* or can be secured to the second articulating portion 1708*b* via one or more fasteners. According to various embodiments, the second elongated manipulation member 1724 is releasably secured to the second articulating portion 1708*b* at the attachment 1740. For example, the attachment 1740 can comprise an electrolytic detachment mechanism, a mechanical detachment mechanism, or another actuatable detachment mechanism.

In some embodiments, the attachment 1740 and/or the second coupling assembly 1736 enables movement of the second elongated manipulation member 1724 along one, two, three, four, five, or six degrees of freedom to be transmitted to the second articulating portion 1708*b*. The second elongated manipulation member 1724 can comprise a radial bend 1742 at or near a distal end portion of the second elongated manipulation member 1724. Such a radial bend 1742 can facilitate steering and/or delivery of the second articulating portion 1708*b* into a second branching blood vessel B2, which can facilitate accurate axial and rotational positioning of the second articulating portion 1708*b* at a desired position within a blood vessel and/or across a neck of an aneurysm. For example, distal movement of the second elongated manipulation member 1724 can cause distal movement of the second articulating portion 1708*b*, which can facilitate expelling of the second articulating portion 1708*b* out of the second elongated shaft 1714. Additionally or alternatively, proximal movement of the second elongated manipulation member 1724 can cause proximal movement of the second articulating portion 1708*b*, which can facilitate resheathing of the second articulating portion 1708*b* into the second elongated shaft 1714. In various embodiments, rotation of the second elongated manipulation member 1724 can cause and/or facilitate rotation of the second articulating portion 1708*b*, which can facilitate rotation of the second articulating portion 1708*b* during deployment to position the second articulating portion 1708*b* across a neck of an aneurysm and/or into a branching blood vessel.

As shown in FIG. 17, in some embodiments the second elongated manipulation member 1724 comprises a radial bend, which can facilitate advancing and/or steering the second articulating portion 1708*b* into a second branching blood vessel. For example, the second elongated manipulation member 1724 can be rotated by a user to aim the distal end of the second elongated manipulation member 1724 towards the second branching blood vessel. The second elongated manipulation member 1724 can then be distally advanced to advance the second articulating portion 1708*b* towards the second branching blood vessel. Such configuration may be particularly advantageous when the second branching blood vessel is located in a different plane than the first branching blood vessel and/or the parent blood vessel.

FIGS. 18A-18G illustrate various stages of a method of delivering the expandable device 1700 of FIG. 17 at a treatment site within a patient's vasculature using the system 1701. As described herein, the treatment site can comprise a blood vessel bifurcation in which a parent blood vessel P branches into a first branching blood vessel B1 and a second branching blood vessel B2. The expandable device 1700 can be configured to be positioned over a neck of an aneurysm A, which can be positioned between the parent blood vessel P, the first branching blood vessel B1, and/or the second branching blood vessel B2.

Figure 18A:
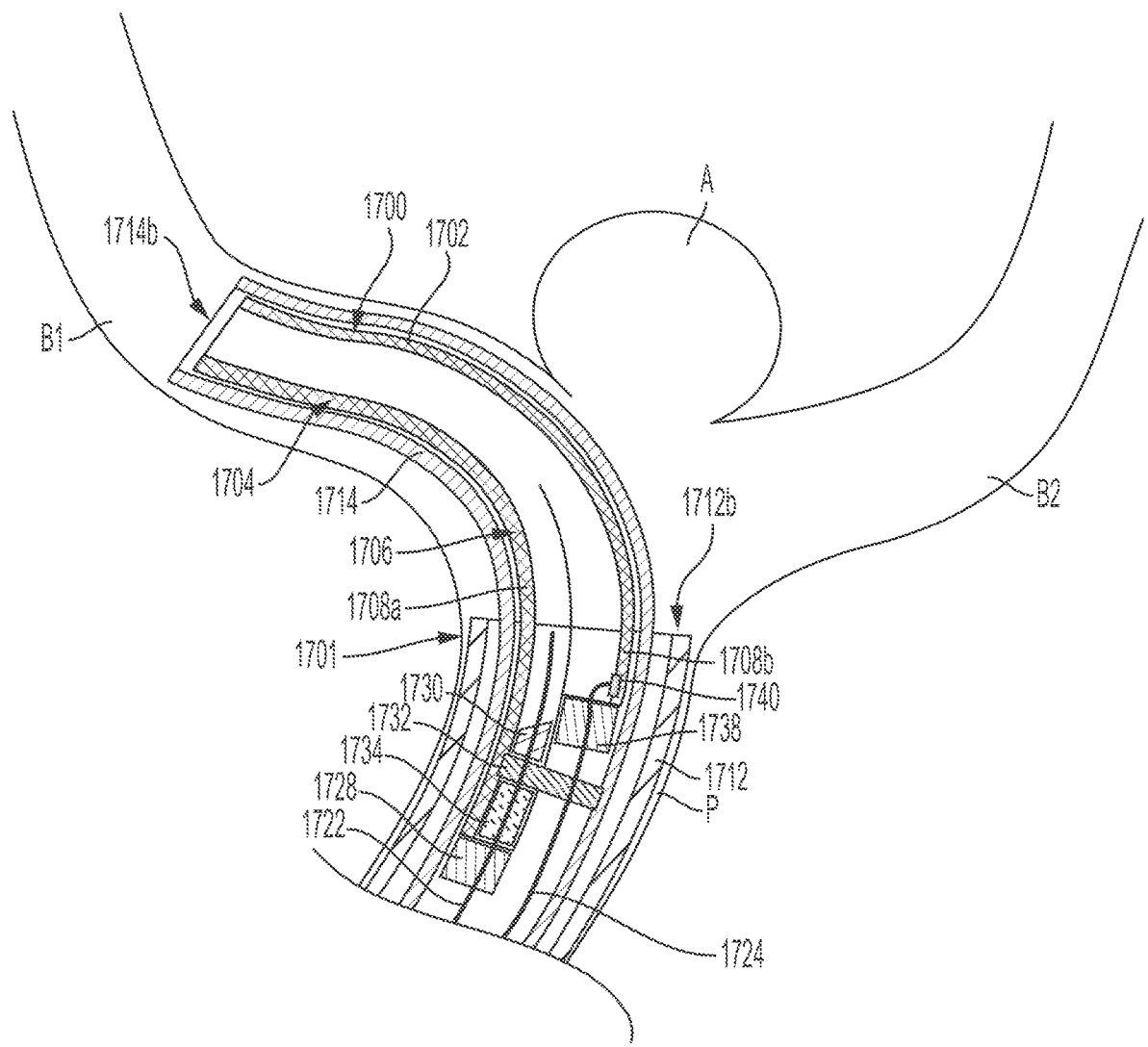
FIGS. 18A-18G illustrate various stages of a method of delivering an expandable device to a blood vessel bifurcation in accordance with embodiments of the present technology.

As shown in FIG. 18A, a method of deploying the expandable device 1700 can comprise advancing the distal end portion 1712*b* of the first elongated shaft 1712 to the parent blood vessel P. Additionally or alternatively, the distal end portion 1712*b* of the first elongated shaft 1712 can be advanced to the first branching blood vessel B1 and/or the second branching blood vessel B2. Although not shown in FIGS. 18A-18G, in some embodiments one or more components of the system 1701 can be distally advanced over a guidewire that has been advanced through the patient's vasculature. For example, a guidewire can be advanced through the patient's vasculature to the parent blood vessel P and/or one or more blood vessels distal of the parent blood vessel P. The first elongated shaft 1712 can then be advanced distally through the patient's vasculature over the guidewire. The first elongated shaft 1712 can provide a conduit for advancing the second elongated shaft 1714 and the expandable device 1700 to the treatment site. The distal end portion 1714*b* of the second elongated shaft 1714 can be advanced through the lumen 1716 of the first elongated shaft 1712. In some embodiments, the distal end portion 1714*b* of the second elongated shaft 1714 is positioned distal of the distal end portion 1712*b* of the first elongated shaft 1712. For example, as shown in FIG. 18A, the distal end portion 1714*b* of the second elongated shaft 1714 can be positioned within the first branching blood vessel B1.

As shown in FIG. 18A, the expandable device 1700 can be positioned at the distal end portion 1714*b* of the second elongated shaft 1714. The expandable device 1700 (including the first coupling assembly 1726 and the second coupling assembly 1736) can be distally advanced to the distal end portion 1714*b* of the second elongated shaft 1714 after the distal end portion 1714*b* has been positioned within the first branching blood vessel B1, or the expandable device 1700 and coupling assemblies 1726, 1736 can be advanced distally along with and in a fixed position relative to the second elongated shaft 1714. In any case, the first portion 1704 of the expandable device 1700 can be positioned within the first branching blood vessel B1 within the lumen 1718 of the second elongated shaft 1714.

Figure 18B:
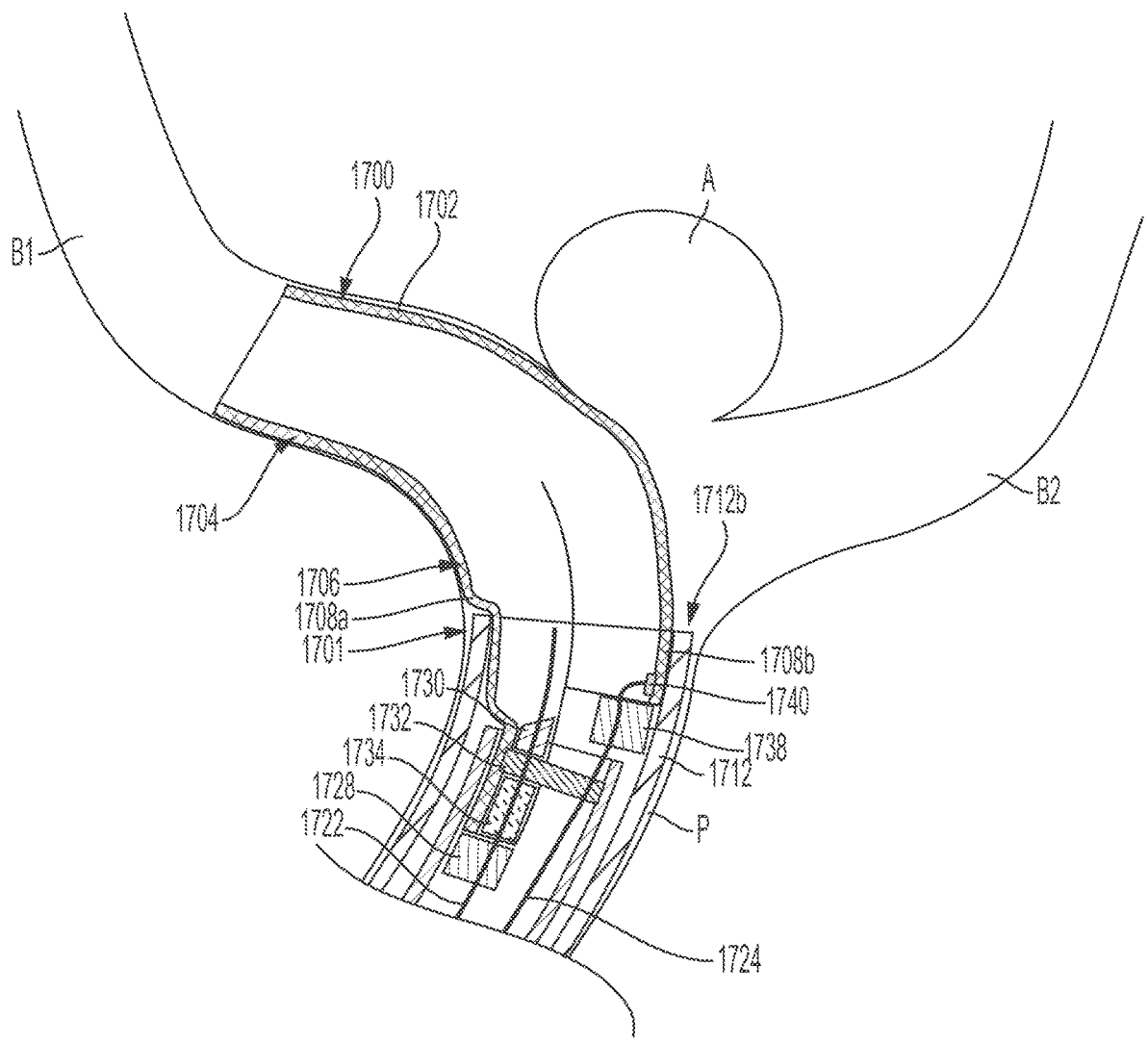

The first portion 1704 of the expandable device 1700 can be expelled from the lumen 1718 of the second elongated shaft 1714 and deployed in the patient's vasculature by moving the first portion 1704 distally out of the distal end portion 1714*b* of the second elongated shaft 1714. FIG. 18B shows the first portion 1704 deployed within the first branching blood vessel B1 such that the first portion 1704 has radially expanded into contact with the wall of the first branching blood vessel B1. To expel the first portion 1704 from the lumen 1718, the expandable device 1700 can be moved distally relative to the second elongated shaft 1714 and/or the second elongated shaft 1714 can be moved proximally relative to the expandable device 1700. As described herein, the mesh 1702 of the expandable device 1700 can be resilient such that the first portion 1704 is in a constrained state while positioned within the lumen 1718 of the second elongated shaft 1714 and expands to an expanded state once expelled from the lumen 1718. According to various embodiments, a radial dimension of the first portion 1704 can increase from the constrained state to the expanded state. In some embodiments, a radial dimension of the first portion 1704 in the unconstrained, expanded state is greater than a diameter of the lumen of the first branching blood vessel B1. As such, the first portion 1704 can be configured to apply a radially outward force to the first branching blood vessel B1 in the expanded state.

As shown in FIG. 18B, the first portion 1704 of the expandable device 1700 can be expelled from the second elongated shaft 1714 by retracting the second elongated shaft 1714 proximally relative to the expandable device 1700. In such embodiments (and others), the second elongated shaft 1714 can be proximally retracted (and/or the first and second elongated manipulation members 1722, 1724 can be manipulated) such that its distal end portion 1714*b* is positioned proximal the second end 1708*b*2 of the second articulating portion 1708*b* but distal of the second end 1708*a*2 of the first articulating portion 1708*a* and the engagement member 1732 of the first coupling assembly 1726. As previously described, the engagement member 1732 can be configured to cooperate with the second elongated shaft 1714 to engage the first articulating portion 1708*a*. Thus, while the engagement member 1732 and the second end 1708*a*2 of the first articulating portion 1708*a* are positioned within the lumen 1718 of the second elongated shaft 1714, the first coupling assembly 1726 retains its ability to distally advance and/or resheath the first articulating portion 1708a.

Because the attachment 1740 between the second elongated manipulation member 1724 and the second articulating portion 1708b can be selectively detachable, the second articulating portion 1708b may not separate from the second elongated manipulation member 1724 upon release from the lumen 1718 of the second elongated shaft 1714. Thus, the second elongated manipulation member 1724 can be distally advanced and/or rotated to urge the second articulating portion 1708b distally within the patient's vasculature and/or towards the second branching blood vessel B2. In some embodiments, distally advancing the second elongated manipulation member 1724 can cause the second proximal restraint 1738 to bear distally against the second end 1708b2 of the second articulating portion 1708b, thereby imparting distally directed force to the second articulating portion 1708b and moving the second articulating portion 1708b distally. In some embodiments, the second coupling assembly 1736 does not include the second proximal restraint 1738. For example, distal movement of the second elongated manipulation member 1724 can transmit distally directed force to the second articulating portion 1708b via the attachment 1740 and/or another element coupling the second elongated manipulation member 1724 to the second articulating portion 1708b. According to various embodiments, the first elongated shaft 1712, the second elongated shaft 1714, the first elongated manipulation member 1722, and the second elongated manipulation member 1724 can be distally advanced together to urge the second articulating portion 1708b distally. Distal advancement of the second articulating portion 1708b can result in axial compression of the second articulating portion 1708b, radial expansion of the second articulating portion 1708b, and/or movement of the articulating portion 1708b into the second branching blood vessel B2. In some embodiments, the second articulating portion 1708b can be configured to expand from a constrained state (assumed while positioned within the lumen 1718 of the second elongated shaft 1714) to a partially expanded state within the lumen 1716 of the first elongated shaft 1712. For example, the second articulating portion 1708b can expand into contact with the first elongated shaft 1712 once expelled from the lumen 1718 of the second elongated shaft 1714.

Retaining the second end 1708a2 of the first articulating portion 1708a and the engagement member 1732 of the first coupling assembly 1726 within the lumen 1718 of the second elongated shaft 1714 while manipulating the second articulating portion 1708b allows the expandable device 1700 to be resheathed into the lumen 1716 even though the second articulating portion 1708b has been expelled from the lumen 1718. It may be useful to resheath the expandable device 1700 into the lumen 1716 so that the expandable device 1700 (or one or more portions thereof) can be repositioned and/or reoriented at the treatment site or removed from the patient.

Figure 18C:
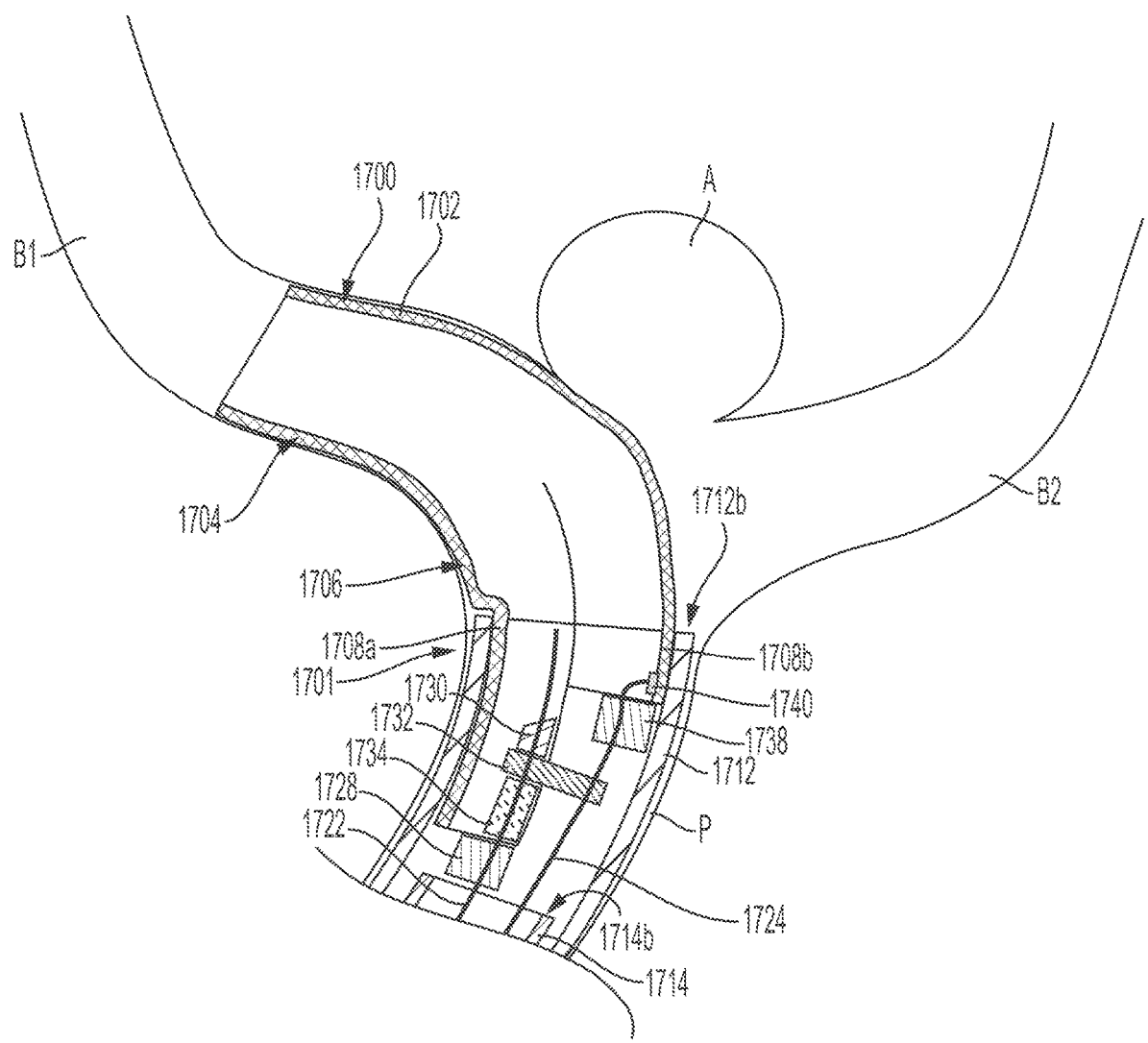

As shown in FIG. 18C, the first articulating portion 1708a can be expelled from the lumen 1718 of the second elongated shaft 1714 such that the first articulating portion 1708a assumes a partially expanded state within the lumen 1716 of the first elongated shaft 1712. As described with reference to expelling the first portion 1704 from the lumen 1718, expelling the first articulating portion 1708a from the lumen 1718 can comprise moving the first articulating portion 1708a distally relative to the second elongated shaft 1714 and/or moving the second elongated shaft 1714 proximally relative to the first articulating portion 1708a. In any case, once the engagement member 1732 of the first coupling assembly 1726 is expelled from the lumen 1718, the region of the first articulating portion 1708a overlying the engagement member 1732 can radially expand away from and separate from the engagement member 1732. Once the engagement member 1732 has disengaged from the first articulating portion 1708a, resheathing of the first articulating portion 1708a into the lumen 1718 may no longer be possible. Once disengaged from the first articulating portion 1708a, the first elongated manipulation member 1722 may be withdrawn proximally into the lumen 1718 and, optionally, proximally through the lumen 1718 and out of the patient's body.

As described herein, at least a portion of the second articulating portion 1708b can be configured to extend over the neck of the aneurysm A to prevent or limit blood flow through the second articulating portion 1708b and into the aneurysm A. However, positioning of the second articulating portion 1708b in the second branching blood vessel B2 presents unique challenges. For example, if the second articulating portion 1708b were released from the constrained state (e.g., from the lumen 1718 of the second elongated shaft 1714, from the lumen 1716 of the first elongated shaft 1712, etc.) while the second end 1708b2 is positioned in the parent blood vessel P, the second articulating portion 1708b may unintentionally expand into contact with the parent blood vessel P and anchor to the parent blood vessel P without covering the neck of the aneurysm A. Moreover, because the second articulating portion 1708b is circumferentially discontinuous to facilitate blood flow through the blood vessels, the rotational orientation of the expandable device 1700 at the treatment site is critically important to the efficacy of treatment with the device 1700. For example, the first portion 1704, the first articulating portion 1708a, and the second articulating portion 1708b could be positioned properly within their respective blood vessels B1, P, B2; however, the device 1700 could be rotated such that the second articulating portion 1708b is not covering the neck of the aneurysm A.

Figure 18D:
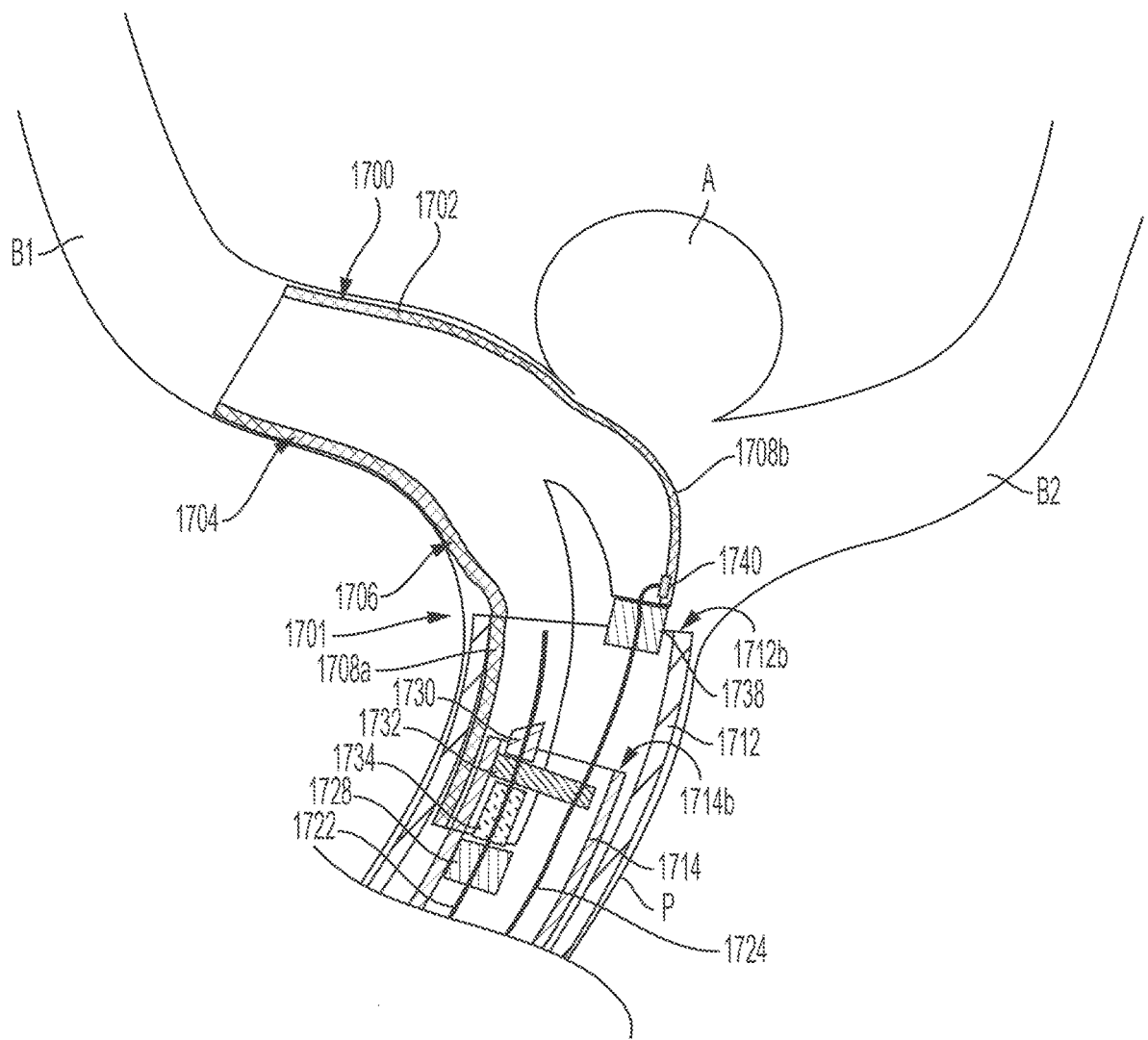

Various aspects of the devices, systems, and methods of the present technology are configured to address such challenges and facilitate positioning and deployment of an expandable device over a neck of an aneurysm. For example, the second elongated manipulation member 1724 can remain secured to the second articulating portion 1708b until actively released by a user. In some embodiments, the second elongated manipulation member 1724 may be secured to the second articulating portion 1708b via an electrolytic, mechanical, or other actuatable attachment so that the second elongated manipulation member 1724 does not necessarily disengage from the second articulating portion 1708b upon release of the second articulating portion 1708b from the lumen 1716 and/or the lumen 1718. Accordingly, the second elongated manipulation member 1724 can be manipulated by a user to modify a position and/or an orientation of the second articulating portion 1708b to facilitate deployment thereof. For example, as shown in FIG. 18D, the second elongated manipulation member 1724 can be advanced distally and/or rotated relative to the first elongated shaft 1712 (or vice versa) to urge the second articulating portion 1708b out of the lumen 1716 of the first shaft 1712, towards the second branching blood vessel B2, and/or over the neck of the aneurysm. During such manipulation of the second elongated manipulation member 1724, the first elongated manipulation member 1722 can remain at the treatment site (e.g., within the parent blood vessel P, etc.). Additionally or alternatively, the first elongated manipulation member 1722 can be drawn proximally through and/or out of the patient's vasculature before, during, or after manipulation of the second elongated manipulation member 1724 to urge the second articulating portion 1708*b* into the second branching blood vessel B2.

Figure 18E:
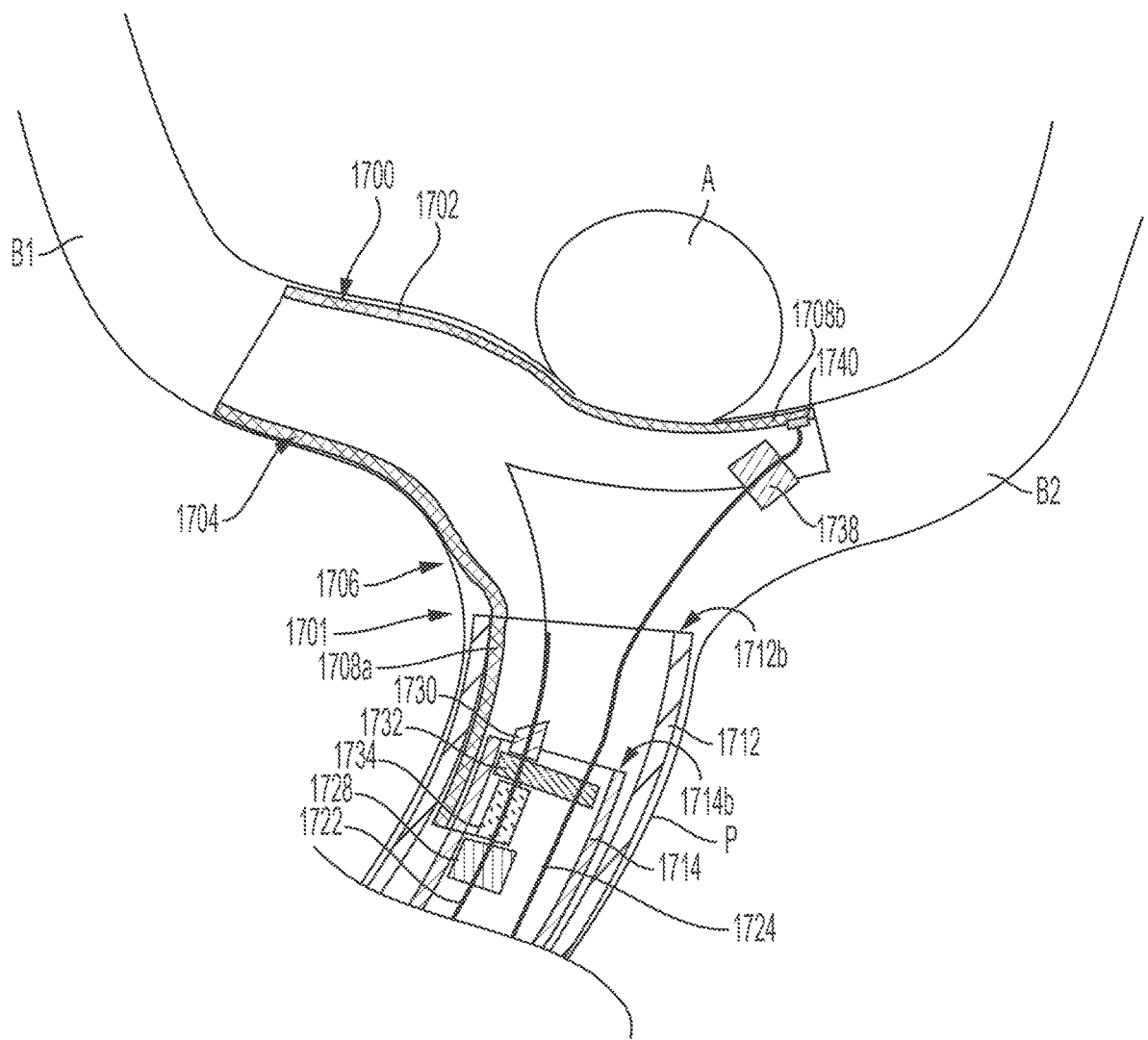
Figure 18F:
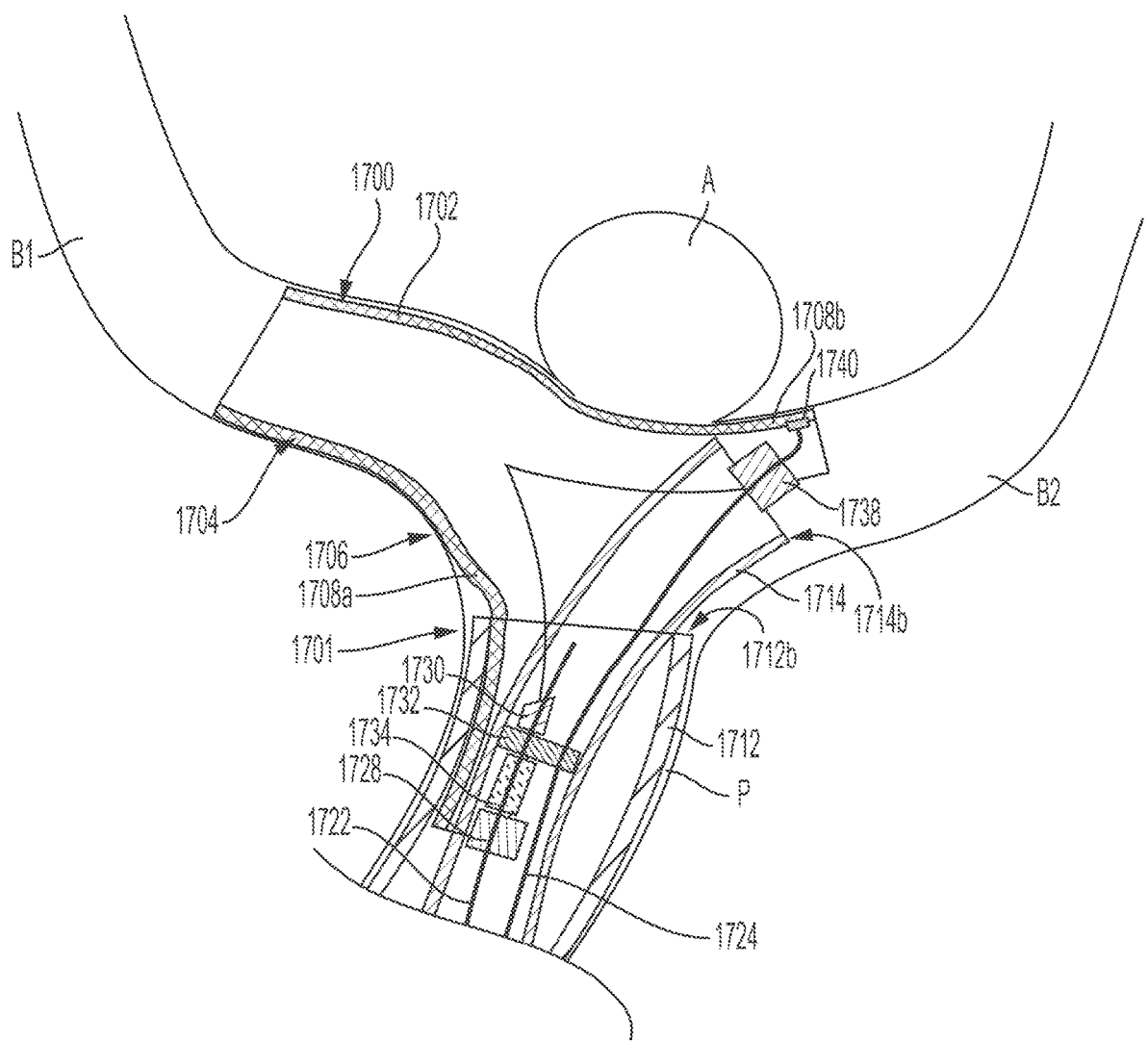

As shown in FIG. 18E, the second elongated manipulation member 1724 can be advanced distally into the second branching blood vessel B2 to position the second articulating portion 1708*b* at an intended location within the second branching blood vessel B2. As shown in FIG. 18F, in some embodiments the second elongated shaft 1714 can be advanced distally towards and/or into the second branching blood vessel B2 to facilitate positioning of the second articulating portion 1708*b* at an intended location within the second branching blood vessel B2. Manipulation of the position and/or orientation of the second articulating portion 1708*b* can be performed following release of the first articulating portion 1708*a* from the lumen 1718 second elongated shaft 1714 to enable the use of specific components of the system 1701 (e.g., the first elongated shaft 1712, the second elongated shaft 1714, the first elongated manipulation member 1722, etc.) for manipulating the second articulating portion 1708*b*. As shown in FIG. 18E, the first elongated manipulation member 1722 may remain within the parent blood vessel P during such manipulation of the second elongated manipulation member 1724. Although not shown in FIG. 18E, in some embodiments the first elongated manipulation member 1722 may be advanced distally with the second elongated manipulation member 1724 to position the second articulating portion 1708*b* in the second branching blood vessel B2. Additionally or alternatively, the first elongated manipulation member 1722 can be drawn proximally through and/or out of the patient's vasculature before, during, or after manipulation of the second elongated manipulation member 1724 position the second articulating portion 1708*b* at the intended position in the second branching blood vessel B2. In some cases, following release of the first articulating portion 1708*a* from the second shaft 1714, the second elongated manipulation member 1724 (see FIGS. 18E and 18F), the second shaft 1714 (see FIG. 18F), and optionally the first elongated manipulation member 1722 (although not shown in FIGS. 18E and 18F), can be advanced distally relative to the first elongated shaft 1712 and/or into the second branching blood vessel B2 to urge the second articulating portion 1708*b* into the second branching blood vessel B2.

In various embodiments, the second articulating portion 1708*b* can be manipulated until the second articulating portion 1708*b* is at least partially positioned within the second branching blood vessel B2, at an intended location, and/or over the neck of the aneurysm A. As the second articulating portion 1708*b* is expelled from the lumen 1716 of the first elongated shaft 1712, the second articulating portion 1708*b* can assume an expanded state. According to various embodiments, the second articulating portion 1708*b* can fully expand while secured to the second elongated manipulation member 1724. In some embodiments, the second articulating portion 1708*b* does not fully expand until released from the second elongated manipulation member 1724. In any case, the second articulating portion 1708*b* can be released from the second elongated manipulation member 1724 to deploy the second articulating portion 1708*b* in the expanded state at the intended location. In the expanded state, the second articulating portion 1708*b* can be disposed at an angle to the first portion 1704 and/or the first articulating portion 1708*a* based on a geometry of the treatment site. For example, as shown in FIGS. 18E-18G, the second articulating portion 1708*b* can be angled with respect to the first portion 1704 such that the first portion 1704 and the second articulating portion 1708*b* substantially conform to the walls of the first and second branching blood vessels B1, B2, respectively.

According to various embodiments, the attachment 1740 can be configured to selectively detach from the second articulating portion 1708*b* and/or the second elongated manipulation member 1724 to permit selective detachment of the second articulating portion 1708*b* from the second elongated manipulation member 1724. According to various embodiments, the second articulating portion 1708*b* can be released from the second elongated manipulation member 1724 by actuating the attachment 1740 therebetween. In some embodiments, the attachment 1740 can be electrically corrodible such that application of electrical energy to the attachment 1740 while the attachment 1740 is in the presence of an electrolyte (e.g., blood, etc.) causes the attachment 1740 to dissolve so that the second articulating portion 1708*b* can separate from the second elongated manipulation member 1724. According to various embodiments, the second articulating portion 1708*b* is mechanically detachable and/or thermally detachable from the second elongated manipulation member 1724.

Figure 18G:
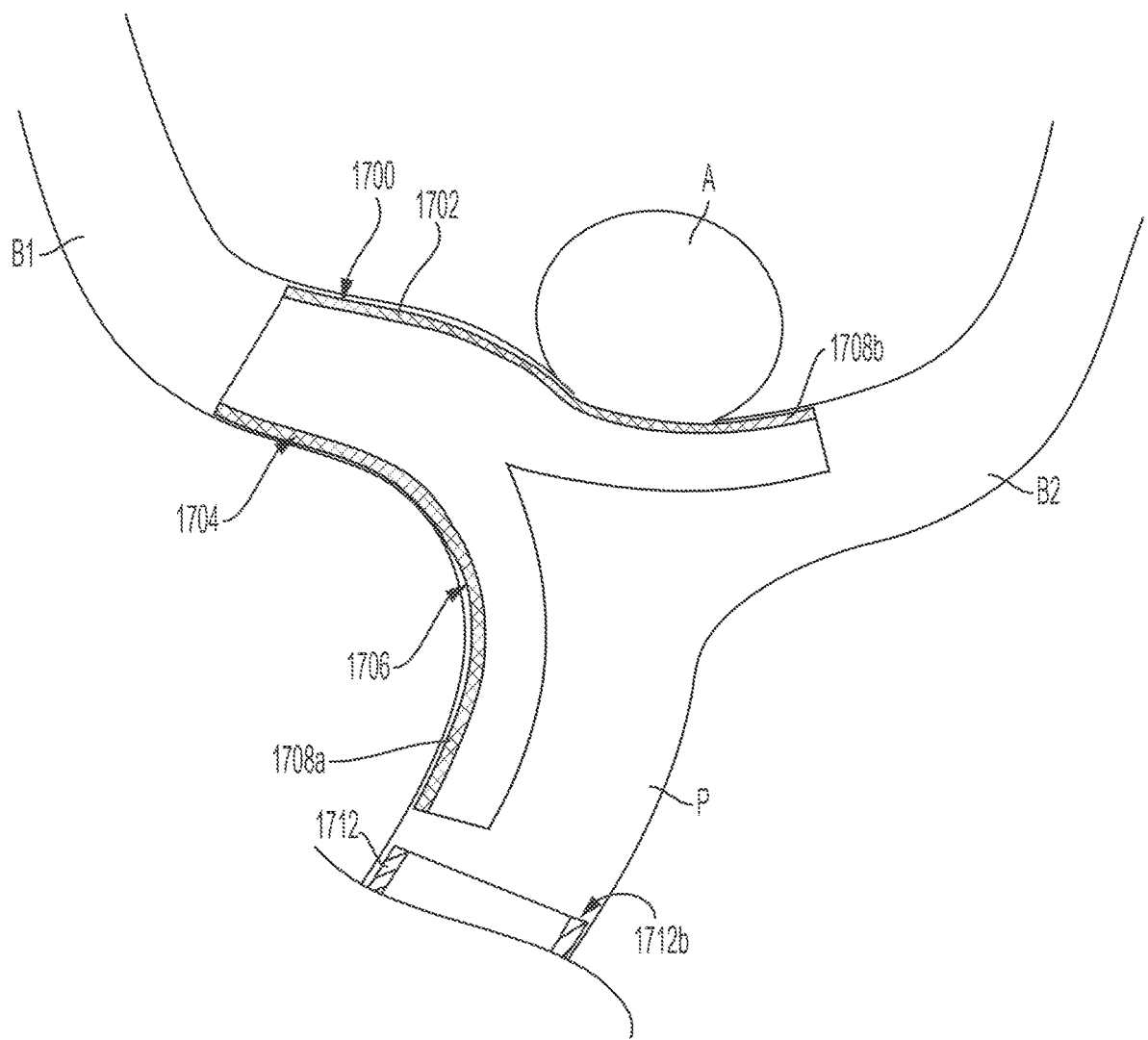

As shown in FIG. 18G, the first elongated shaft 1712 can be withdrawn proximally relative to the first articulating portion 1708*a* to release the first articulating portion 1708*a* from the lumen 1716 of the first elongated shaft 1712 and allow the first articulating portion 1708*a* to expand into contact with the wall of the parent blood vessel P. In some embodiments, the first articulating portion 1708*a* is expelled from the lumen 1716 of the first elongated shaft 1712 prior to release of the second articulating portion 1708*b* from the second elongated manipulation member 1724. Additionally or alternatively, the first articulating portion 1708*a* can be expelled from the lumen 1716 of the first elongated shaft 1712 after releasing the second articulating portion 1708*b* from the second elongated manipulation member 1724.

Once the expandable device 1700 is deployed at the treatment site, the expandable device 1700 can prevent or limit blood flow into the aneurysm A while permitting substantially unobstructed blood flow from the parent blood vessel P to the first and second branching blood vessels B1, B2. As shown in FIGS. 18E-18G, in some embodiments the second articulating portion 1708*b* is at least partially positioned over the neck of the aneurysm. In various embodiments, the first portion 1704 and/or the first articulating portion 1708*a* is at least partially positioned over the neck of the aneurysm. In some embodiments, the first ends 1708*a*1, 1708*b*1 of the first and second articulating portions 1708*a*, 1708*b* are configured to be positioned at or near an opening to the first branching blood vessel B1. Additionally or alternatively, the first end 1708*a*1 of the first articulating portion 1708*a* and/or the first end 1708*b*1 of the second articulating portion 1708*b* can be configured to be positioned at or near the opening of the parent blood vessel P. In some embodiments, the first end 1708*b*1 of the second articulating portion 1708*b* is configured to be positioned near the opening of the second branching blood vessel B2.

One or more parameters of the mesh 1702 can vary throughout the device 1700 based on an intended position and/or function of a specific portion of the device 1700. For example, a portion of the device 1700 configured to be positioned over the neck of the aneurysm A (e.g., at least a portion of the second articulating portion 1708*b*, etc.) can have a lower porosity and/or a greater surface coverage than other portions of the device 1700. Accordingly, when the device 1700 is deployed at the treatment site, the portion of the device 1700 positioned over the neck of the aneurysm A can effectively occlude the aneurysm A. In some embodiments, one or more portions of the device 1700 configured to anchor to a wall of a blood vessel (e.g., the first portion 1704, the first articulating portion 1708a, etc.) can have a greater porosity and/or lower surface coverage. Additionally or alternatively, such anchoring portions of the device 1700 may be configured to exert a greater chronic outward force on a blood vessel wall to facilitate anchorage. Still, any of the parameters disclosed herein can be substantially constant along a length and/or about a circumference of the device 1700.

FIG. 19 is a side cross-sectional view of an example of a system 1901 for delivering an expandable device 1900 to a treatment site within a patient's vasculature to treat a bifurcation aneurysm. The system 1901 or one or more components thereof can be similar to any of the systems (or corresponding components) disclosed herein. For example, the expandable device 1900 can comprise a mesh 1902 having a first portion 1904 and a second portion 1906 extending away from the first portion 1904 and comprising a first articulating portion 1908a and a second articulating portion 1908b. The first and second articulating portions 1908a, 1908b can be separated by one or more slits 1910. The system 1901 can comprise a first elongated shaft 1912 and/or a second elongated shaft 1914. The first elongated shaft 1912 can have a proximal end portion (not shown in FIG. 19), a distal end portion 1912b configured to be positioned at or near the treatment site, a longitudinal axis extending between the proximal end portion and the distal end portion 1912b, and a lumen 1916. The second elongated shaft 1914 can have a proximal end portion (not shown in FIG. 19), a distal end portion 1914b configured to be positioned at or near the treatment site, a longitudinal axis extending between the proximal end portion and the distal end portion 1914b, and a lumen 1918. The system 1901 can comprise a core assembly 1920 configured to carry the expandable device 1900 and control a position of the expandable device 1900. However, while the system 1701 of FIG. 17 includes two elongated manipulation members 1722, 1724, the system 1901 of FIG. 19 comprises a single elongated manipulation member 1922.

The elongated manipulation member 1922 can comprise a proximal end portion (not shown in FIG. 19), a distal end portion 1922b, and an intermediate portion 1922c proximal of the distal end portion 1922b. As shown in FIG. 19, the intermediate portion 1922c can be configured to be releasably secured to the first articulating portion 1908a of the device 1900 and/or the distal end portion 1922b can be configured to be releasably secured to the second articulating portion 1908b of the device (or vice versa). The elongated manipulation member 1922 can be configured to move the first articulating portion 1908a relative to the second elongated shaft 1914 while the intermediate portion 1922c is secured to the first articulating portion 1908a and/or the elongated manipulation member 1922 can be configured to move the second articulating portion 1908b relative to the second elongated shaft 1914 while the distal portion 1922b is secured to the second articulating portion 1908b.

The intermediate portion 1922c can carry a coupling assembly 1926 configured to engage the first articulating portion 1908a, which can be similar to the first coupling assembly 1726 described with reference to FIG. 17. For example, the coupling assembly 1926 can include a proximal restraint 1928, a distal restraint 1930, an engagement member 1932, and/or a spacer 1934. As described herein, the proximal restraint 1928 can be configured to bear distally on the first articulating portion 1908a when the elongated manipulation member 1922 is moved distally so that the first articulating portion 1908a moved distally relative to the second elongated shaft 1914. The engagement member 1932 can be configured to engage the first articulating portion 1908a (e.g., via contact with an inner surface of the first articulating portion 1908a, via mechanical interlock with pores of the first articulating portion 1908a, etc.) so that the engagement member 1932 is configured to transmit proximally directed resheathing force and/or distally directed delivery force to the first articulating portion 1908a.

The distal portion 1922b of the elongated manipulation member 1922 can releasably secured to the second articulating portion 1908b. For example, the distal portion 1922b can secure to the second articulating portion 1908b via a selectively releasable attachment 1940. The attachment 1940 can be electrolytically, mechanically, thermally, or otherwise degradable to permit separation of the second articulating portion 1908b from the elongated manipulation member 1922. The attachment 1940 can be configured such that separation of the second articulating portion 1908b from the elongated manipulation member 1922 does not occur until desired and specifically caused by a user. As shown in FIG. 19, the elongated manipulation member 1922 can comprise a radial bend between the intermediate portion 1922c and the distal portion 1922b. Such a radial bend can facilitate steering and/or delivery of the second articulating portion 1908b into a second branching blood vessel.

Figure 20A:
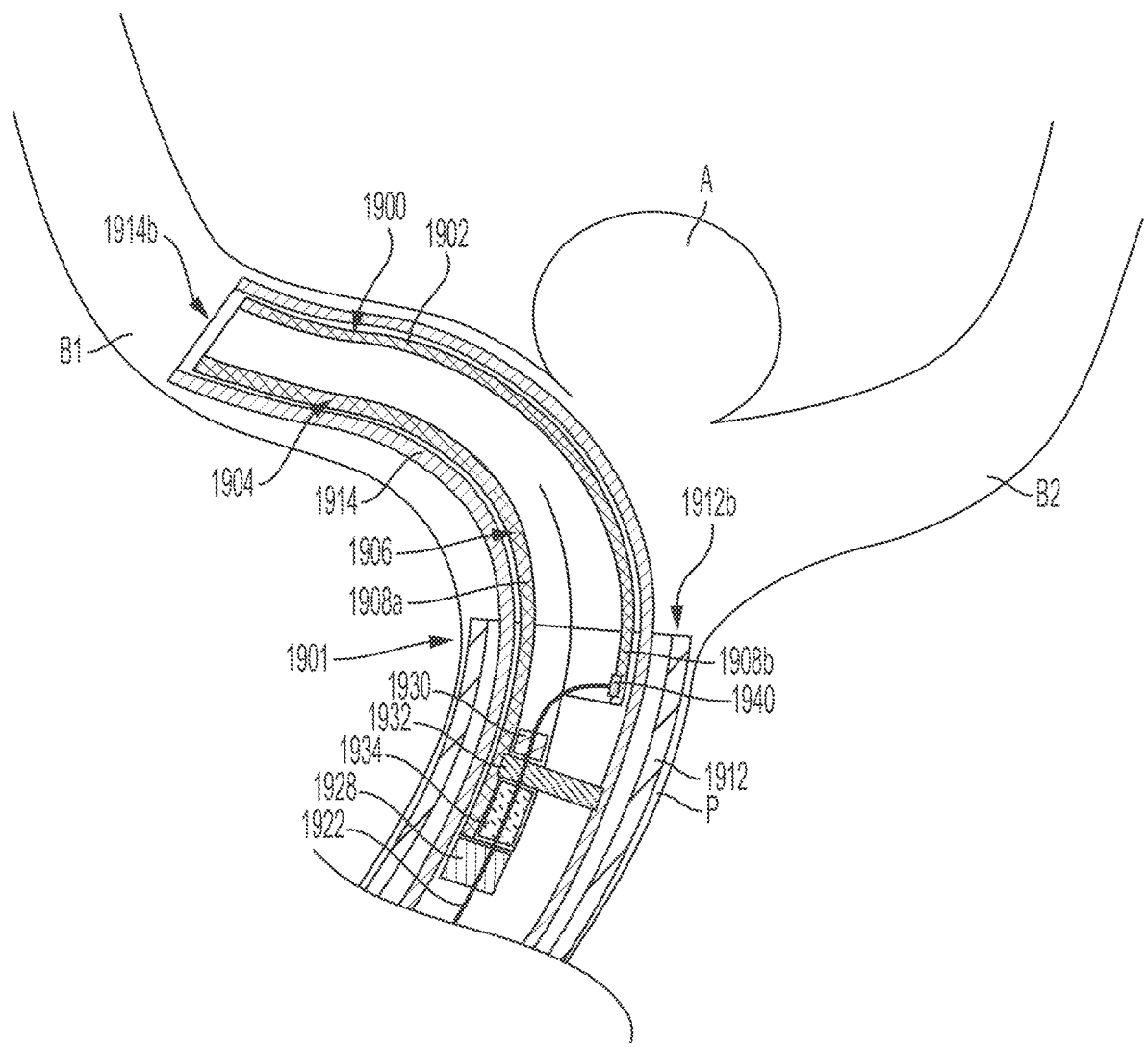
FIGS. 20A-20G illustrate various stages of a method of delivering of an expandable device to a blood vessel bifurcation in accordance with embodiments of the present technology.
Figure 20B:
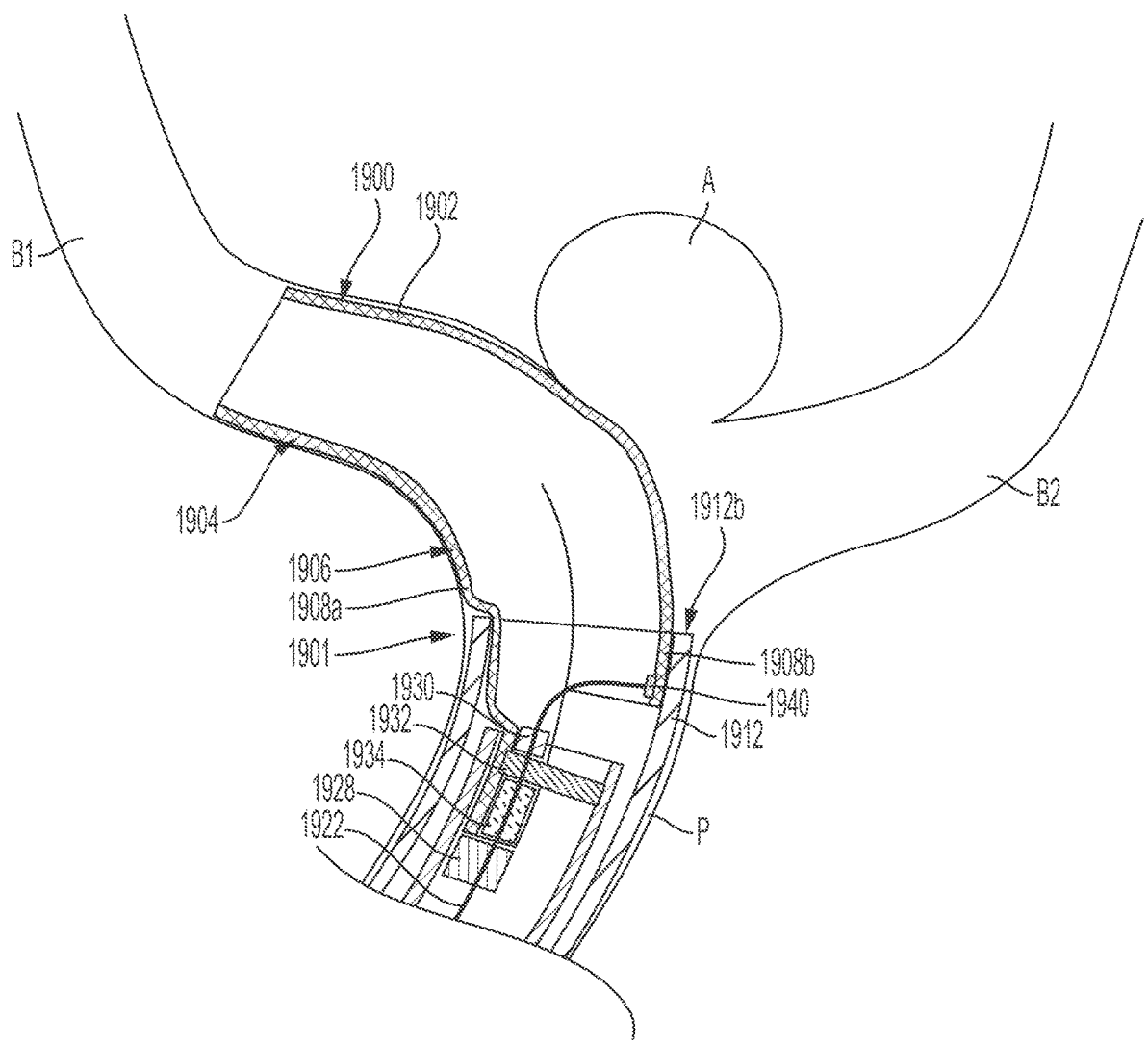
Figure 20C:
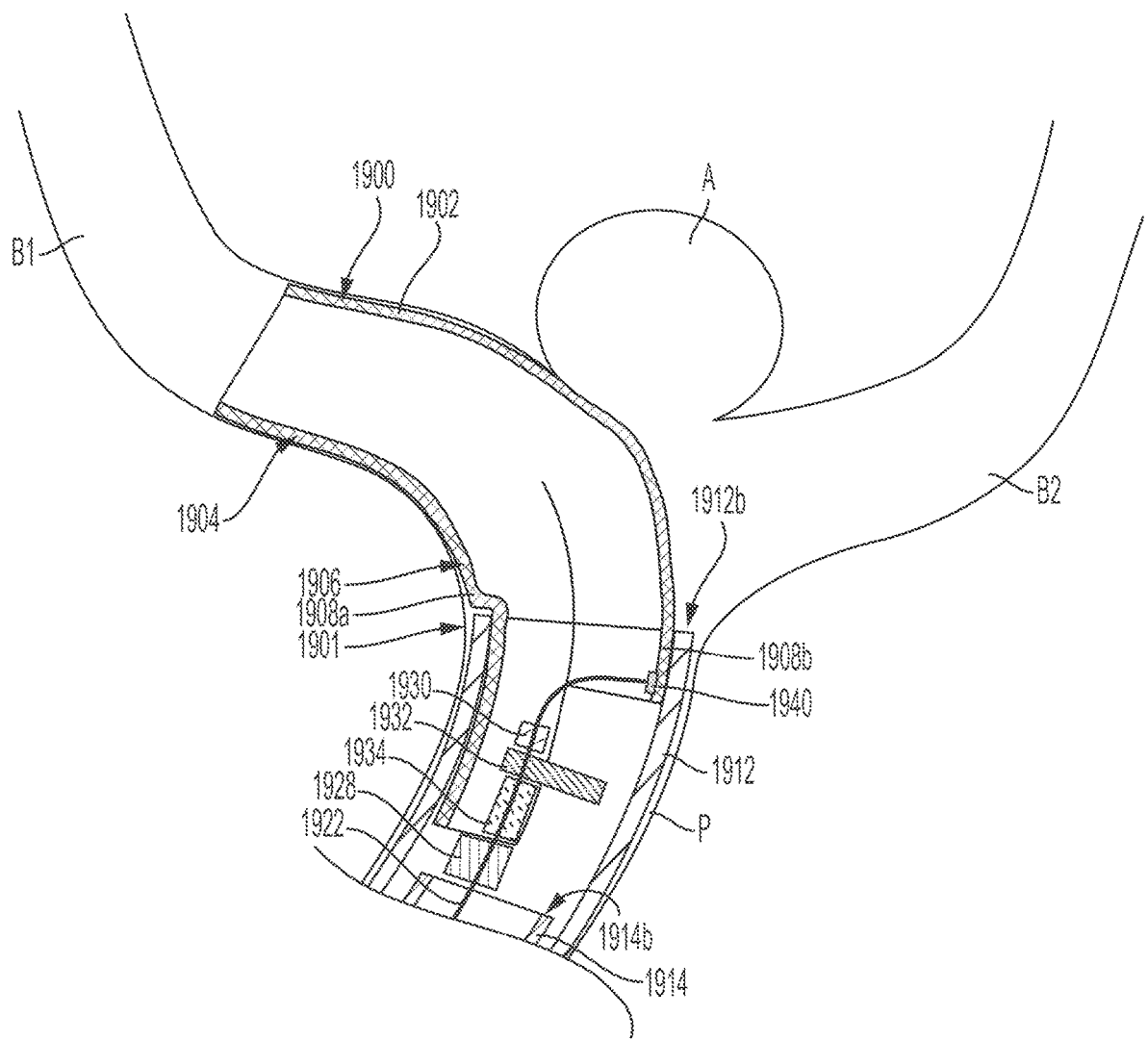

FIGS. 20A-20G illustrate various stages of a method of delivering the expandable device 1900 shown in FIG. 19 using the system 1901 of FIG. 19. Such a method can be similar to the method of delivering the expandable device 1700 using the system 1701 shown in FIGS. 18A-18G. For example, as shown in FIG. 20A, the distal end portion 1914b of the second elongated shaft 1914 and the first portion 1904 of the expandable device 1900 can be advanced into a lumen of a first branching blood vessel B1 of a treatment site in a patient's vasculature. As previously described and as shown in FIG. 20B, the first portion 1904 can be expelled from the lumen 1918 of the second elongated shaft 1914 so that the first portion 1904 expands into apposition with a wall of the first branching blood vessel B1.

Figure 20D:
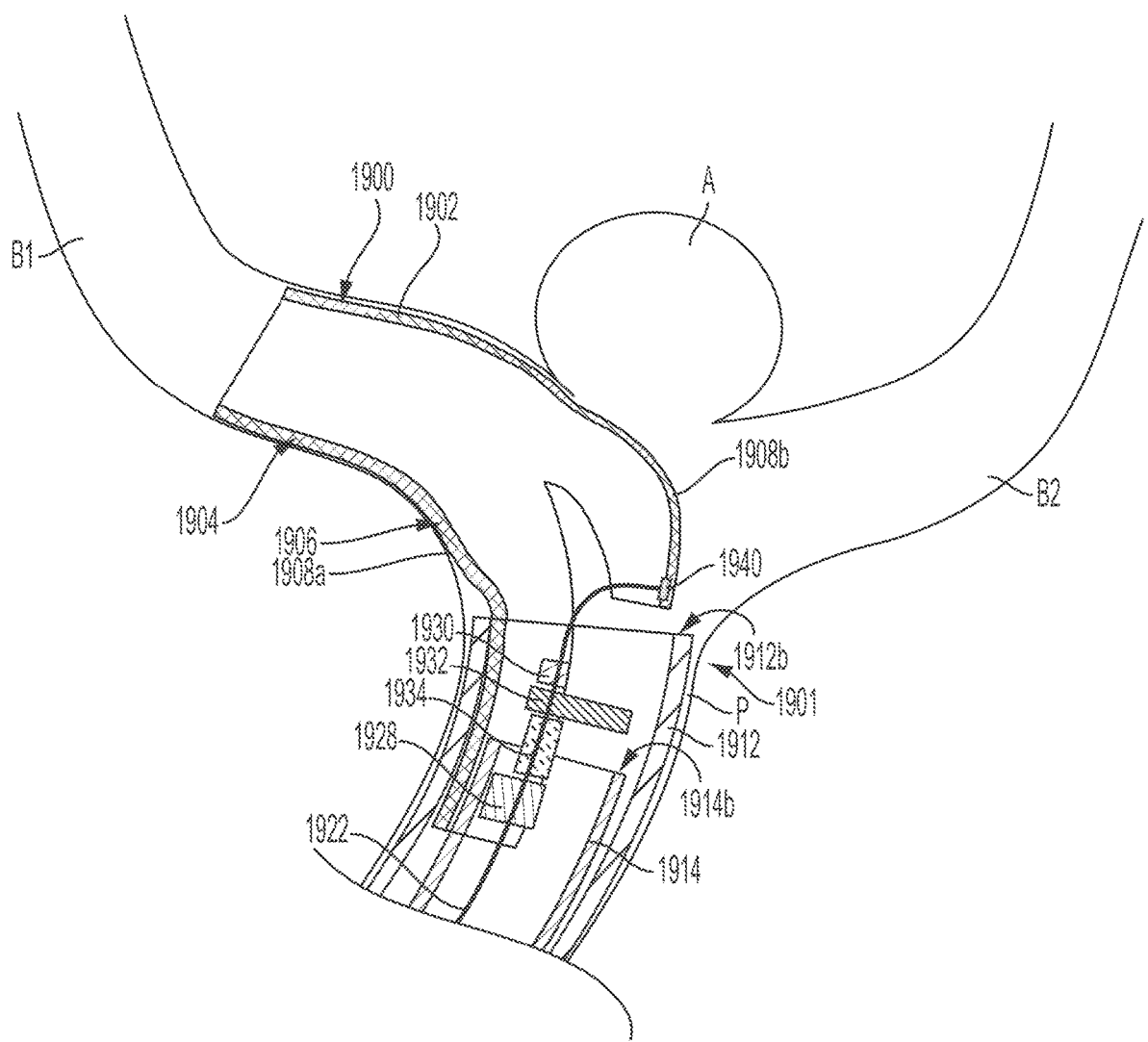
Figure 20E:
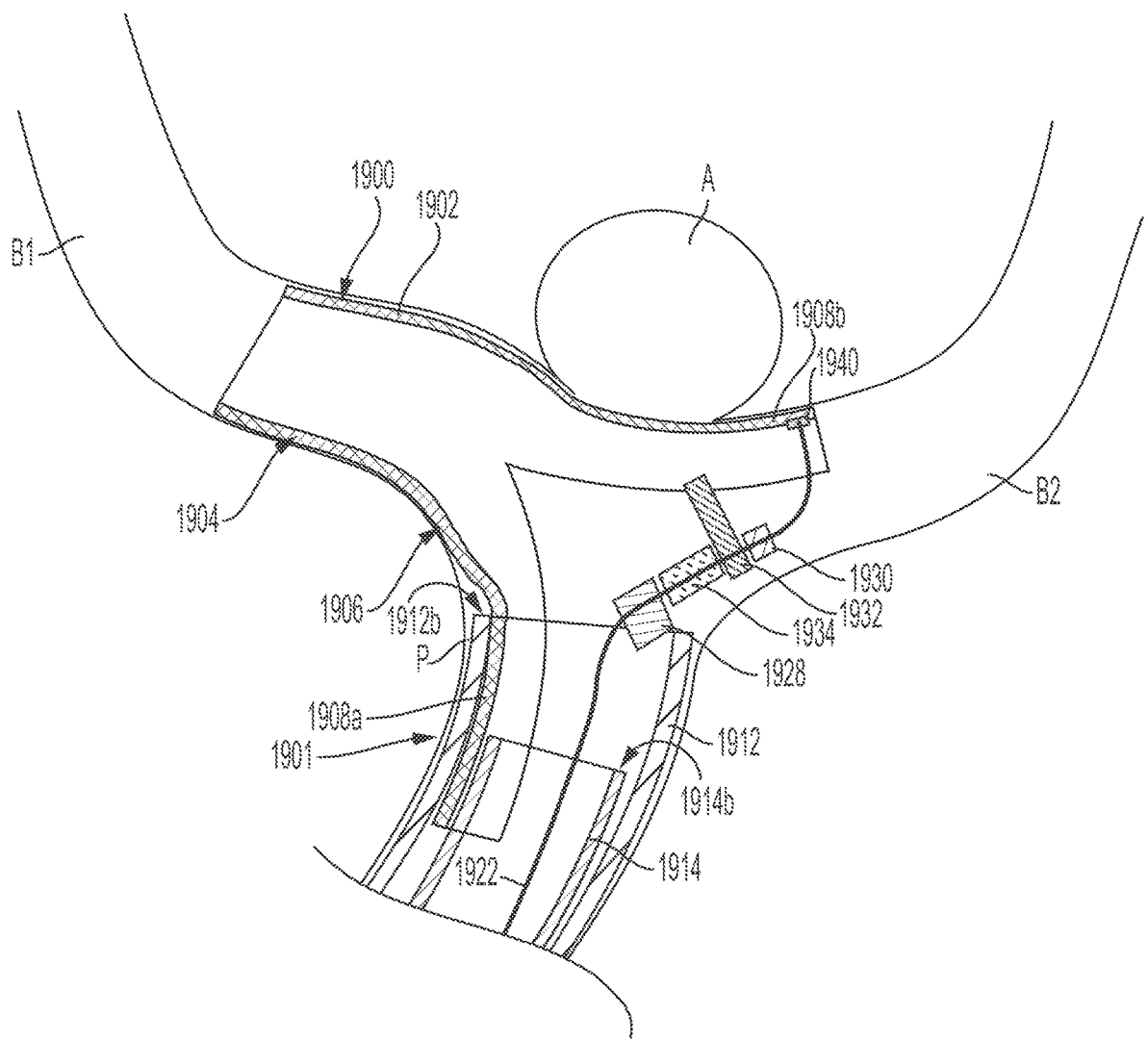
Figure 20F:
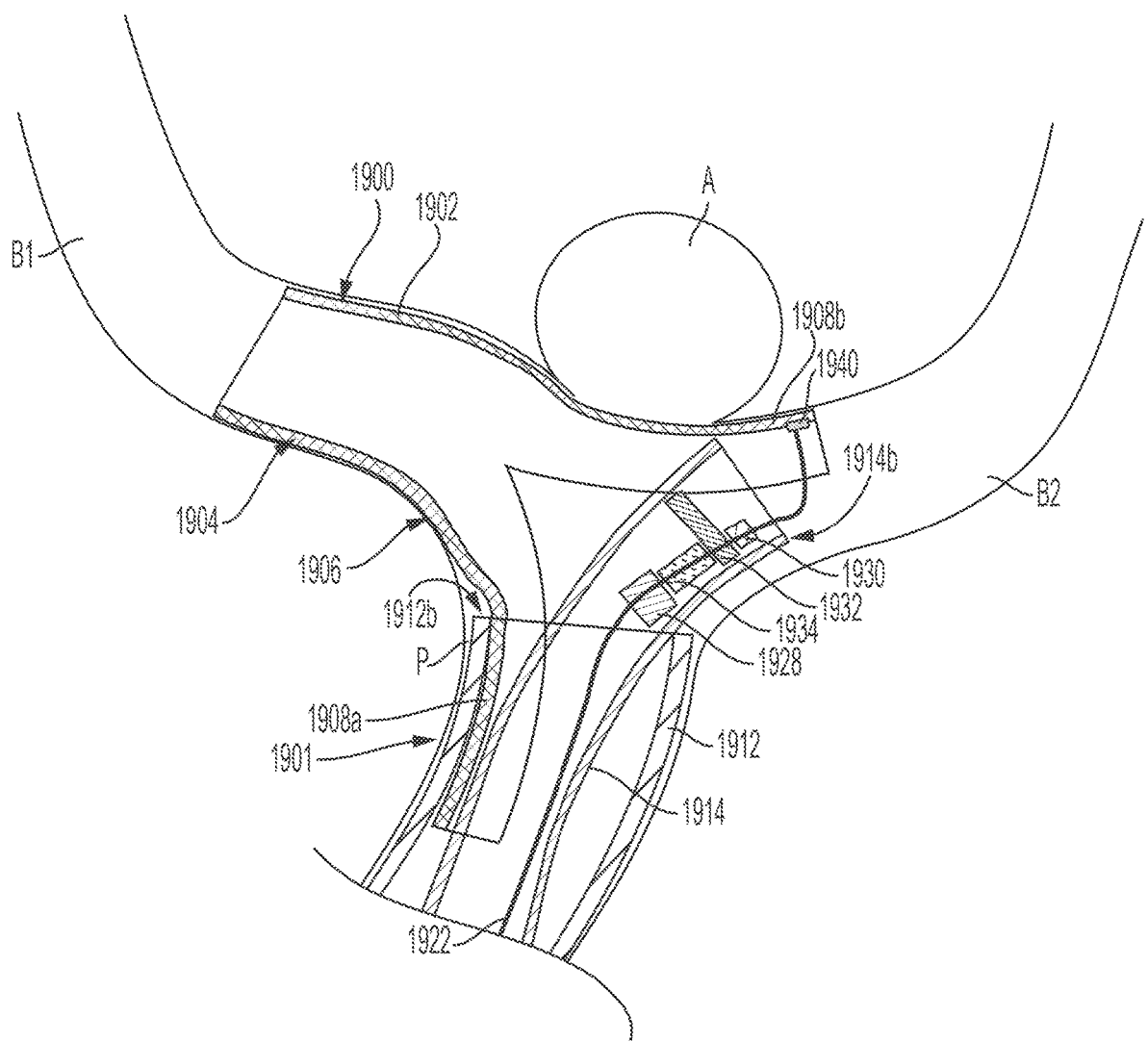
Figure 20G:
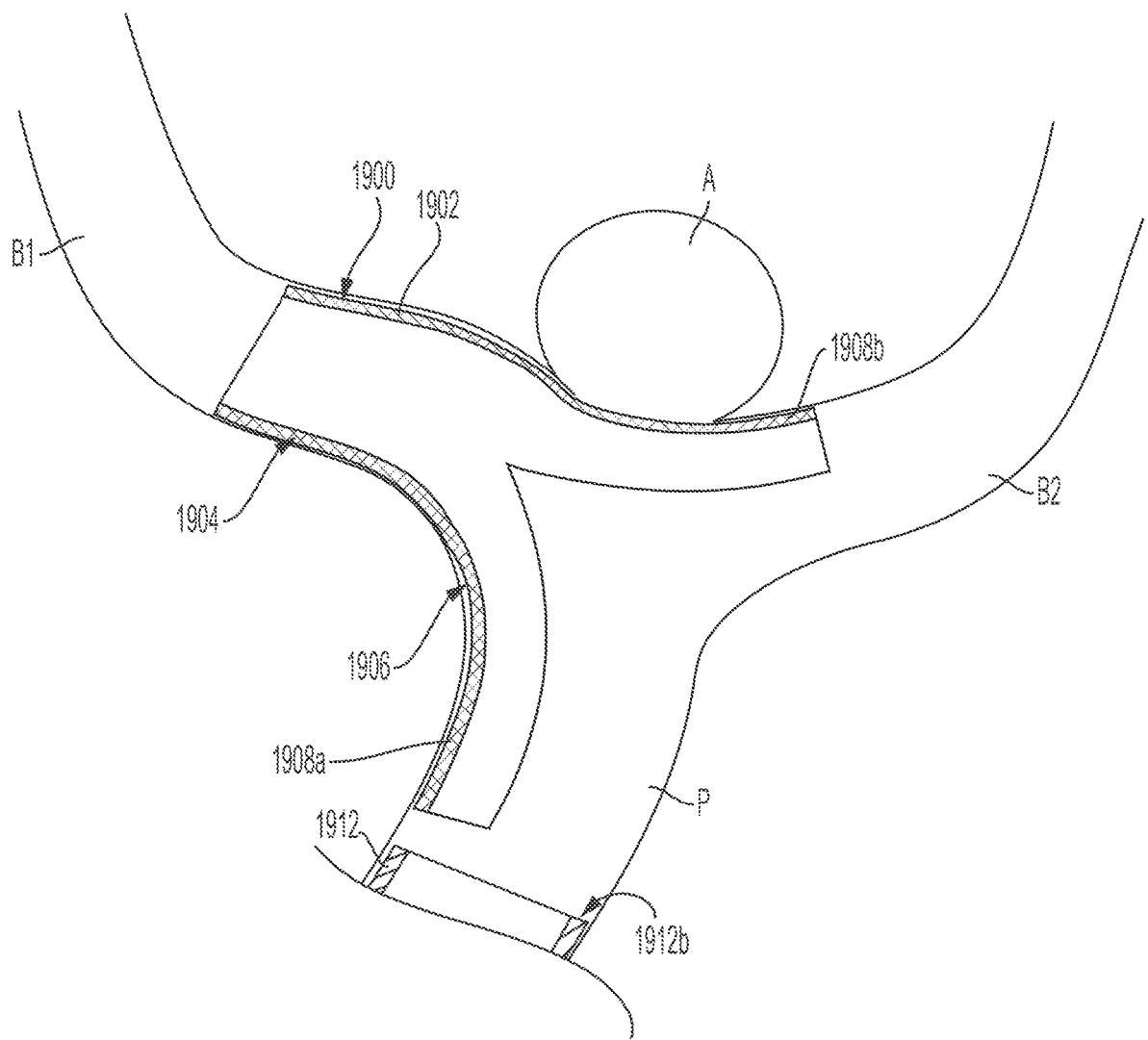

As shown in FIGS. 19-20G, the elongated manipulation member 1922 both carries the coupling assembly 1926 configured to engage the first articulating portion 1908a of the expandable device 1900 and is attached to the second articulating portion 1908b at the attachment 1940. As shown in FIG. 20C, the first articulating portion 1908a can be expelled from the lumen 1918 of the second elongated shaft 1914 so that the first articulating portion 1908a radially expands and separates from the coupling assembly 1926. In such embodiments and others, at least a portion of the first articulating portion 1908a can remain within the lumen 1916 of the first elongated shaft 1912.

As shown in FIGS. 20D-20F, the elongated manipulation member 1922 and/or the second elongated shaft 1914 can be manipulated to urge the second articulating portion 1908b from the lumen 1918 of the second elongated shaft 1914 and into the second branching blood vessel B2. As previously noted, the radial bend in the elongated manipulation member 1922 can facilitate rotation and steering of the second articulating portion 1908b into the second branching blood vessel B2. In various embodiments, for example as shown in FIG. 20F, the second elongated shaft 1914 can be advanced distally along with the elongated manipulation member 1922. The stiffness of the second elongated shaft 1914 can facilitate distal advancement, rotation, or other manipulation of the second articulating portion 1908b into an intended position at the treatment site. FIG. 20G shows an example of the expandable device 1900 deployed at the treatment site such that the device 1900 at least partially covers and occludes the neck of the aneurysm A.

CONCLUSION

Although many of the embodiments are described above with respect to systems, devices, and methods for treating cerebral aneurysms, the technology is applicable to other applications and/or other approaches, such as pulmonary or cardiac applications. Moreover, other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described above with reference to FIGS. 1A-20G.

The descriptions of embodiments of the technology are not intended to be exhaustive or to limit the technology to the precise form disclosed above. Where the context permits, singular or plural terms may also include the plural or singular term, respectively. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

The invention claimed is:

1. A system for delivering an expandable device to a treatment site at a blood vessel bifurcation of a patient, the system comprising:
an elongated shaft having a proximal end portion, a distal end portion configured to be advanced to the treatment site, and a sidewall defining a lumen;
the expandable device comprising a mesh having a circumferentially continuous first portion, a circumferentially discontinuous second portion coupled to the first portion, and a circumferentially discontinuous third portion coupled to the first portion, the expandable device being configured for (i) advancement through the lumen of the elongated shaft in a constrained configuration in which the first portion is positioned distal of the second portion and the third portion and the second portion extends parallel to the third portion, and (ii) deployment at the treatment site into an expanded configuration such that the first portion is positioned in a first branching blood vessel, the second portion is positioned in a parent blood vessel, and the third portion is positioned in a second branching blood vessel such that the second portion does not extend parallel to the third portion and the mesh extends across a neck of an aneurysm without substantially impeding blood flow from the parent blood vessel into the first and second branching blood vessels; and
a core assembly carrying the expandable device and configured for advancement through the lumen of the elongated shaft, the core assembly comprising:
a first elongated manipulation member carrying a proximal restraint positioned proximally of a proximal region of the second portion of the mesh and configured to engage the proximal region of the second portion of the mesh such that distal movement of the first elongated manipulation member causes the proximal restraint to imparts distally directed force to the proximal region of the second portion of the mesh; and
a second elongated manipulation member configured to engage a proximal region of the third portion of the mesh such that distal movement of the second elongated manipulation member imparts distally directed force to the third portion of the mesh,
wherein the first elongated manipulation member and the second elongated manipulation member are radially spaced apart and configured to slide longitudinally relative to one another.

2. The system of claim 1, wherein the first elongated manipulation member carries an engagement member positioned distal of the proximal restraint, and wherein the engagement member is configured to engage the second portion of the mesh so that proximal movement of the first elongated manipulation member causes the engagement member to impart proximally directed force to the second portion of the mesh.

3. The system of claim 2, wherein the engagement member comprises a sprocket with two or more radial projections each configured to extend into a pore of the mesh.

4. The system of claim 2, wherein the engagement member comprises a cylindrically shaped polymer.

5. The system of claim 1, wherein the second elongated manipulation member comprises a proximal end portion and a distal end portion, and wherein the distal end portion of the second elongated manipulation member is releasably secured to the proximal region of the third portion.

6. The system of claim 5, wherein the second elongated manipulation member is radially bent between the proximal end portion and the distal end portion of the second elongated manipulation member.

7. The system of claim 1, wherein the second elongated manipulation member is secured to the proximal region of the third portion via an electrolytically corrodible attachment.

8. The system of claim 1, wherein the second elongated manipulation member is secured to the proximal region of the third portion via a mechanically separable attachment.

9. The system of claim 1, wherein the mesh is configured to prevent or limit fluid flow through a sidewall of the mesh.

10. The system of claim 1, wherein the elongated shaft is a first elongated shaft, the system further comprising a second elongated shaft having a proximal end portion, a distal end portion configured to be advanced to the treatment site, and a sidewall defining a lumen, and wherein the lumen of the second elongated shaft is configured to slidably receive the first elongated shaft therethrough.

11. The system of claim 1, wherein the proximal restraint is configured to abut a proximal facing surface of the proximal region of the second portion of the mesh when the first elongate manipulation member is distally advanced.

12. A system for delivering an expandable device to a treatment site at a blood vessel bifurcation of a patient, the system comprising:
  an elongated shaft having a proximal end portion, a distal end portion configured to be advanced to the treatment site, and a sidewall defining a lumen;
  the expandable device comprising a circumferentially continuous first portion, a circumferentially discontinuous second portion coupled to the first portion, and a circumferentially discontinuous third portion coupled to the first portion, the expandable device being configured for (i) advancement through the lumen of the elongated shaft in a constrained configuration in which the first portion is positioned distal of the second portion and the third portion and the second portion extends parallel to the third portion, and (ii) deployment at the treatment site into an expanded configuration such that the first portion is positioned in a first branching blood vessel, the second portion is positioned in a parent blood vessel, and the third portion is positioned in a second branching blood vessel such that the second portion does not extend parallel to the third portion and the device extends across a neck of an aneurysm without substantially impeding blood flow from the parent blood vessel into the first and second branching blood vessels; and
  an elongated manipulation member carrying the expandable device and configured for advancement through the lumen of the elongated shaft, the elongated manipulation member comprising a proximal end portion, a distal end portion releasably secured to the third portion of the device, and an intermediate portion between the proximal end portion of the elongated manipulation member and the distal end portion of the elongated manipulation member, the intermediate portion being releasably secured to the second portion of the device and carrying a pusher positioned proximally of a proximal region of the second portion,
  wherein the elongated manipulation member is configured to move the second portion of the device relative to the elongated shaft while the intermediate portion of the elongated manipulation member is secured to the second portion of the device, wherein distal movement of the elongated manipulation member is configured to cause distal movement of the pusher such that the pusher imparts distally directed force to the proximal region of the second portion, and wherein the elongated manipulation member is configured to move the third portion of the device relative to the elongated shaft while the distal portion of the elongated manipulation member is secured to the third portion of the device, and
  wherein release of the distal end portion of the elongated manipulation member from the third portion of the device is independent of release of the intermediate portion of the elongated manipulation member from the second portion of the device.

13. The system of claim 12, wherein the distal end portion of the elongated manipulation member is secured to the third portion of the device via an electrolytically corrodible attachment.

14. The system of claim 12, wherein the elongated manipulation member comprises a radial bend between the intermediate portion of the elongated manipulation member and the distal end portion of the elongated manipulation member.

15. The system of claim 12, wherein the distal end portion of the elongated manipulation member is secured to at least one of an inner surface of the third portion of the device or a proximal end of the third portion of the device.

16. The system of claim 12, wherein the intermediate portion of the elongated manipulation member carries an engagement member configured to secure to the second portion of the device when positioned within the lumen of the elongated shaft and configured to release the second portion of the device when positioned outside of the lumen of the elongated shaft.

17. The system of claim 12, wherein the pusher is configured to abut a proximal facing surface of the proximal region of the second portion of the device when the elongate manipulation member is distally advanced.

18. A method of delivering an expandable device to a treatment site over a neck of an aneurysm located at a bifurcation of a parent blood vessel into a first branching blood vessel and a second branching blood vessel, the method comprising:
  advancing a distal end portion of an elongated shaft to the first branching blood vessel;
  positioning the core assembly of claim 1 carrying the expandable device of claim 1 within a lumen of the elongated shaft in a constrained state at the distal end portion of the elongated shaft;
  expelling the first portion of the expandable device from the distal end portion of the elongated shaft so that the first portion expands into contact with a wall of the first branching blood vessel;
  distally advancing the third portion of the device towards the second branching blood vessel by distally advancing at least one of the first elongated manipulation member, the second elongated manipulation member, or the elongated shaft;
  expelling the second portion of the device from the distal end portion of the elongated shaft so that the second portion disengages from the first elongated manipulation member and expands into contact with a wall of the parent blood vessel, wherein expelling the second portion comprises moving the first elongated manipulation member and the elongated shaft longitudinally relative to one another such that the proximal restraint imparts distally directed force to the proximal region of the second portion;
  positioning the third portion of the device within the second branching blood vessel at an intended position and orientation by moving the second elongated manipulation member; and disengaging the second elongated manipulation member from the third portion of the device such that the third portion of the device expands into contact with a wall of the second branching blood vessel.

19. The method of claim 18, further comprising prior to disengaging the second portion of the device from the first elongated manipulation member, retracting the second portion of the device and the first elongated manipulation member proximally into or through the lumen of the elongated shaft.

20. The method of claim 18, wherein the elongated shaft is a first elongated shaft, the method further comprising, before advancing the distal end portion of the first elongated shaft to the first branching blood vessel, advancing a distal end portion of a second elongated shaft to the parent vessel, and wherein the distal end portion of the first elongated shaft is advanced through a lumen of the second elongated shaft.

21. The method of claim 18, wherein disengaging the second elongated manipulation member from the third portion of the device comprises delivering an electrical current to the second elongated manipulation member.

* * * * *